(12) United States Patent
Denlinger et al.

(10) Patent No.: US 11,284,957 B2
(45) Date of Patent: Mar. 29, 2022

(54) ROBOTIC SURGICAL CONTROLS WITH FORCE FEEDBACK

(71) Applicant: Cilag GmbH International, Guaynabo, PR (US)

(72) Inventors: Clinton W. Denlinger, Cincinnati, OH (US); Gregory W. Johnson, Minneapolis, MN (US); Charles J. Scheib, Loveland, OH (US); Jeffrey S. Swayze, West Chester, OH (US)

(73) Assignee: Cilag GmbH International, Zug (CH)

( * ) Notice: Subject to any disclaimer, the term of this patent is extended or adjusted under 35 U.S.C. 154(b) by 174 days.

(21) Appl. No.: 16/354,478

(22) Filed: Mar. 15, 2019

(65) Prior Publication Data
US 2020/0289230 A1    Sep. 17, 2020

(51) Int. Cl.
| | | |
|---|---|---|
| *A61B 34/00* | (2016.01) | |
| *A61B 90/00* | (2016.01) | |
| *A61B 17/29* | (2006.01) | |
| *A61B 34/35* | (2016.01) | |
| *A61B 90/60* | (2016.01) | |

(Continued)

(52) U.S. Cl.
CPC ............ *A61B 34/74* (2016.02); *A61B 17/29* (2013.01); *A61B 34/35* (2016.02); *A61B 90/37* (2016.02); *A61B 90/60* (2016.02); *A61B 2017/00017* (2013.01); *A61B 2017/00022* (2013.01); *A61B 2017/00039* (2013.01); *A61B 2034/301* (2016.02); *A61B 2034/305* (2016.02); *A61B 2034/742* (2016.02)

(58) Field of Classification Search
CPC ......... A61B 34/35; A61B 34/74; A61B 17/29; A61B 90/60; A61B 90/06
See application file for complete search history.

(56) References Cited

U.S. PATENT DOCUMENTS

| | | |
|---|---|---|
| 4,785,180 A | 11/1988 | Dietrich et al. |
| 5,021,969 A | 6/1991 | Okamura et al. |
| 5,855,583 A | 1/1999 | Wang et al. |

(Continued)

FOREIGN PATENT DOCUMENTS

KR    20120068597 A    6/2012

OTHER PUBLICATIONS

Kurata, et al., "Time-of-flight Near-infrared Spectroscopy for Nondestructive Measurement of Internal Quality in Grapefruit," Journal, May 2013, pp. 225-228, vol. 138, Issue 3, Journal of the American Society for Horticultural Science, Japan.

*Primary Examiner* — Tuan V Nguyen

(57) ABSTRACT

An input control device is disclosed. The input control device can be configured to operate in different modes depending on proximity data provided by a proximity detection system. The input control device can include a feedback generator configured to generate feedback in response to the input control device switching between operational modes, the proximity data provided by the proximity detection system, and/or other conditions of the surgical procedure, robotic surgical tool, surgical site, and/or patient. The input control device can include a variable resistance assembly for resisting input control motions applied to an actuator thereof. Additionally or alternatively, the input control device can include an end effector actuator assembly for repositioning the end effector actuator based on feedback from a paired robotic surgical tool.

20 Claims, 49 Drawing Sheets

(51) Int. Cl.
*A61B 34/30* (2016.01)
*A61B 17/00* (2006.01)

(56) References Cited

U.S. PATENT DOCUMENTS

| | | | |
|---|---|---|---|
| 6,587,750 B2 | 7/2003 | Gerbi et al. | |
| 6,704,001 B1 * | 3/2004 | Schena | G05G 9/047 310/12.04 |
| 6,804,012 B2 | 10/2004 | Gombert | |
| 6,810,281 B2 | 10/2004 | Brock et al. | |
| 6,951,535 B2 | 10/2005 | Ghodoussi et al. | |
| 7,516,675 B2 | 4/2009 | Kurtz et al. | |
| 7,747,311 B2 | 6/2010 | Quaid, III | |
| 7,996,110 B2 | 8/2011 | Lipow et al. | |
| 8,063,883 B2 | 11/2011 | Senft et al. | |
| 8,079,950 B2 | 12/2011 | Stern et al. | |
| 8,224,484 B2 | 7/2012 | Swarup et al. | |
| 8,523,043 B2 | 9/2013 | Ullrich et al. | |
| 8,888,789 B2 | 11/2014 | Prisco et al. | |
| 8,996,173 B2 | 3/2015 | Itkowitz et al. | |
| 9,055,961 B2 | 6/2015 | Manzo et al. | |
| 9,161,817 B2 | 10/2015 | Olson et al. | |
| 9,186,046 B2 | 11/2015 | Ramamurthy et al. | |
| 9,274,047 B2 | 3/2016 | Velten et al. | |
| 9,500,473 B2 | 11/2016 | Ramamurthy et al. | |
| 9,808,246 B2 | 11/2017 | Shelton, IV et al. | |
| 9,827,059 B2 | 11/2017 | Robinson et al. | |
| 10,052,766 B2 | 8/2018 | Shirakyan et al. | |
| 10,398,517 B2 | 9/2019 | Eckert et al. | |
| 10,441,370 B2 | 10/2019 | Millman et al. | |
| 10,485,617 B2 | 11/2019 | Crawford et al. | |
| 10,499,996 B2 | 12/2019 | de Almeida Barreto | |
| 10,548,679 B2 | 2/2020 | Carlson et al. | |
| 10,792,034 B2 | 10/2020 | Scheib et al. | |
| 10,835,332 B2 | 11/2020 | Manzo et al. | |
| 10,925,598 B2 | 2/2021 | Scheib et al. | |
| 2003/0109857 A1 | 6/2003 | Sanchez et al. | |
| 2004/0128026 A1 | 7/2004 | Harris et al. | |
| 2004/0243147 A1 | 12/2004 | Lipow | |
| 2008/0001919 A1 | 1/2008 | Pascucci | |
| 2010/0302017 A1 | 12/2010 | Guglielmo | |
| 2012/0143353 A1 | 6/2012 | Kishi | |
| 2012/0221145 A1 | 8/2012 | Ogawa | |
| 2014/0160015 A1 | 6/2014 | Ogawa et al. | |
| 2015/0150573 A1 * | 6/2015 | Van Tol | A61B 18/1447 606/34 |
| 2017/0055819 A1 | 3/2017 | Hansen et al. | |
| 2017/0224428 A1 | 8/2017 | Kopp | |
| 2017/0251900 A1 | 9/2017 | Hansen et al. | |
| 2019/0200905 A1 | 7/2019 | Shelton, IV et al. | |
| 2019/0201111 A1 | 7/2019 | Shelton, IV et al. | |
| 2019/0201120 A1 | 7/2019 | Shelton, IV et al. | |
| 2019/0201142 A1 | 7/2019 | Shelton, IV et al. | |
| 2019/0307524 A1 | 10/2019 | Popovic | |
| 2020/0015668 A1 | 1/2020 | Scheib | |
| 2020/0015897 A1 | 1/2020 | Scheib et al. | |
| 2020/0015898 A1 | 1/2020 | Scheib et al. | |
| 2020/0015899 A1 | 1/2020 | Scheib et al. | |
| 2020/0015900 A1 | 1/2020 | Scheib et al. | |
| 2020/0015901 A1 | 1/2020 | Scheib et al. | |
| 2020/0015902 A1 | 1/2020 | Scheib et al. | |
| 2020/0015903 A1 | 1/2020 | Scheib et al. | |
| 2020/0015906 A1 | 1/2020 | Scheib et al. | |
| 2020/0015907 A1 | 1/2020 | Scheib | |
| 2020/0015914 A1 | 1/2020 | Scheib et al. | |
| 2020/0015917 A1 * | 1/2020 | Cavalier | A61B 34/32 |
| 2020/0015923 A1 | 1/2020 | Scheib et al. | |
| 2020/0015924 A1 | 1/2020 | Scheib et al. | |
| 2020/0015925 A1 | 1/2020 | Scheib | |
| 2020/0289205 A1 | 9/2020 | Scheib et al. | |
| 2020/0289216 A1 | 9/2020 | Denlinger et al. | |
| 2020/0289217 A1 | 9/2020 | Denlinger et al. | |
| 2020/0289219 A1 | 9/2020 | Denlinger et al. | |
| 2020/0289220 A1 | 9/2020 | Denlinger et al. | |
| 2020/0289221 A1 | 9/2020 | Denlinger et al. | |
| 2020/0289222 A1 | 9/2020 | Denlinger et al. | |
| 2020/0289223 A1 | 9/2020 | Denlinger et al. | |
| 2020/0289228 A1 | 9/2020 | Denlinger et al. | |
| 2020/0289229 A1 | 9/2020 | Denlinger et al. | |

* cited by examiner

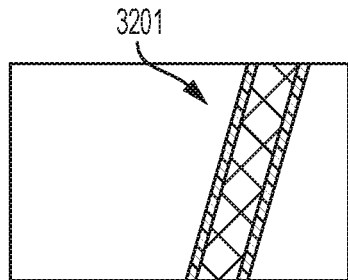
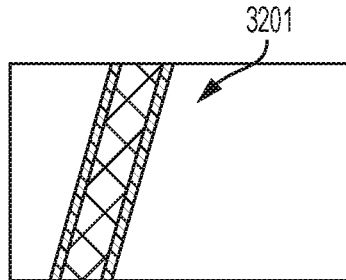
FIG. 32A    FIG. 32B
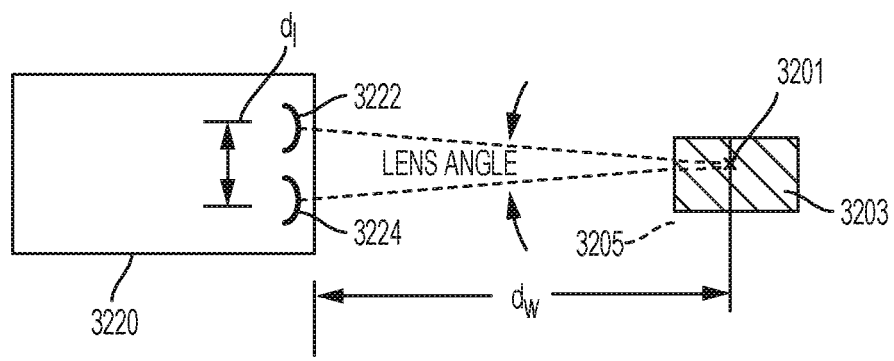
FIG. 33

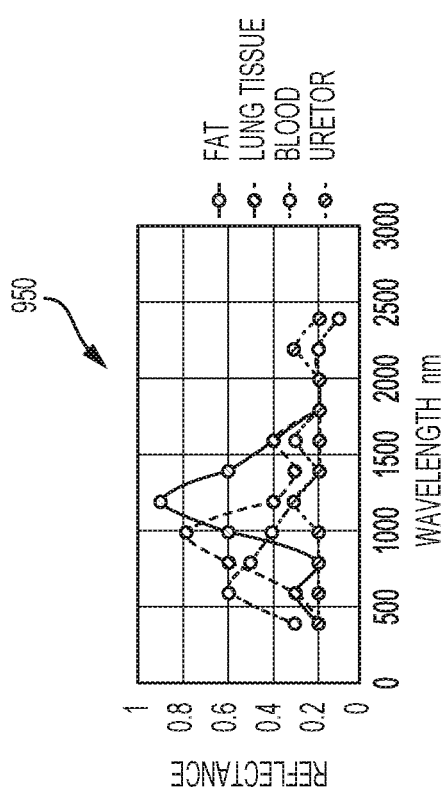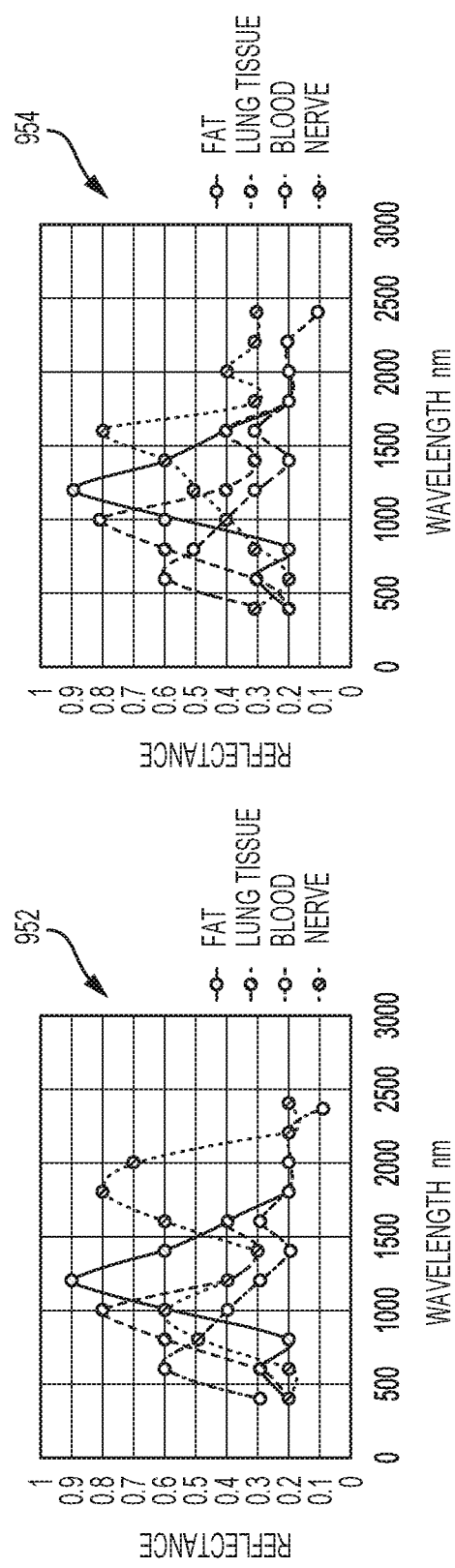
FIG. 38
FIG. 39
FIG. 40

ROBOTIC SURGICAL CONTROLS WITH FORCE FEEDBACK

BACKGROUND

Surgical systems often incorporate an imaging system, which can allow the clinician(s) to view the surgical site and/or one or more portions thereof on one or more displays such as a monitor. The display(s) can be local and/or remote to a surgical theater. An imaging system can include a scope with a camera that views the surgical site and transmits the view to a display that is viewable by a clinician. Imaging systems can be limited by the information that they are able to recognize and/or convey to the clinician(s). For example, certain concealed structures, physical contours, and/or dimensions within a three-dimensional space may be unrecognizable intraoperatively by certain imaging systems. Additionally, certain imaging systems may be incapable of communicating and/or conveying certain information to the clinician(s) intraoperatively.

Robotic systems can be actuated or remotely-controlled by one or more clinicians positioned at control consoles. Input motions at the control console(s) can correspond to actuations of a robotic arm and/or a robotic tool coupled thereto. In various instances, the robotic system and/or the clinician(s) can rely on views and/or information provided by an imaging system to determine the desired robotic actuations and/or the corresponding suitable input motions. The inability of certain imaging systems to provide certain visualization data and/or information may present challenges and/or limits to the decision-making process of the clinician and/or the controls for the robotic system.

SUMMARY

In various aspects, a control system for a robotic surgical system is disclosed, the control system including a robotic tool configured to detect a property of a tissue at a surgical site and an input control device including a base, a joystick coupled to the base, and a handpiece coupled to the joystick. The handpiece includes a variable resistance assembly including a piston, a first jaw coupled to the piston, and a second jaw coupled to the piston. The first jaw and the second jaw are configured to receive user input control motions. The control system further includes a control circuit configured to receive a jaw control signal indicative of the user input control motions received by the first jaw and the second jaw, provide a first output control signal to the robotic tool based on the jaw control signal, receive a tissue property signal indicative of the property of the tissue, and provide a second output control signal to the variable resistance assembly based on the tissue property signal.

In various aspects, a control system for a robotic surgical system is disclosed, the control system including a robotic tool configured to detect a property of a tissue at a surgical site and an input control device including a base, a joystick coupled to the base, and a handpiece coupled to the joystick. The handpiece includes a variable resistance assembly including a piston and a jaw coupled to the piston. The jaw is configured to receive a user input control motion. The control system further includes a control circuit configured to receive a jaw control signal indicative of the user input control motion received by the jaw, provide a first output control signal to the robotic tool based on the jaw control signal, receive a tissue property signal indicative of the property of the tissue, and provide a second output control signal to the variable resistance assembly based on the property of the tissue.

In various aspects, a control system for a robotic surgical system is disclosed, the control system including an input control device including a base, a joystick coupled to the base, and a handpiece coupled to the joystick. The handpiece includes a variable resistance assembly including a piston, a first jaw coupled to the piston, and a second jaw coupled to the piston. The first jaw and the second jaw are configured to receive user input control motions. The control system further includes a control circuit configured to receive jaw control signals indicative of the user input control motions received by the first jaw and the second jaw, provide first output control signals to a robotic tool of the robotic surgical system based on the jaw control signals, receive tissue property signals indicative of a tissue property, and provide second output control signals to the variable resistance assembly based on the tissue property.

FIGURES

The novel features of the various aspects are set forth with particularity in the appended claims. The described aspects, however, both as to organization and methods of operation, may be best understood by reference to the following description, taken in conjunction with the accompanying drawings in which:

FIGS. 13A and 13B depict an end effector of a surgical tool and the user input device of FIG. 6 in corresponding open configurations, wherein FIG. 13A is a plan view of the end effector and FIG. 13B is a plan view of the user input device, according to at least one aspect of the present disclosure.

FIGS. 14A and 14B depict the end effector and the user input device of FIGS. 13A and 13B in corresponding partially-closed configurations, wherein FIG. 14A is a plan view of the end effector and FIG. 14B is a plan view of the user input device, according to at least one aspect of the present disclosure.

FIGS. 15A and 15B depict the end effector and the user input device of FIGS. 13A and 13B in corresponding closed configurations, wherein FIG. 15A is a plan view of the end effector and FIG. 15B is a plan view of the user input device, according to at least one aspect of the present disclosure.

FIGS. 32A and 32B are views of the critical structure taken by the three-dimensional camera of FIG. 31, in which FIG. 32A is a view from a left-side lens of the three-dimensional camera and FIG. 32B is a view from a right-side lens of the three-dimensional camera, according to at least one aspect of the present disclosure.

FIG. 33 is a schematic of the surgical visualization system of FIG. 31, in which a camera-to-critical structure distance $d_W$ from the three-dimensional camera to the critical structure can be determined, according to at least one aspect of the present disclosure.

FIGS. 38-40 depict illustrative hyperspectral identifying signatures to differentiate anatomy from obscurants, wherein FIG. 38 is a graphical representation of a ureter signature versus obscurants, FIG. 39 is a graphical representation of an artery signature versus obscurants, and FIG. 40 is a graphical representation of a nerve signature versus obscurants, according to at least one aspect of the present disclosure.

Figure 41:
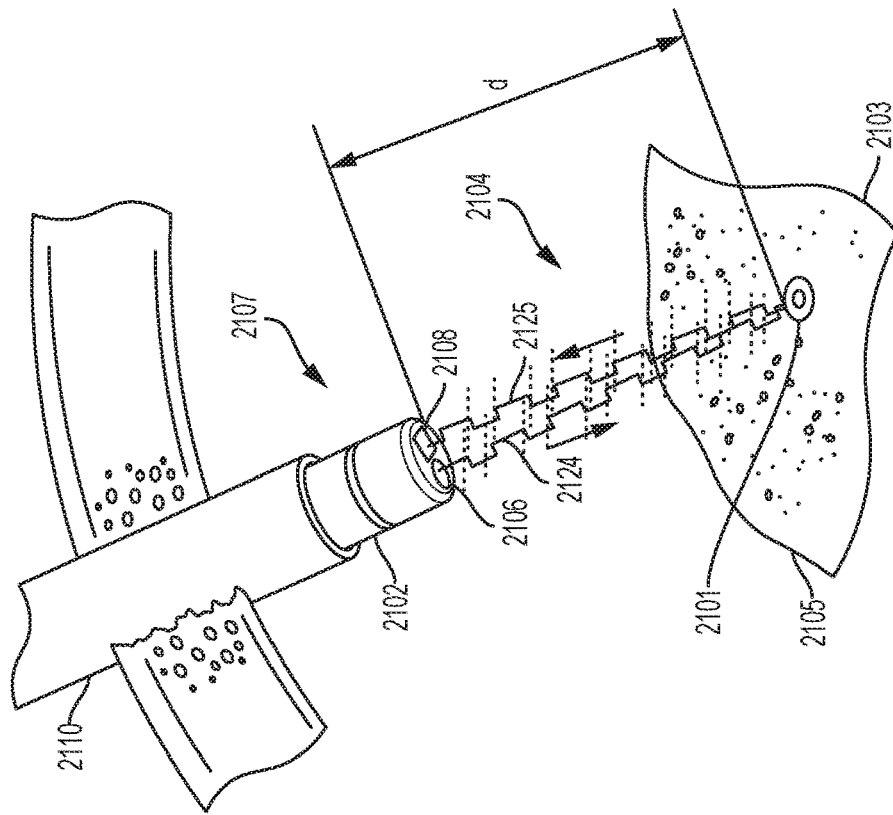

FIG. 41 is a schematic of a near infrared (NIR) time-of-flight measurement system configured to sense distance to a critical anatomical structure, the time-of-flight measurement system including a transmitter (emitter) and a receiver (sensor) positioned on a common device, according to at least one aspect of the present disclosure.

Figure 42:
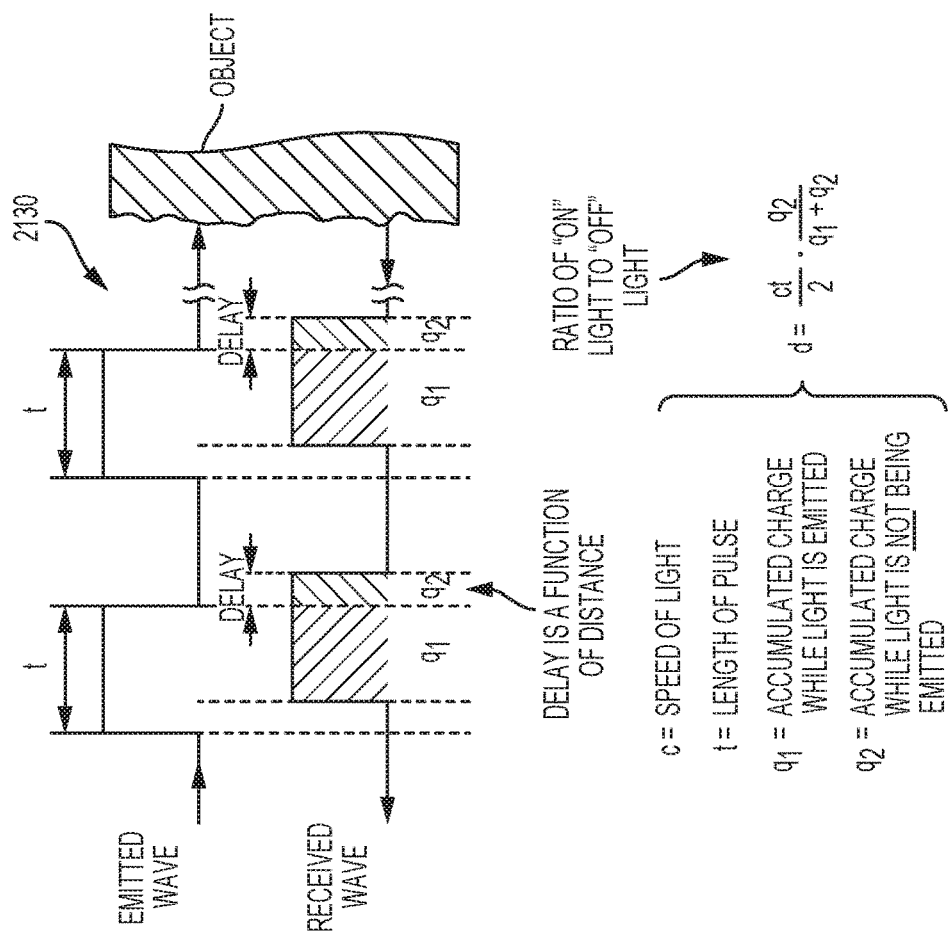

FIG. 42 is a schematic of an emitted wave, a received wave, and a delay between the emitted wave and the received wave of the NIR time-of-flight measurement system of FIG. 41, according to at least one aspect of the present disclosure.

Figure 43:
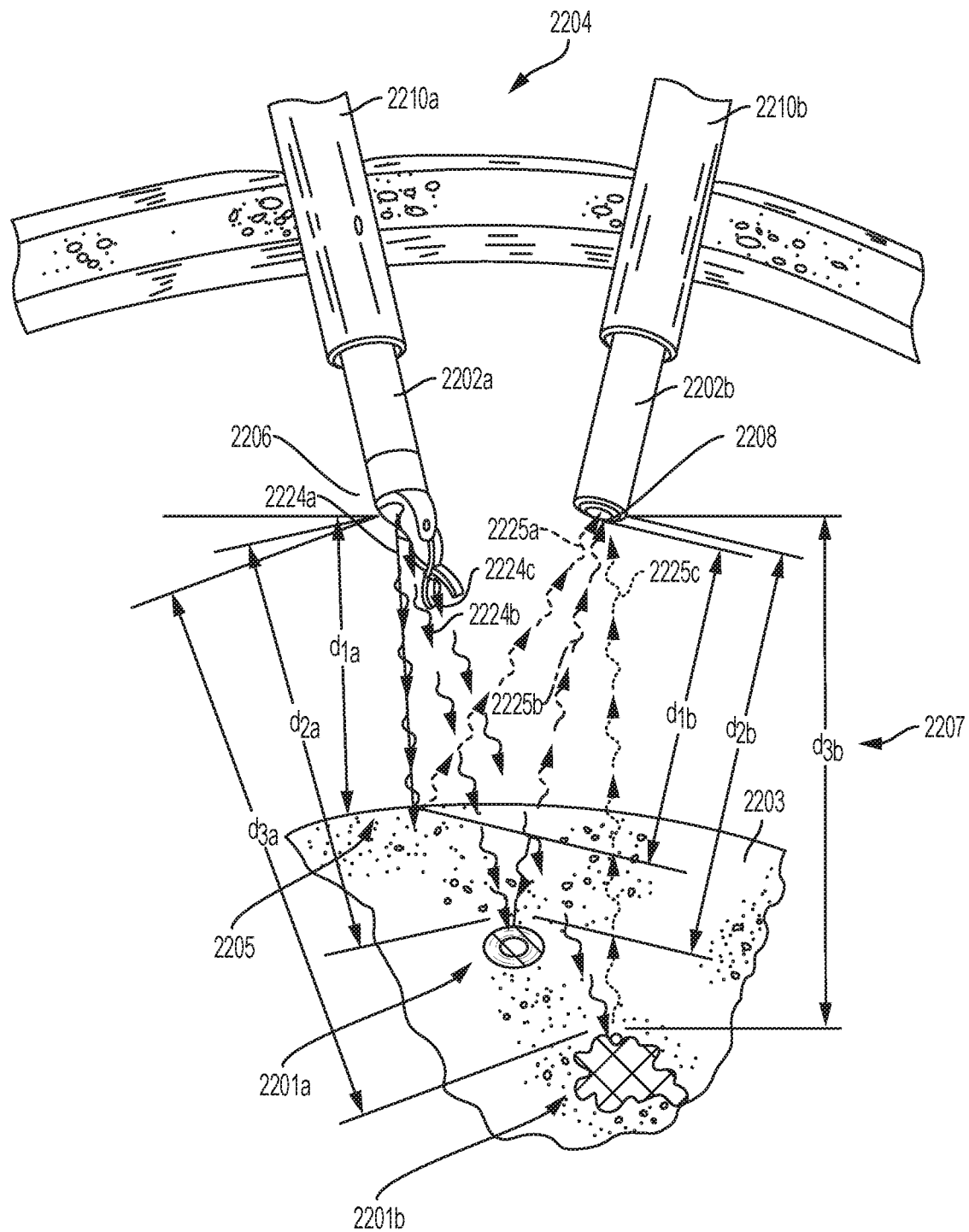

FIG. 43 illustrates a NIR time-of-flight measurement system configured to sense a distance to different structures, the time-of-flight measurement system including a transmitter (emitter) and a receiver (sensor) on separate devices, according to at least one aspect of the present disclosure.

Figure 44:
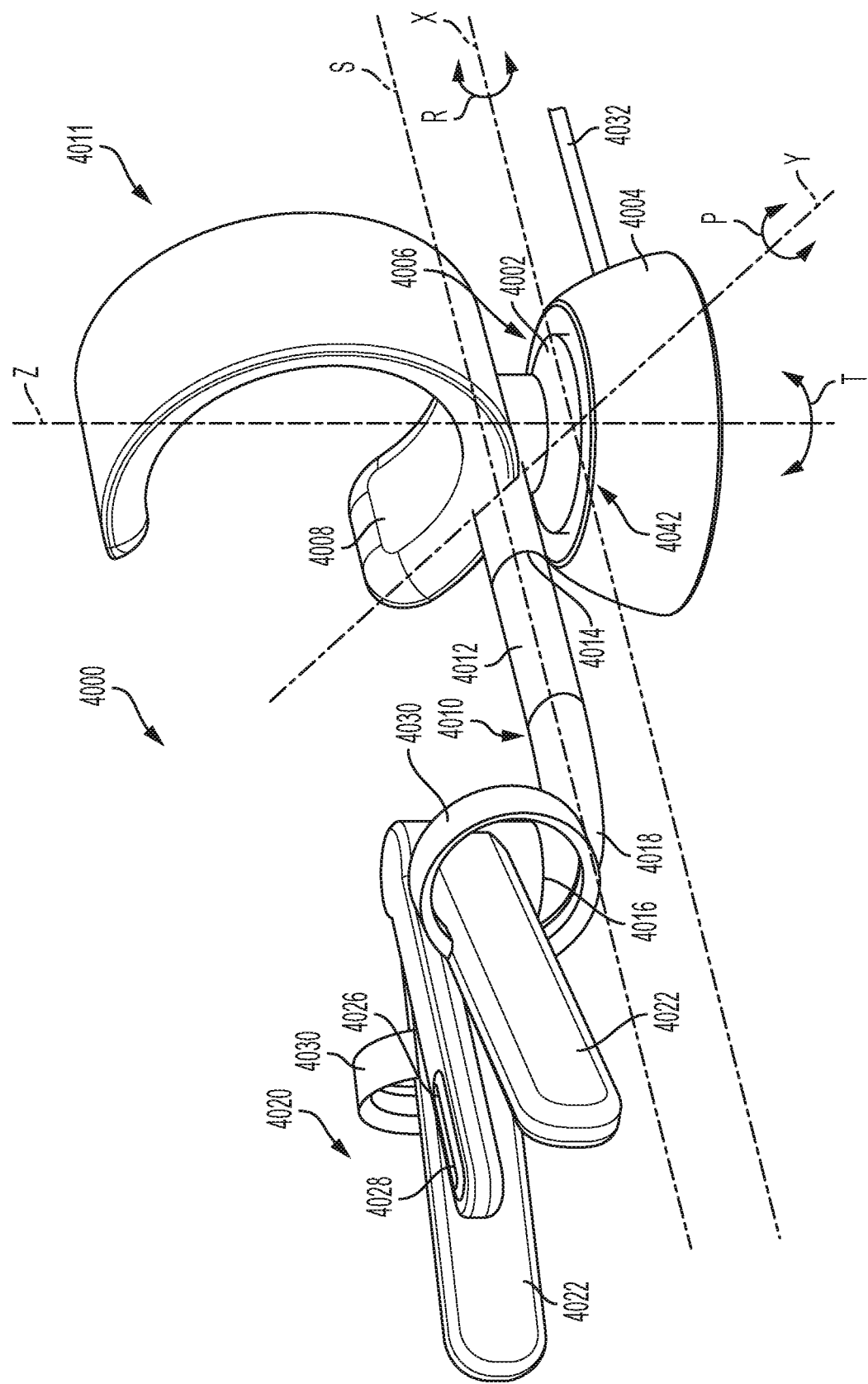

FIG. 44 is a perspective view of an input control device for a robotic surgical system, according to at least one aspect of the present disclosure.

Figure 45:
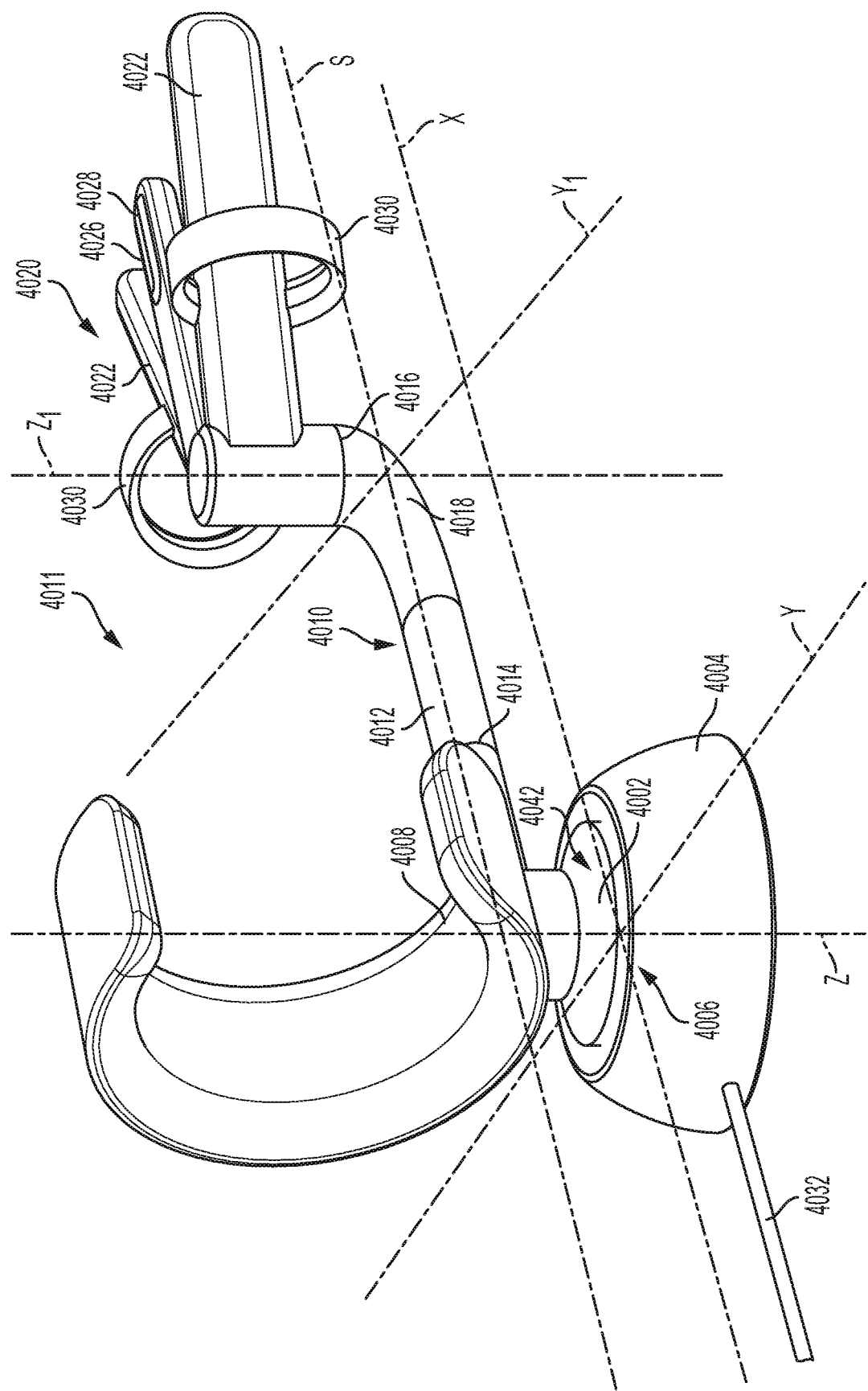

FIG. 45 is another perspective view of the input control device of FIG. 44, according to at least one aspect of the present disclosure.

Figure 46:
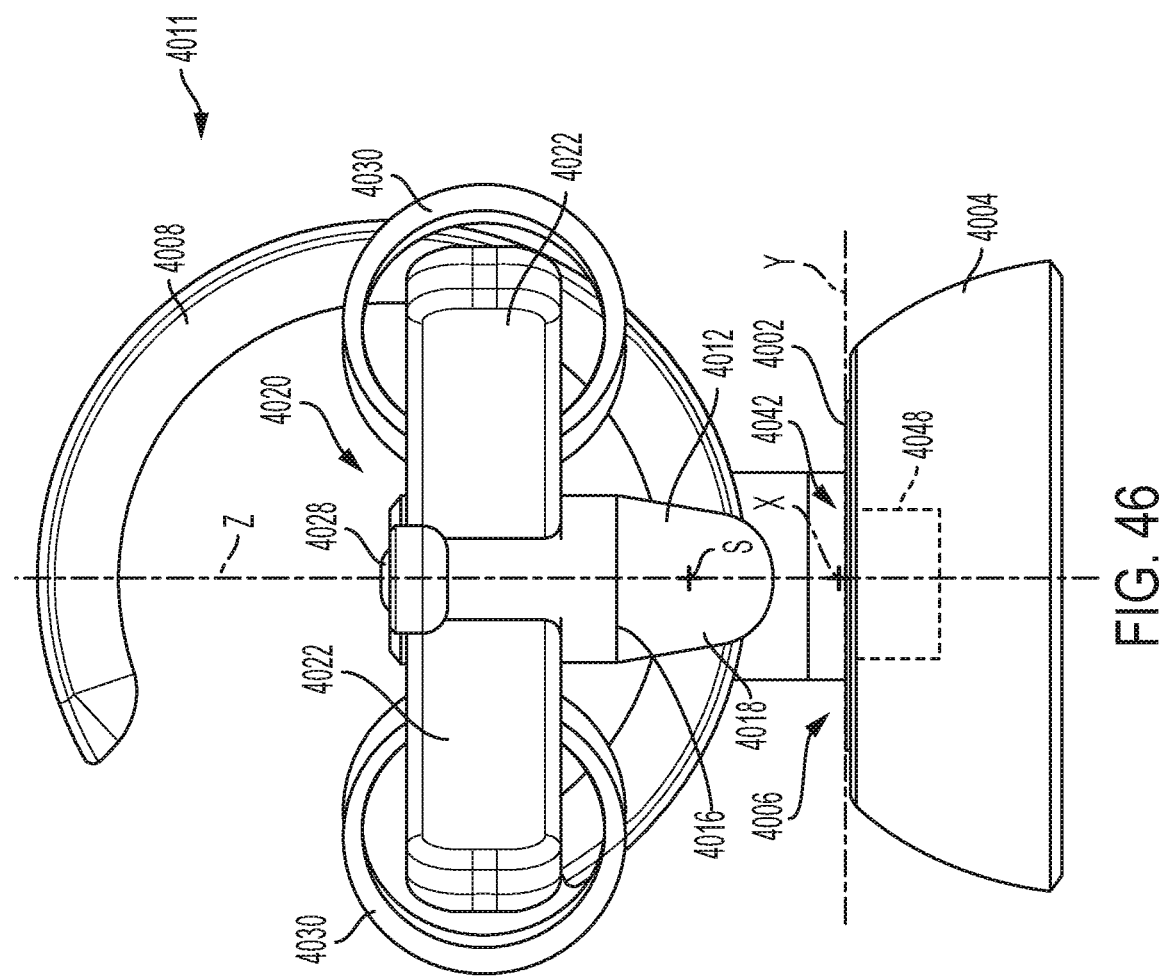

FIG. 46 is a front elevation view of the input control device of FIG. 44, according to at least one aspect of the present disclosure.

Figure 47:
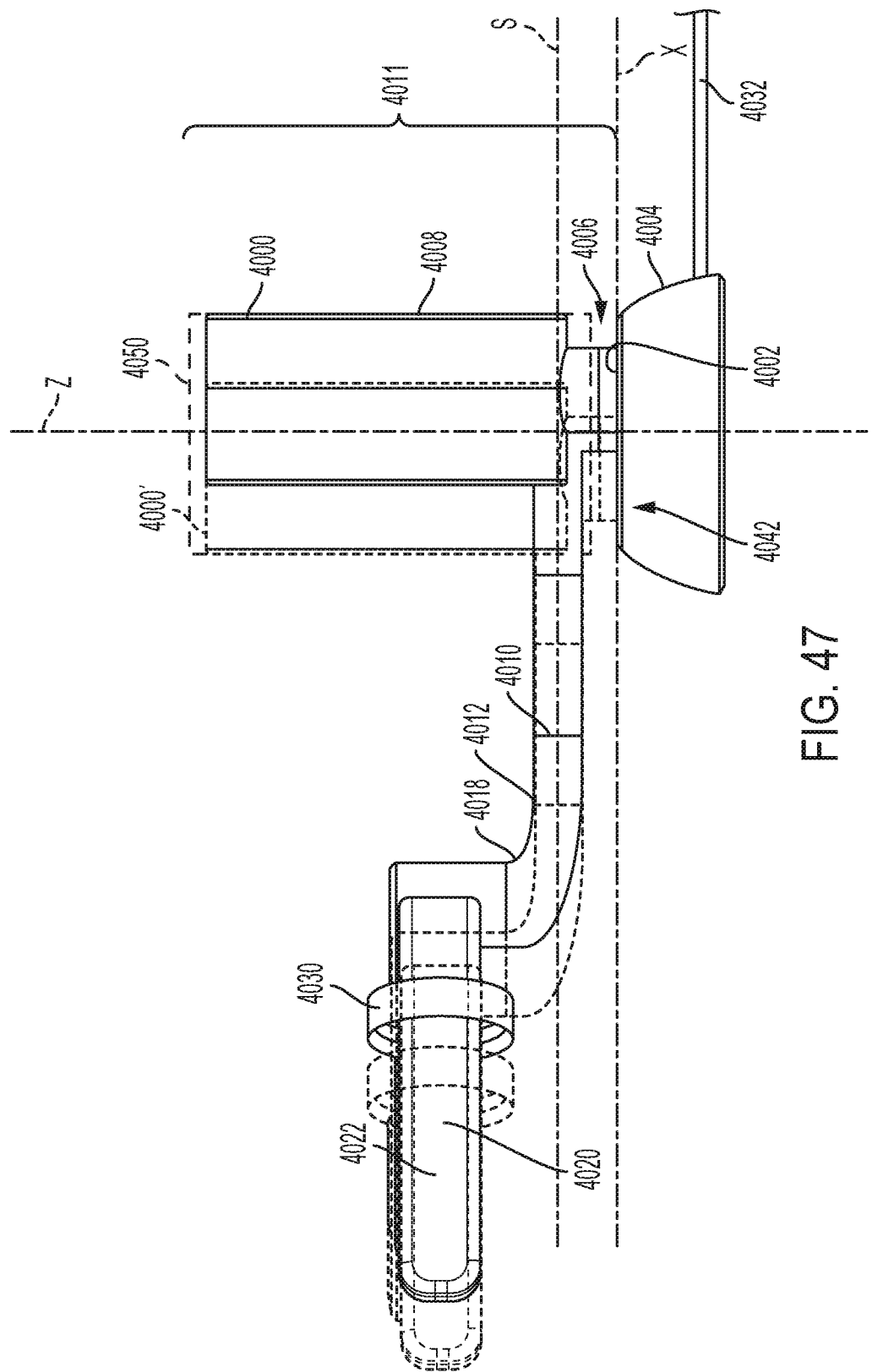

FIG. 47 is a side elevation view of the input control device of FIG. 44 in a first configuration illustrated with solid lines and further depicting the input control device in a second configuration illustrated with dashed lines, wherein a lower portion, or base, of the input control device remains stationary and an upper portion of the input control device is displaced along a longitudinal axis between the first configuration and the second configuration, according to at least one aspect of the present disclosure.

Figure 48:
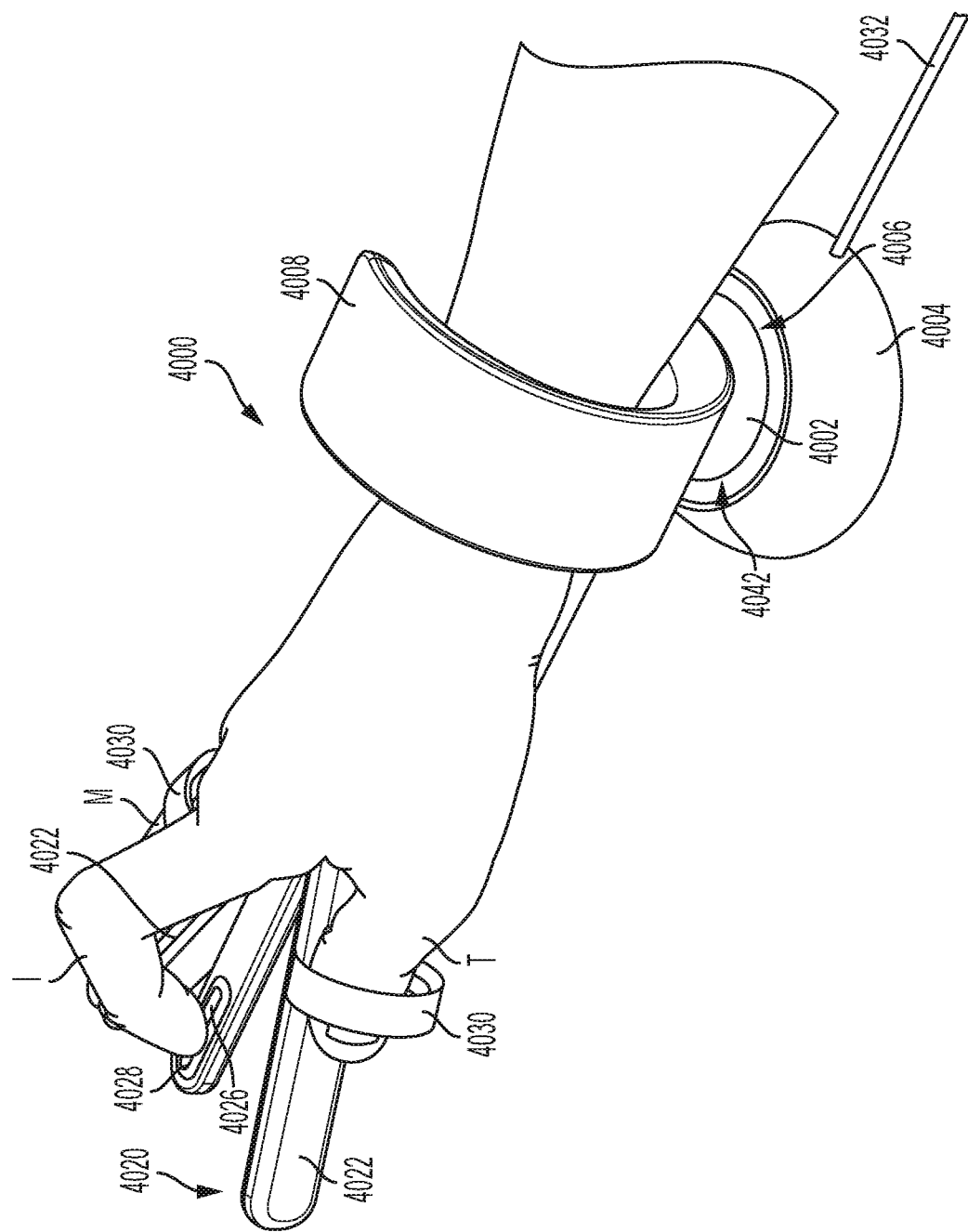

FIG. 48 is a perspective view of a user's hand and forearm engaged with the input control device of FIG. 44, according to at least one aspect of the present disclosure.

Figure 49:
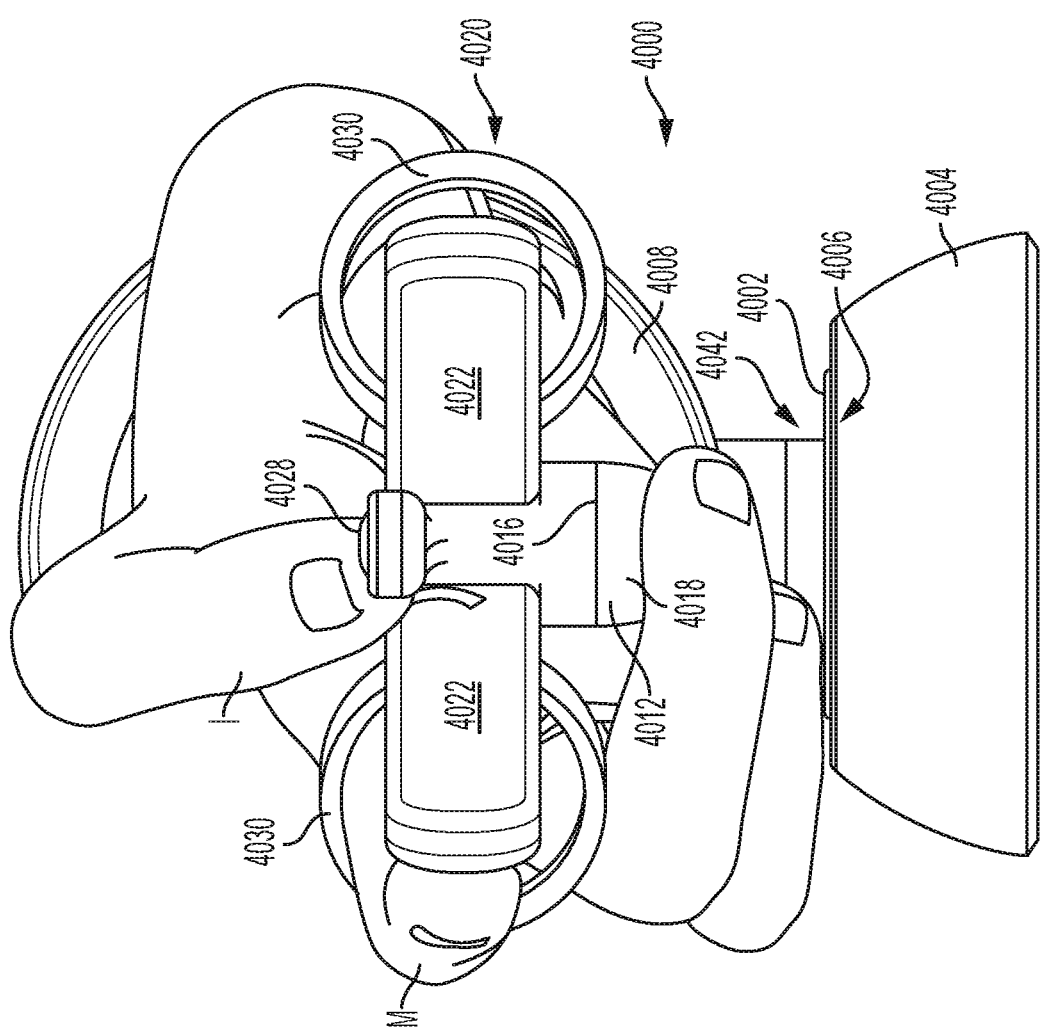

FIG. 49 is a front elevation view of a user's hand and forearm engaged with the input control device of FIG. 44, according to at least one aspect of the present disclosure.

Figure 50:
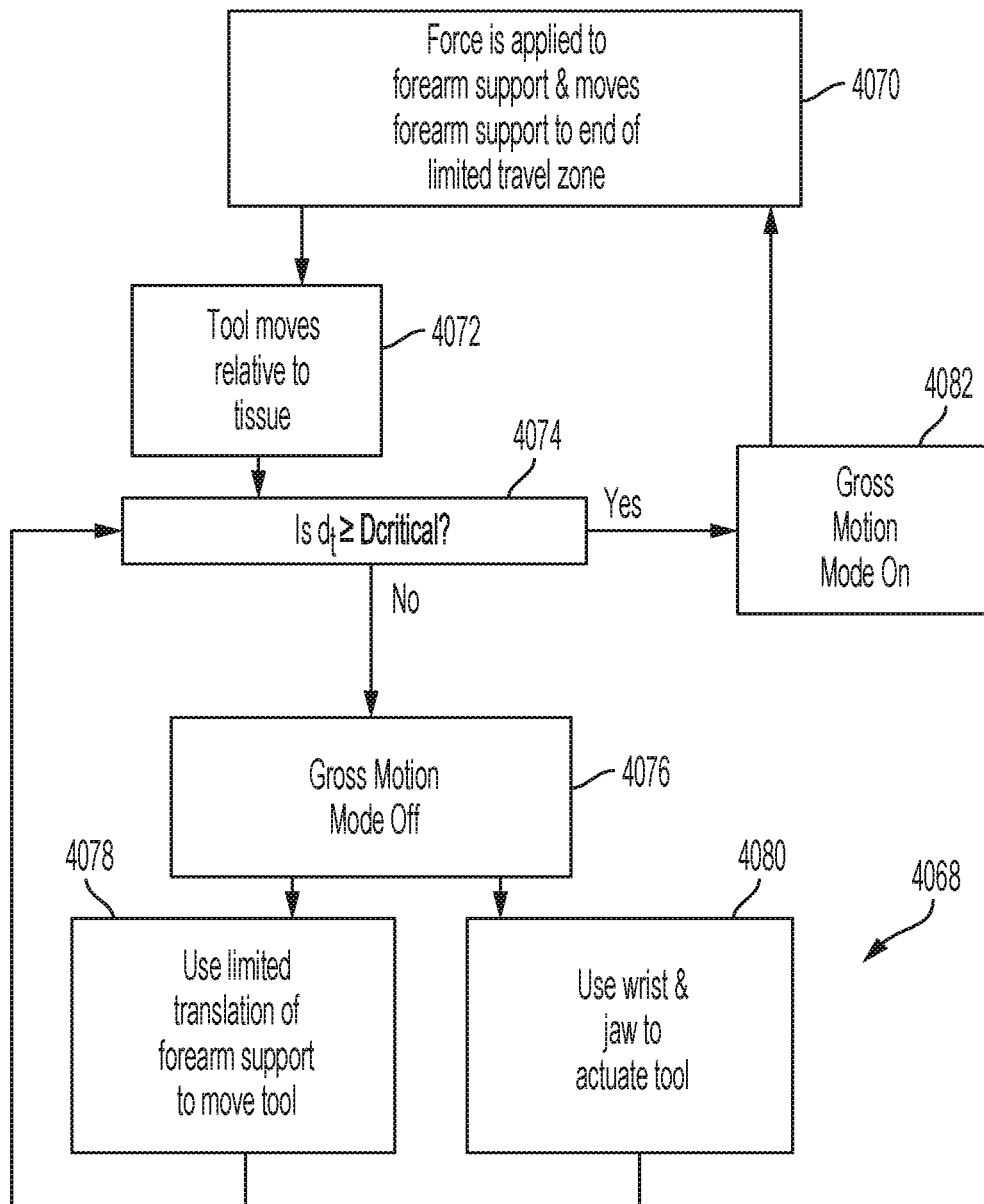

FIG. 50 is a logic diagram for a control circuit utilized in connection with the input control device of FIG. 44, according to at least one aspect of the present disclosure.

Figure 51:
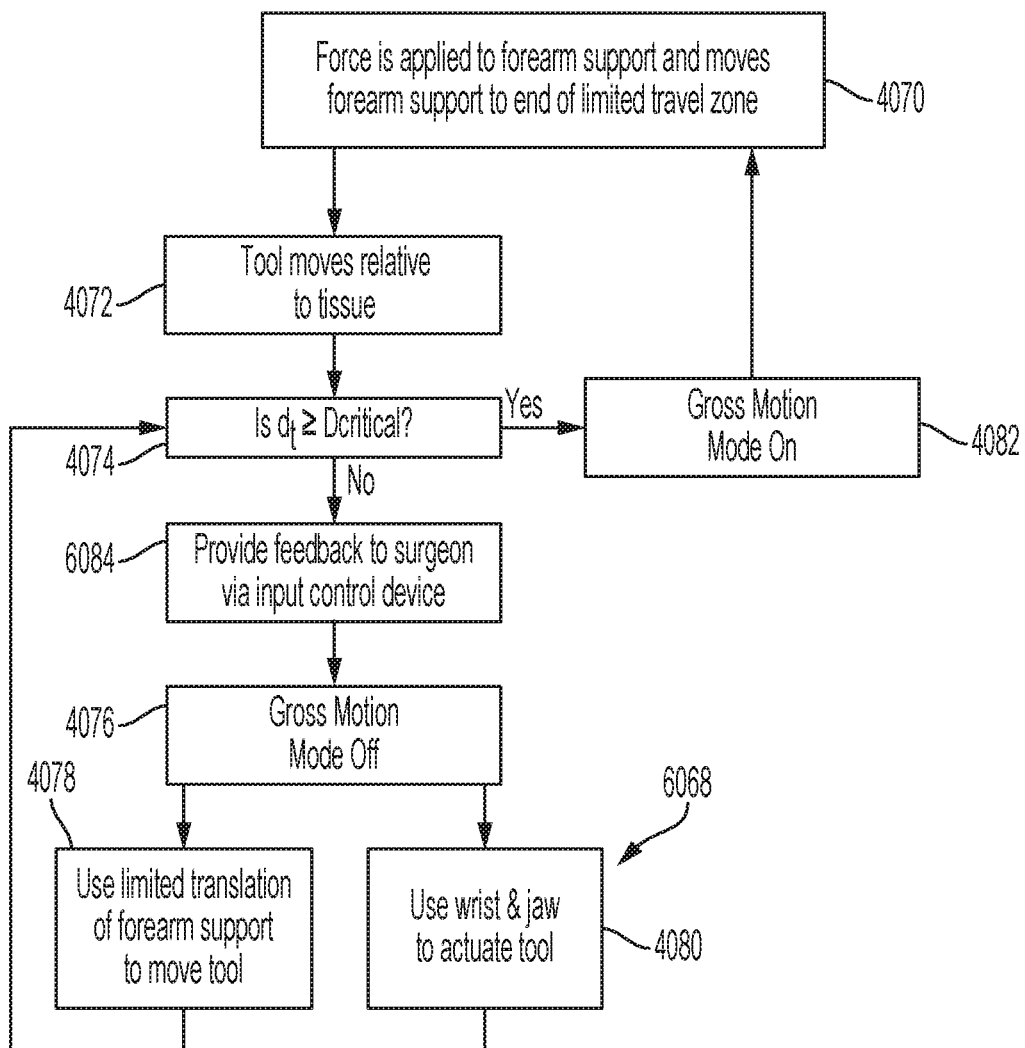

FIG. 51 is a logic diagram for a control circuit utilized in connection with the input control device of FIG. 44, according to at least one aspect of the present disclosure.

Figure 52:
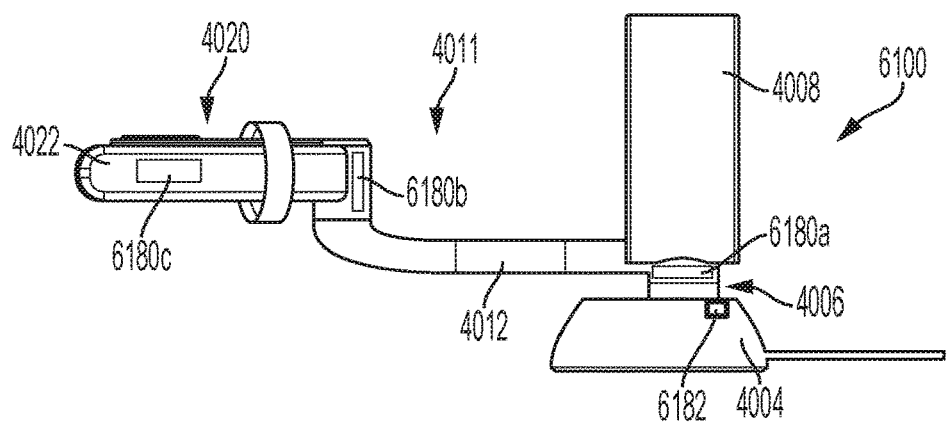

FIG. 52 is a side elevation view of an input control device including feedback generators, according to at least one aspect of the present disclosure.

Figure 53:
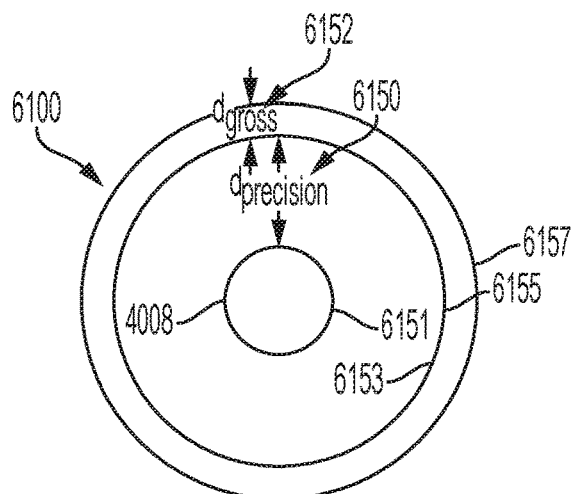

FIG. 53 is a plan view of travel zones for the input control device of FIG. 52, according to at least one aspect of the present disclosure.

Figure 54:
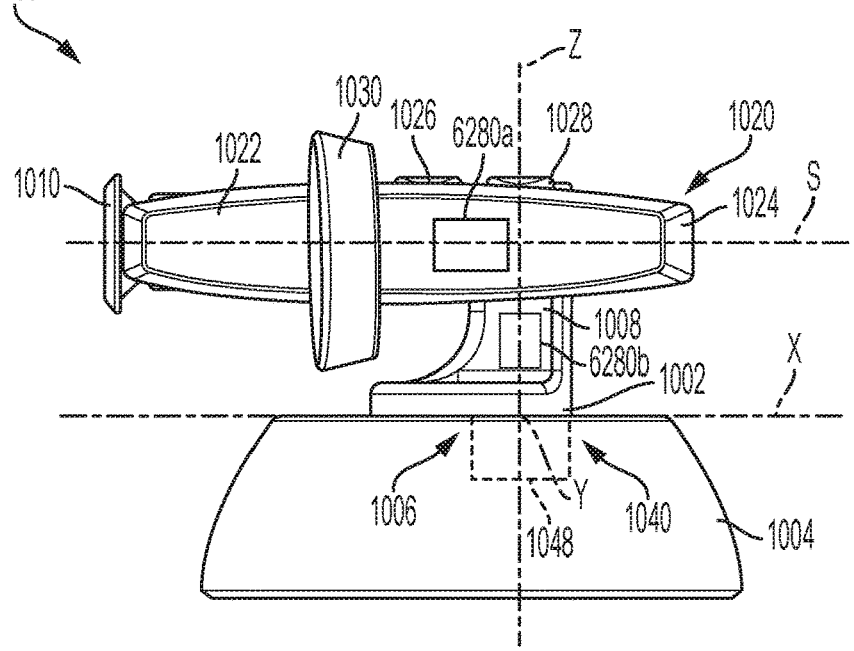

FIG. 54 is a side elevation view of an input control device including feedback generators, according to at least one aspect of the present disclosure.

Figure 55:
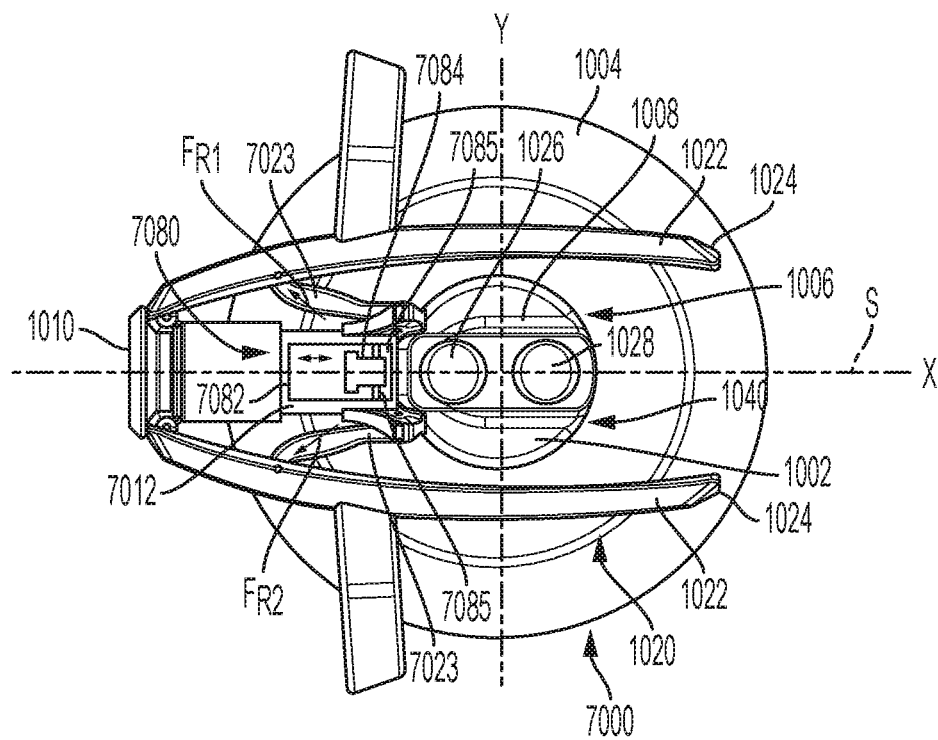

FIG. 55 is a plan view of an input control device including a variable resistance assembly, according to at least one aspect of the present disclosure.

Figure 56:
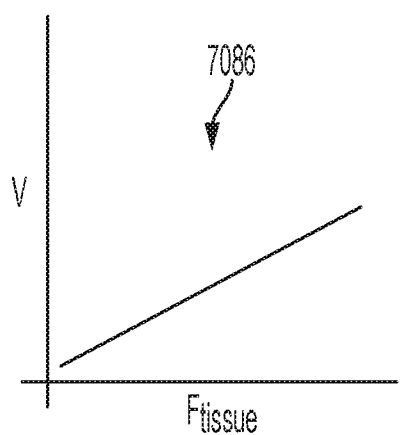

FIG. 56 is a graphical representation of voltage (V) over tissue force ($F_{tissue}$) for the variable resistance assembly of FIG. 55, according to at least one aspect of the present disclosure.

Figure 57:
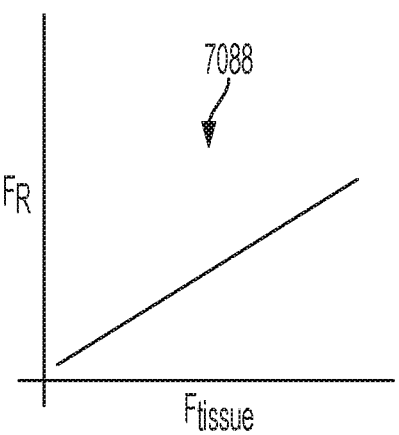

FIG. 57 is a graphical representation of resistance force ( ) over tissue force ( ) for the variable resistance assembly of FIG. 55, according to at least one aspect of the present disclosure.

Figure 58:
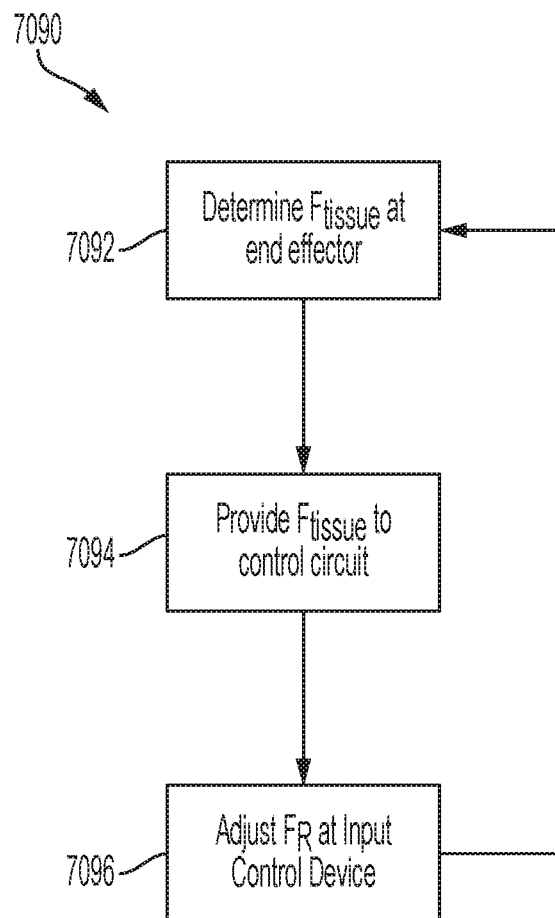

FIG. 58 is a logic diagram for a control circuit utilized in connection with the input control device of FIG. 55, according to at least one aspect of the present disclosure.

Figure 59:
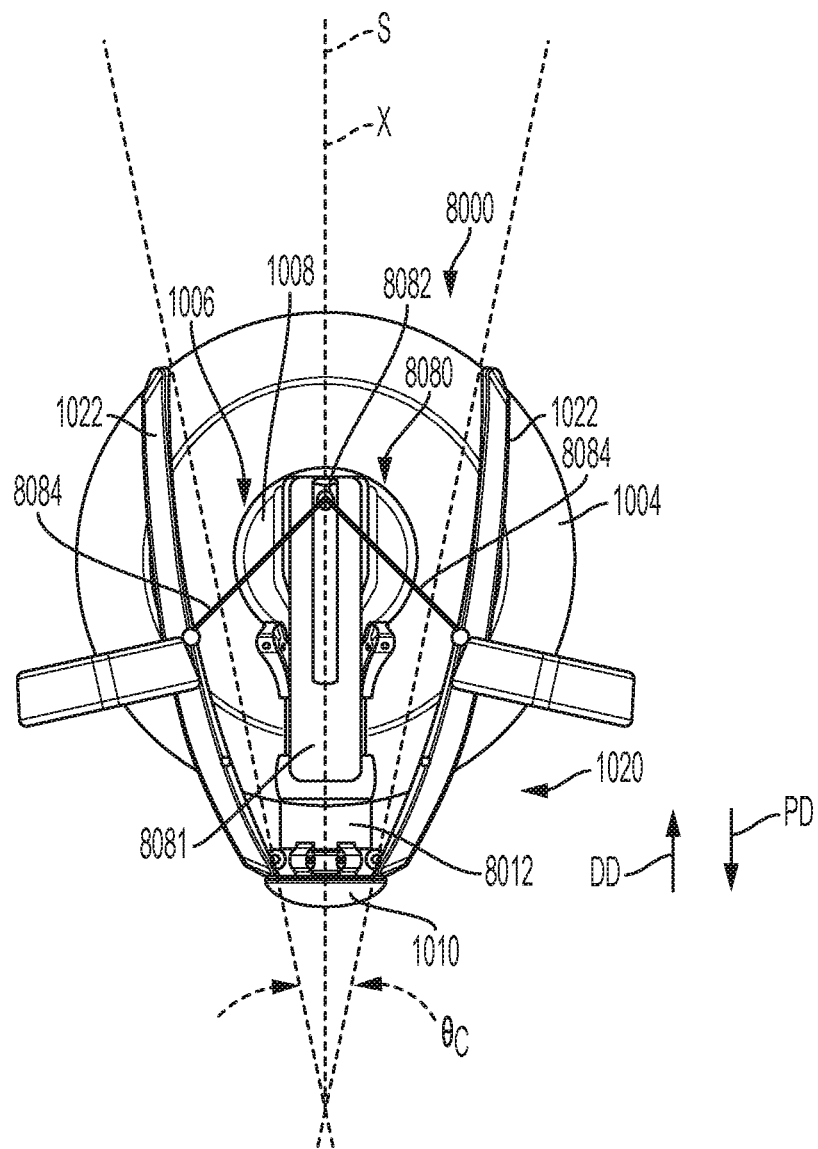

FIG. 59 is a plan view of an input control device including a linear jaw actuator, according to at least one aspect of the present disclosure.

Figure 60:
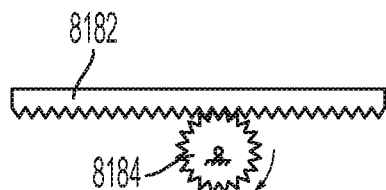

FIG. 60 is an elevation view of a linear jaw actuator for an input control device, according to at least one aspect of the present disclosure.

Figure 61:
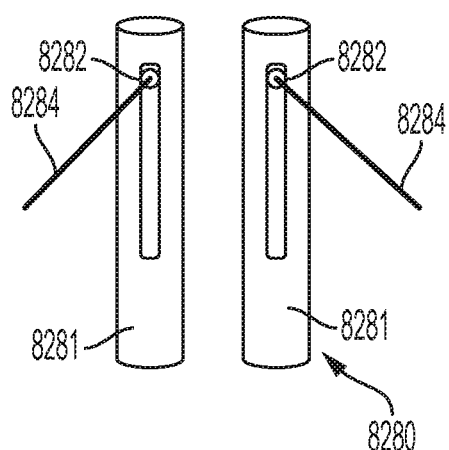

FIG. 61 is a plan view of a pair of linear jaw actuators for an input control device, according to at least one aspect of the present disclosure.

Figure 62:
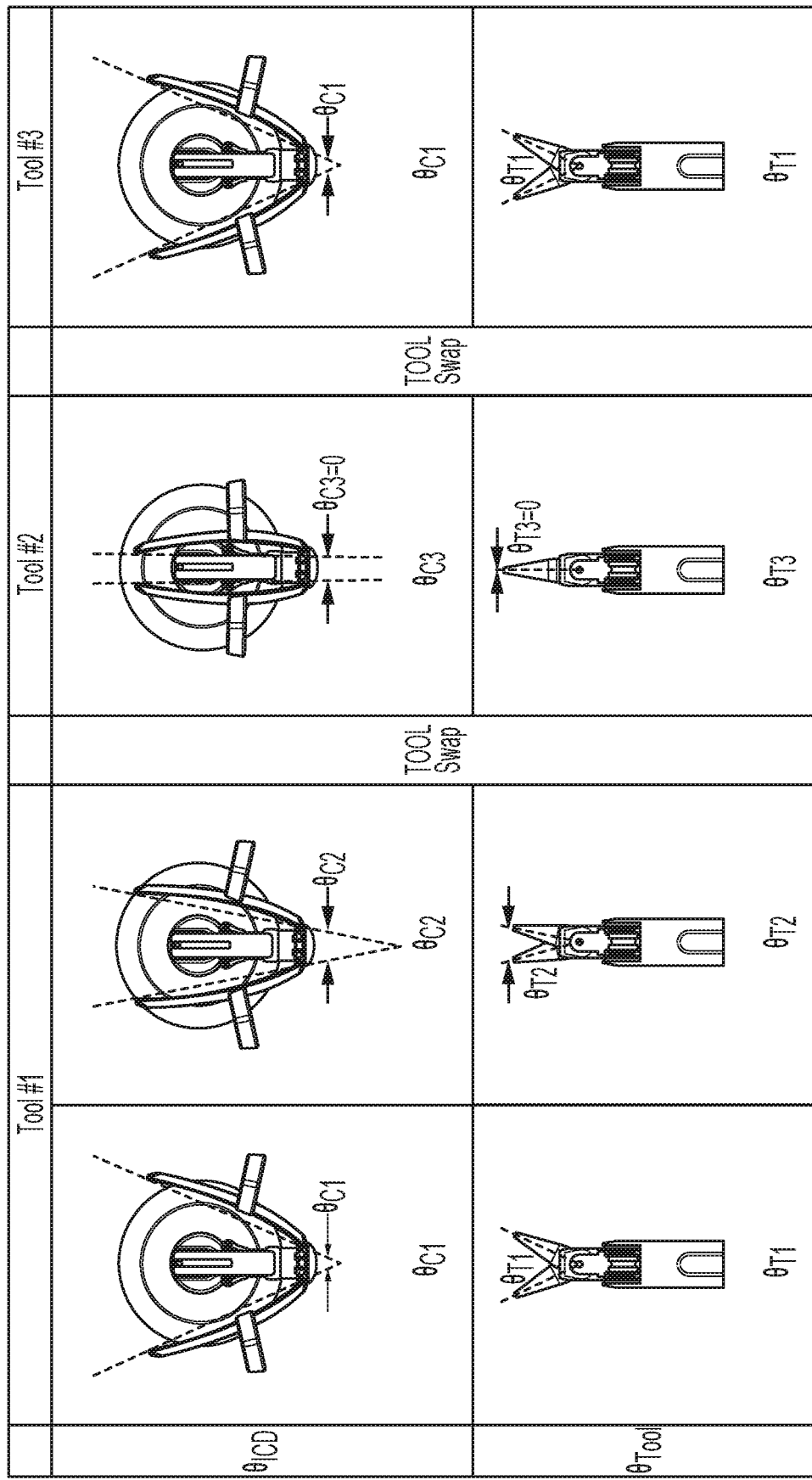

FIG. 62 is a table depicting jaw angles of the input control device of FIG. 59 and jaw angles of various robotic surgical tools throughout a surgical procedure, according to at least one aspect of the present disclosure.

Figure 63:
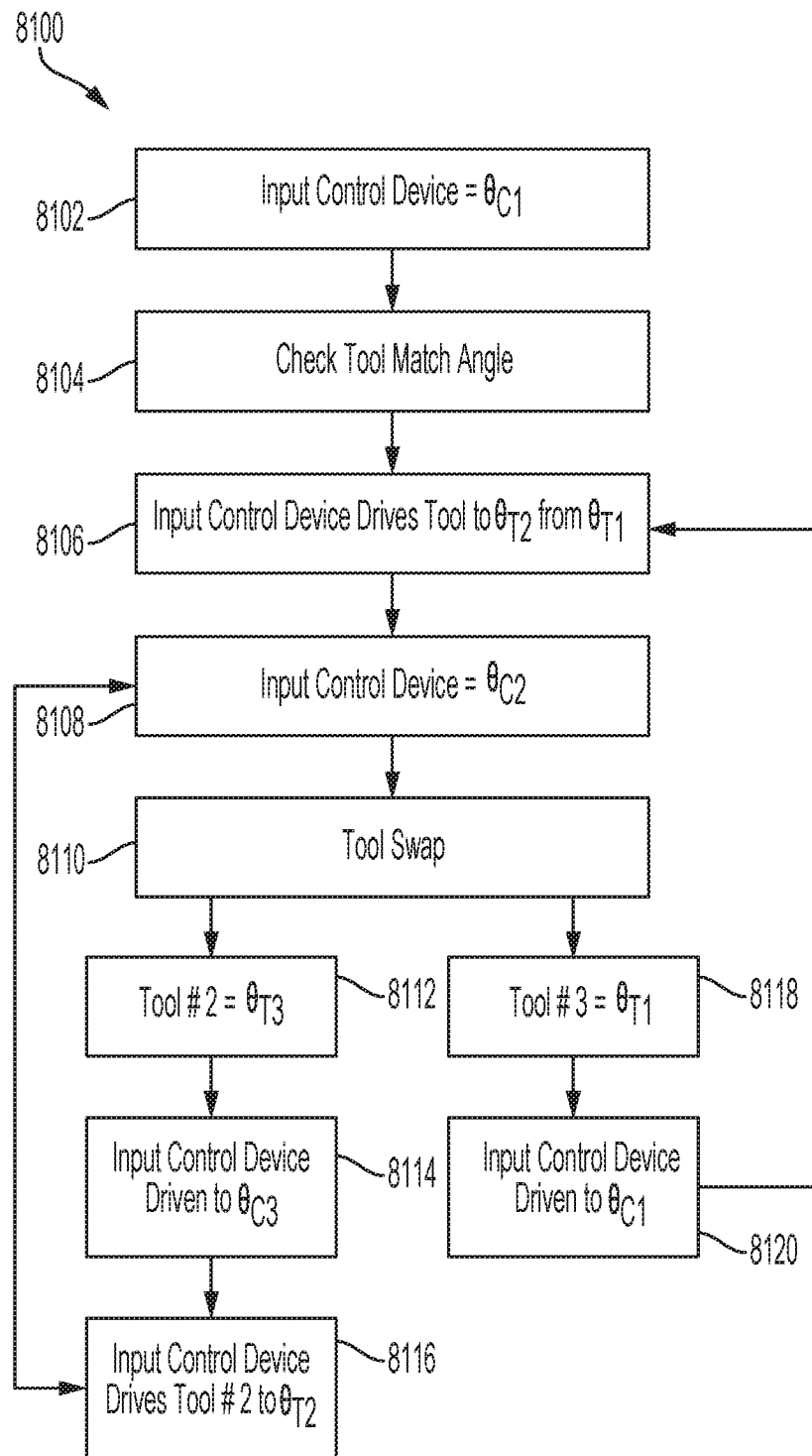

FIG. 63 is a logic diagram for a control circuit utilized in connection with the input control device of FIG. 59, according to at least one aspect of the present disclosure.

DESCRIPTION

Applicant of the present application owns the following U.S. Patent Applications, filed on Mar. 15, 2019, each of which is herein incorporated by reference in its entirety:

U.S. patent application Ser. No. 16/354,417, titled INPUT CONTROLS FOR ROBOTIC SURGERY, now U.S. Patent Application Publication No. 2020/0289219;

U.S. patent application Ser. No. 16/354,420, titled DUAL MODE CONTROLS FOR ROBOTIC SURGERY, now U.S. Patent Application Publication No. 2020/0289228;

U.S. patent application Ser. No. 16/354,422, titled MOTION CAPTURE CONTROLS FOR ROBOTIC SURGERY, now U.S. Patent Application Publication No. 2020/0289216;

U.S. patent application Ser. No. 16/354,440, titled ROBOTIC SURGICAL SYSTEMS WITH MECHANISMS FOR SCALING SURGICAL TOOL MOTION ACCORDING TO TISSUE PROXIMITY, now U.S. Patent Application Publication No. 2020/0289220;

U.S. patent application Ser. No. 16/354,444, titled ROBOTIC SURGICAL SYSTEMS WITH MECHANISMS FOR SCALING CAMERA MAGNIFICATION ACCORDING TO PROXIMITY OF SURGICAL TOOL TO TISSUE, now U.S. Patent Application Publication No. 2020/0289205;

U.S. patent application Ser. No. 16/354,454, titled ROBOTIC SURGICAL SYSTEMS WITH SELECTIVELY LOCKABLE END EFFECTORS, now U.S. Patent Application Publication No. 2020/0289221;

U.S. patent application Ser. No. 16/354,461, titled SELECTABLE VARIABLE RESPONSE OF SHAFT MOTION OF SURGICAL ROBOTIC SYSTEMS, now U.S. Patent Application Publication No. 2020/0289222;

U.S. patent application Ser. No. 16/354,470, titled SEGMENTED CONTROL INPUTS FOR SURGICAL ROBOTIC SYSTEMS, now U.S. Patent Application Publication No. 2020/0289223;

U.S. patent application Ser. No. 16/354,474, titled ROBOTIC SURGICAL CONTROLS HAVING FEEDBACK CAPABILITIES, now U.S. Patent Application Publication No. 2020/0289229; and U.S. patent application Ser. No. 16/354,481, titled JAW COORDINATION OF ROBOTIC SURGICAL CONTROLS, now U.S. Patent Application Publication No. 2020/0289217.

Applicant of the present application also owns the following U.S. Patent Applications, filed on Sep. 11, 2018, each of which is herein incorporated by reference in its entirety:

U.S. patent application Ser. No. 16/128,179, titled SURGICAL VISUALIZATION PLATFORM;

U.S. patent application Ser. No. 16/128,180, titled CONTROLLING AN EMITTER ASSEMBLY PULSE SEQUENCE;

U.S. patent application Ser. No. 16/128,198, titled SINGULAR EMR SOURCE EMITTER ASSEMBLY;

U.S. patent application Ser. No. 16/128,207, titled COMBINATION EMITTER AND CAMERA ASSEMBLY;

U.S. patent application Ser. No. 16/128,176, titled SURGICAL VISUALIZATION WITH PROXIMITY TRACKING FEATURES;

U.S. patent application Ser. No. 16/128,187, titled SURGICAL VISUALIZATION OF MULTIPLE TARGETS;

U.S. patent application Ser. No. 16/128,192, titled VISUALIZATION OF SURGICAL DEVICES;

U.S. patent application Ser. No. 16/128,163, titled OPERATIVE COMMUNICATION OF LIGHT;

U.S. patent application Ser. No. 16/128,197, titled ROBOTIC LIGHT PROJECTION TOOLS;

U.S. patent application Ser. No. 16/128,164, titled SURGICAL VISUALIZATION FEEDBACK SYSTEM;

U.S. patent application Ser. No. 16/128,193, titled SURGICAL VISUALIZATION AND MONITORING;

U.S. patent application Ser. No. 16/128,195, titled INTEGRATION OF IMAGING DATA;

U.S. patent application Ser. No. 16/128,170, titled ROBOTICALLY-ASSISTED SURGICAL SUTURING SYSTEMS;

U.S. patent application Ser. No. 16/128,183, titled SAFETY LOGIC FOR SURGICAL SUTURING SYSTEMS;

U.S. patent application Ser. No. 16/128,172, titled ROBOTIC SYSTEM WITH SEPARATE PHOTOACOUSTIC RECEIVERS; and U.S. patent application Ser. No. 16/128,185, titled FORCE SENSOR THROUGH STRUCTURED LIGHT DEFLECTION.

Applicant of the present application also owns the following U.S. Patent Applications, filed on Mar. 29, 2018, each of which is herein incorporated by reference in its entirety:

U.S. patent application Ser. No. 15/940,627, titled DRIVE ARRANGEMENTS FOR ROBOT-ASSISTED SURGICAL PLATFORMS;

U.S. patent application Ser. No. 15/940,676, titled AUTOMATIC TOOL ADJUSTMENTS FOR ROBOT-ASSISTED SURGICAL PLATFORMS;

U.S. patent application Ser. No. 15/940,711, titled SENSING ARRANGEMENTS FOR ROBOT-ASSISTED SURGICAL PLATFORMS; and U.S. patent application Ser. No. 15/940,722, titled CHARACTERIZATION OF TISSUE IRREGULARITIES THROUGH THE USE OF MONO-CHROMATIC LIGHT REFRACTIVITY.

Before explaining various aspects of a robotic surgical platform in detail, it should be noted that the illustrative examples are not limited in application or use to the details of construction and arrangement of parts illustrated in the accompanying drawings and description. The illustrative examples may be implemented or incorporated in other aspects, variations, and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects, and/or examples.

Robotic Systems

Figure 1:
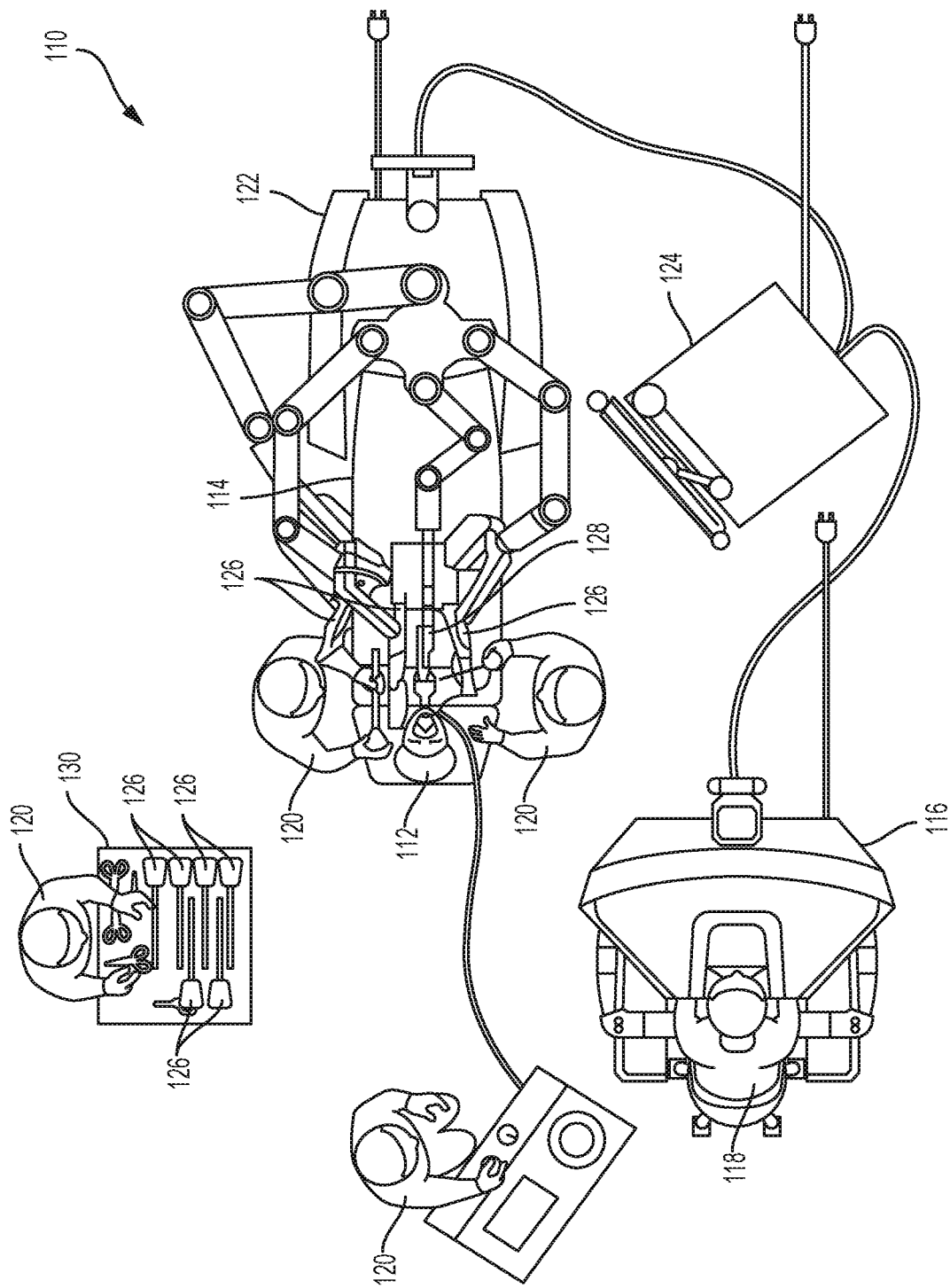
FIG. 1 is a plan view of a robotic surgical system being used to perform a surgery, according to at least one aspect of the present disclosure.

An exemplary robotic system 110 is depicted in FIG. 1. The robotic system 110 is a minimally invasive robotic surgical (MIRS) system typically used for performing a minimally invasive diagnostic or surgical procedure on a patient 112 who is lying down on an operating table 114. The robotic system 110 includes a surgeon's console 116 for use by a surgeon 118 during the procedure. One or more assistants 120 may also participate in the procedure. The robotic system 110 can further include a patient side cart 122, i.e. a surgical robot, and an electronics cart 124. The surgical robot 122 can manipulate at least one removably coupled tool assembly 126 (hereinafter referred to as a "tool") through a minimally invasive incision in the body of the patient 112 while the surgeon 118 views the surgical site through the console 116. An image of the surgical site can be obtained by an imaging device such as a stereoscopic endoscope 128, which can be manipulated by the surgical robot 122 to orient the endoscope 128. Alternative imaging devices are also contemplated.

The electronics cart 124 can be used to process the images of the surgical site for subsequent display to the surgeon 118 through the surgeon's console 116. In certain instances, the electronics of the electronics cart 124 can be incorporated into another structure in the operating room, such as the operating table 114, the surgical robot 122, the surgeon's console 116, and/or another control station, for example. The number of robotic tools 126 used at one time will generally depend on the diagnostic or surgical procedure and the space constraints within the operating room among other factors. If it is necessary to change one or more of the robotic tools 126 being used during a procedure, an assistant 120 may remove the robotic tool 126 from the surgical robot 122 and replace it with another tool 126 from a tray 130 in the operating room.

Figure 2:
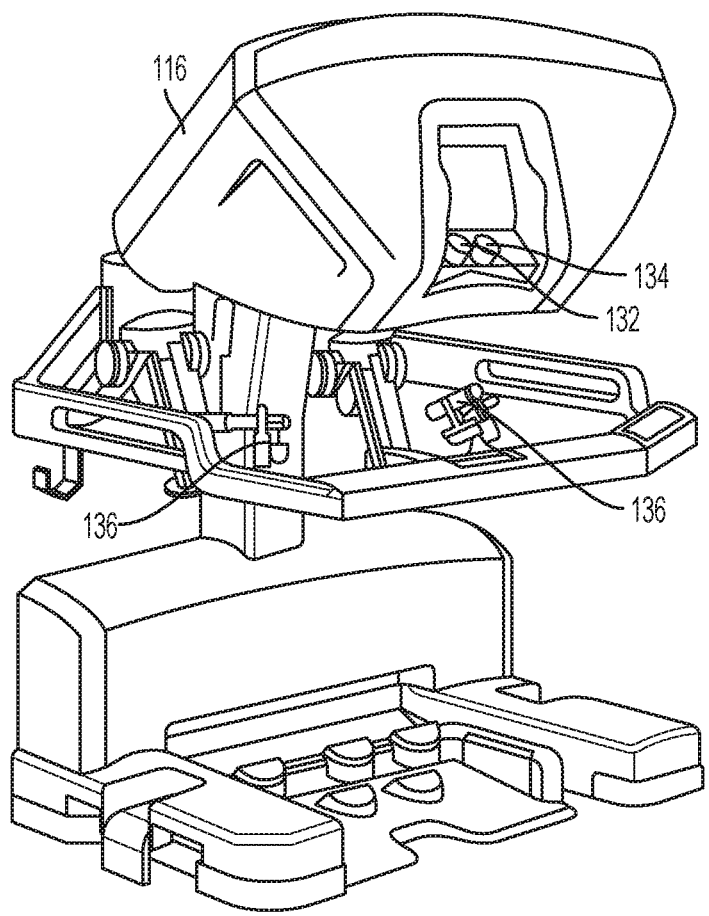
FIG. 2 is a perspective view of a surgeon's control console of the robotic surgical system of FIG. 1, according to at least one aspect of the present disclosure.

Referring primarily to FIG. 2, the surgeon's console 116 includes a left eye display 132 and a right eye display 134 for presenting the surgeon 118 with a coordinated stereo view of the surgical site that enables depth perception. The console 116 further includes one or more input control devices 136, which in turn cause the surgical robot 122 to manipulate one or more tools 126. The input control devices 136 can provide the same degrees of freedom as their associated tools 126 to provide the surgeon with telepresence, or the perception that the input control devices 136 are integral with the robotic tools 126 so that the surgeon has a strong sense of directly controlling the robotic tools 126. To this end, position, force, and tactile feedback sensors may be employed to transmit position, force, and tactile sensations from the robotic tools 126 back to the surgeon's hands through the input control devices 136. The surgeon's console 116 can be located in the same room as the patient 112 so that the surgeon 118 may directly monitor the procedure, be physically present if necessary, and speak to an assistant 120 directly rather than over the telephone or other communication medium. However, the surgeon 118 can be located in a different room, a completely different building, or other remote location from the patient 112 allowing for remote surgical procedures. A sterile field can be defined around the surgical site. In various instances, the surgeon 118 can be positioned outside the sterile field.

Referring again to FIG. 1, the electronics cart 124 can be coupled with the endoscope 128 and can include a processor to process captured images for subsequent display, such as to a surgeon on the surgeon's console 116, or on another suitable display located locally and/or remotely. For example, when the stereoscopic endoscope 128 is used, the electronics cart 124 can process the captured images to present the surgeon with coordinated stereo images of the surgical site. Such coordination can include alignment between the opposing images and can include adjusting the stereo working distance of the stereoscopic endoscope. As another example, image processing can include the use of previously-determined camera calibration parameters to compensate for imaging errors of the image capture device, such as optical aberrations, for example. In various instances, the robotic system 110 can incorporate a surgical visualization system, as further described herein, such that an augmented view of the surgical site that includes hidden critical structures, three-dimensional topography, and/or one or more distances can be conveyed to the surgeon at the surgeon's console 116.

Figure 3:
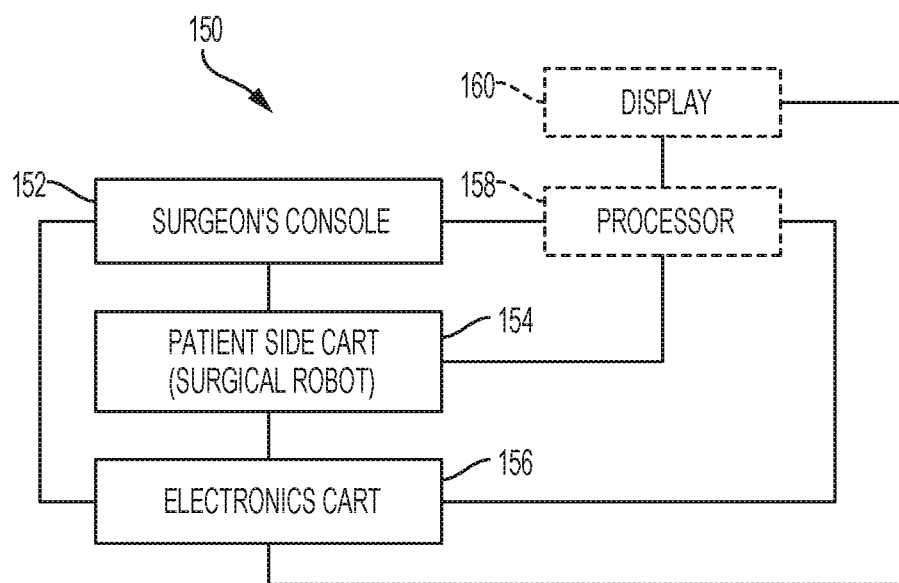
FIG. 3 is a diagram of a robotic surgical system, according to at least one aspect of the present disclosure.

FIG. 3 diagrammatically illustrates a robotic surgery system 150, such as the MIRS system 110 (FIG. 1). As discussed herein, a surgeon's console 152, such as the surgeon's console 116 (FIGS. 1 and 2), can be used by a surgeon to control a surgical robot 154, such as the surgical robot 122 (FIG. 1), during a minimally invasive procedure. The surgical robot 154 can use an imaging device, such as a stereoscopic endoscope, for example, to capture images of the surgical site and output the captured images to an electronics cart 156, such as the electronics cart 124 (FIG. 1). As discussed herein, the electronics cart 156 can process the captured images in a variety of ways prior to any subsequent display. For example, the electronics cart 156 can overlay the captured images with a virtual control interface prior to displaying the combined images to the surgeon via the surgeon's console 152. The surgical robot 154 can output the captured images for processing outside the electronics cart 156. For example, the surgical robot 154 can output the captured images to a processor 158, which can be used to process the captured images. The images can also be processed by a combination of the electronics cart 156 and the processor 158, which can be coupled together to process the captured images jointly, sequentially, and/or combinations thereof. One or more separate displays 160 can also be coupled with the processor 158 and/or the electronics cart 156 for local and/or remote display of images, such as images of the surgical site, or other related images.

The reader will appreciate that various robotic tools can be employed with the surgical robot 122 and exemplary robotic tools are described herein. Referring again to FIG. 1, the surgical robot 122 shown provides for the manipulation of three robotic tools 126 and the imaging device 128, such as a stereoscopic endoscope used for the capture of images of the site of the procedure, for example. Manipulation is provided by robotic mechanisms having a number of robotic joints. The imaging device 128 and the robotic tools 126 can be positioned and manipulated through incisions in the patient so that a kinematic remote center or virtual pivot is maintained at the incision to minimize the size of the incision. Images of the surgical site can include images of the distal ends of the robotic tools 126 when they are positioned within the field-of-view (FOV) of the imaging device 128. Each tool 126 is detachable from and carried by a respective surgical manipulator, which is located at the distal end of one or more of the robotic joints. The surgical manipulator provides a moveable platform for moving the entirety of a tool 126 with respect to the surgical robot 122, via movement of the robotic joints. The surgical manipulator also provides power to operate the robotic tool 126 using one or more mechanical and/or electrical interfaces. In various instances, one or more motors can be housed in the surgical manipulator for generating controls motions. One or more transmissions can be employed to selectively couple the motors to various actuation systems in the robotic tool.

The foregoing robotic systems are further described in U.S. patent application Ser. No. 15/940,627, titled DRIVE ARRANGEMENTS FOR ROBOT-ASSISTED SURGICAL PLATFORMS, filed Mar. 29, 2018, which is incorporated by reference herein in its entirety. Alternative robotic systems are also contemplated.

Figure 4:
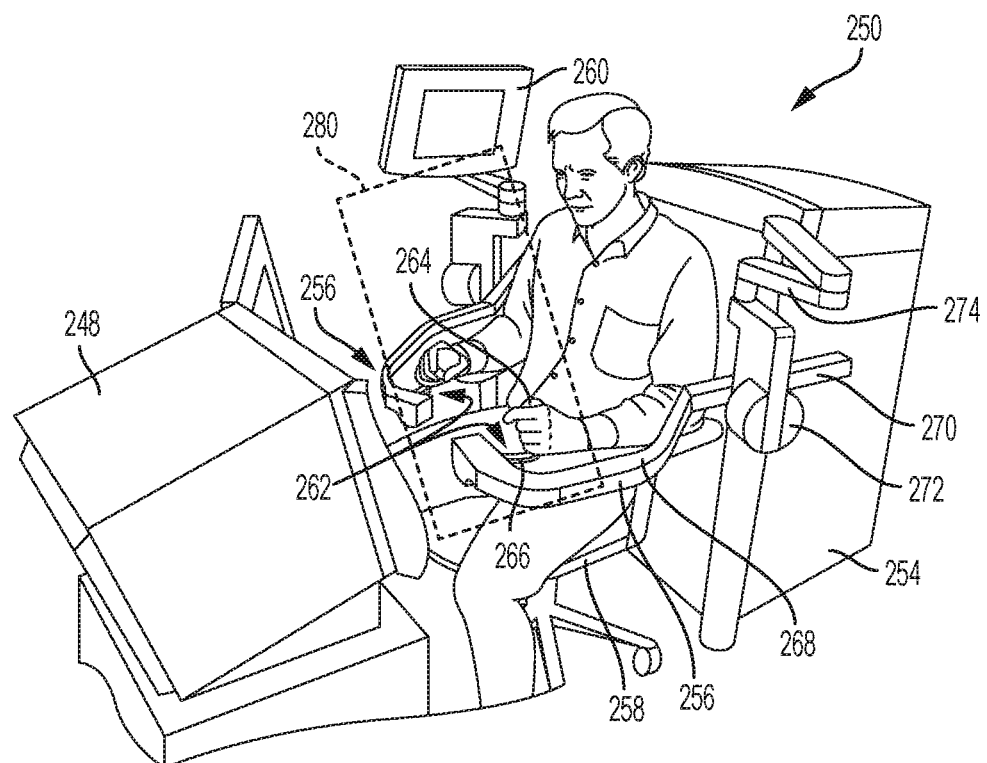
FIG. 4 is a perspective view of a surgeon's control console of a robotic surgical system, according to at least one aspect of the present disclosure.

Referring now to FIG. 4, a surgeon's console, or control unit, 250 is shown. The surgeon's console 250 can be used in connection with a robotic system to control any two surgical tools coupled to the robotic system. The surgical tools can be controlled by the handle assemblies 256 of the surgeon's console 250. For example, the handle assemblies 256 and robotic arms have a master-slave relationship so that movement of the handle assemblies 256 produces a corresponding movement of the surgical tools. A controller 254 receives input signals from the handle assemblies 256, computes a corresponding movement of the surgical tools, and provides output signals to move the robotic arms and the surgical tools.

The handle assemblies 256 are located adjacent to a surgeon's chair 258 and coupled to the controller 254. The controller 254 may include one or more microprocessors, memory devices, drivers, etc. that convert input information from the handle assemblies 256 into output control signals which move the robotic arms and/or actuate the surgical tools. The surgeon's chair 258 and the handle assemblies 256 may be in front of a video console 248, which can be linked to an endoscope to provide video images of the patient. The surgeon's console 250 may also include a screen 260 coupled to the controller 254. The screen 260 may display graphical user interfaces (GUIs) that allow the surgeon to control various functions and parameters of the robotic system.

Each handle assembly 256 includes a handle/wrist assembly 262. The handle/wrist assembly 262 has a handle 264 that is coupled to a wrist 266. The wrist 266 is connected to a forearm linkage 268 that slides along a slide bar 270. The slide bar 270 is pivotally connected to an elbow joint 272. The elbow joint 272 is pivotally connected to a shoulder joint 274 that is attached to the controller 254. The surgeon sitting at the surgeon's console 250 can provide input control motions to the handle assemblies 256 to effect movements and/or actuations of a surgical tool communicatively coupled thereto. For example, the surgeon can advance the forearm linkage 268 along the slide bar 270 to advance the surgical tool toward a surgical site. Rotations at the wrist 266, elbow joint 272, and/or shoulder joint 274 can effect rotation and/or articulation of the surgical tool about the corresponding axes. The robotic system and surgeon's console 250 are further described in U.S. Pat. No. 6,951,535, titled TELE-MEDICINE SYSTEM THAT TRANSMITS AN ENTIRE STATE OF A SUBSYSTEM, which issued Oct. 4, 2005, the entire disclosure of which is incorporated by reference herein.

Figure 5:
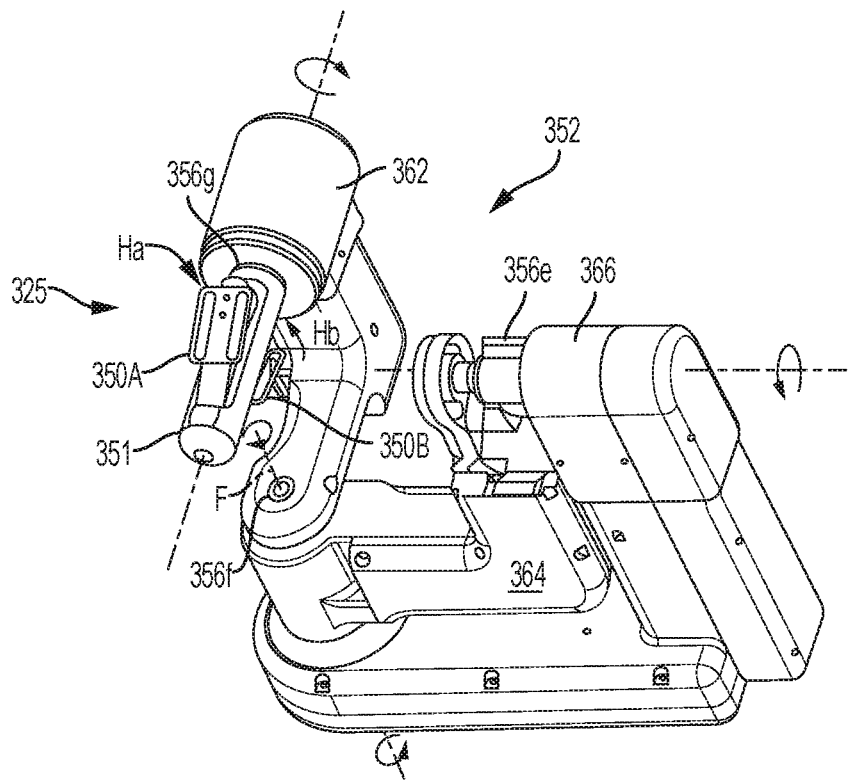
FIG. 5 is a perspective view of a user input device at a surgeon's control console, according to at least one aspect of the present disclosure.
Figure 6:
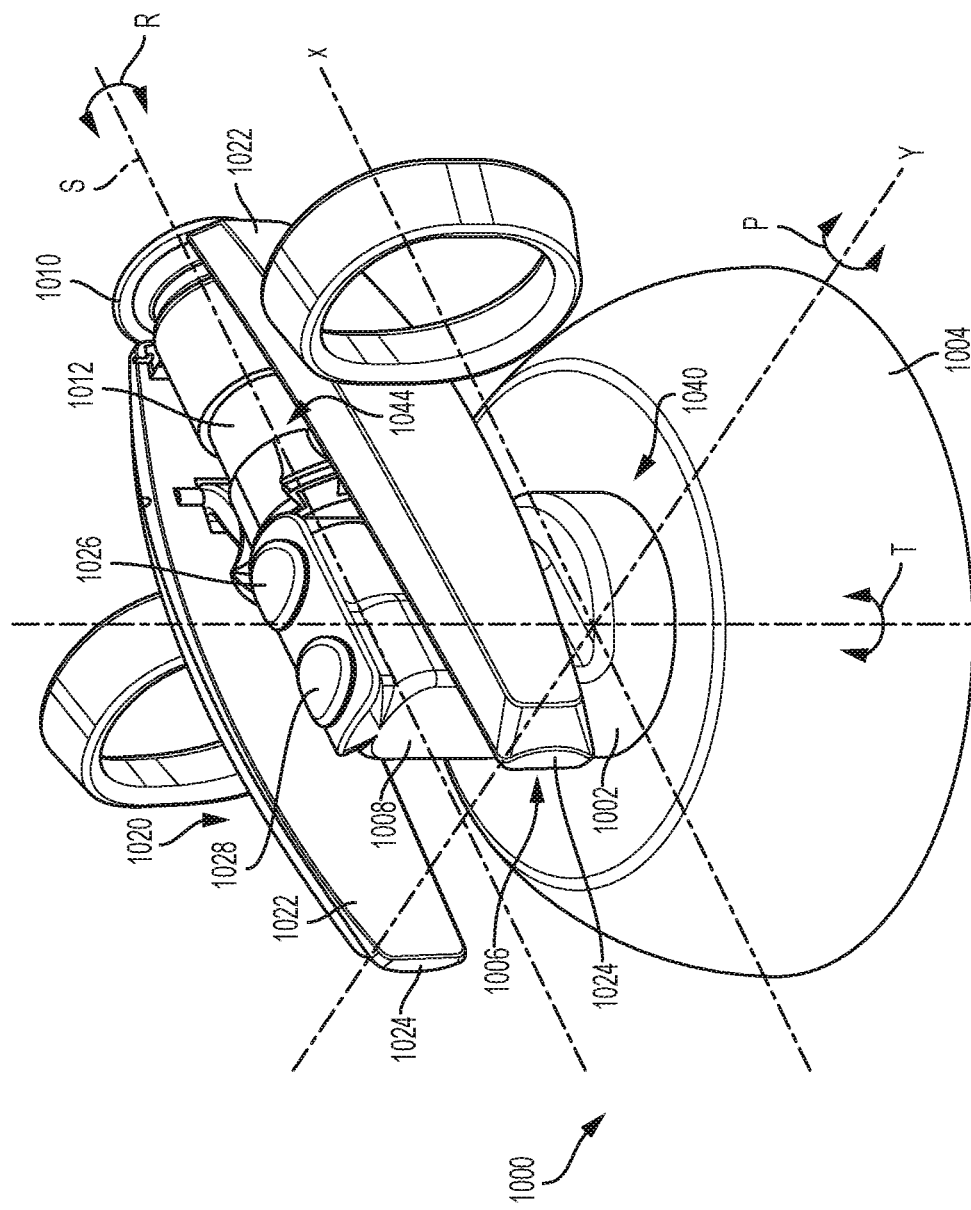
FIG. 6 is a perspective view of a user input device for a robotic surgical system, according to at least one aspect of the present disclosure.
Figure 7:
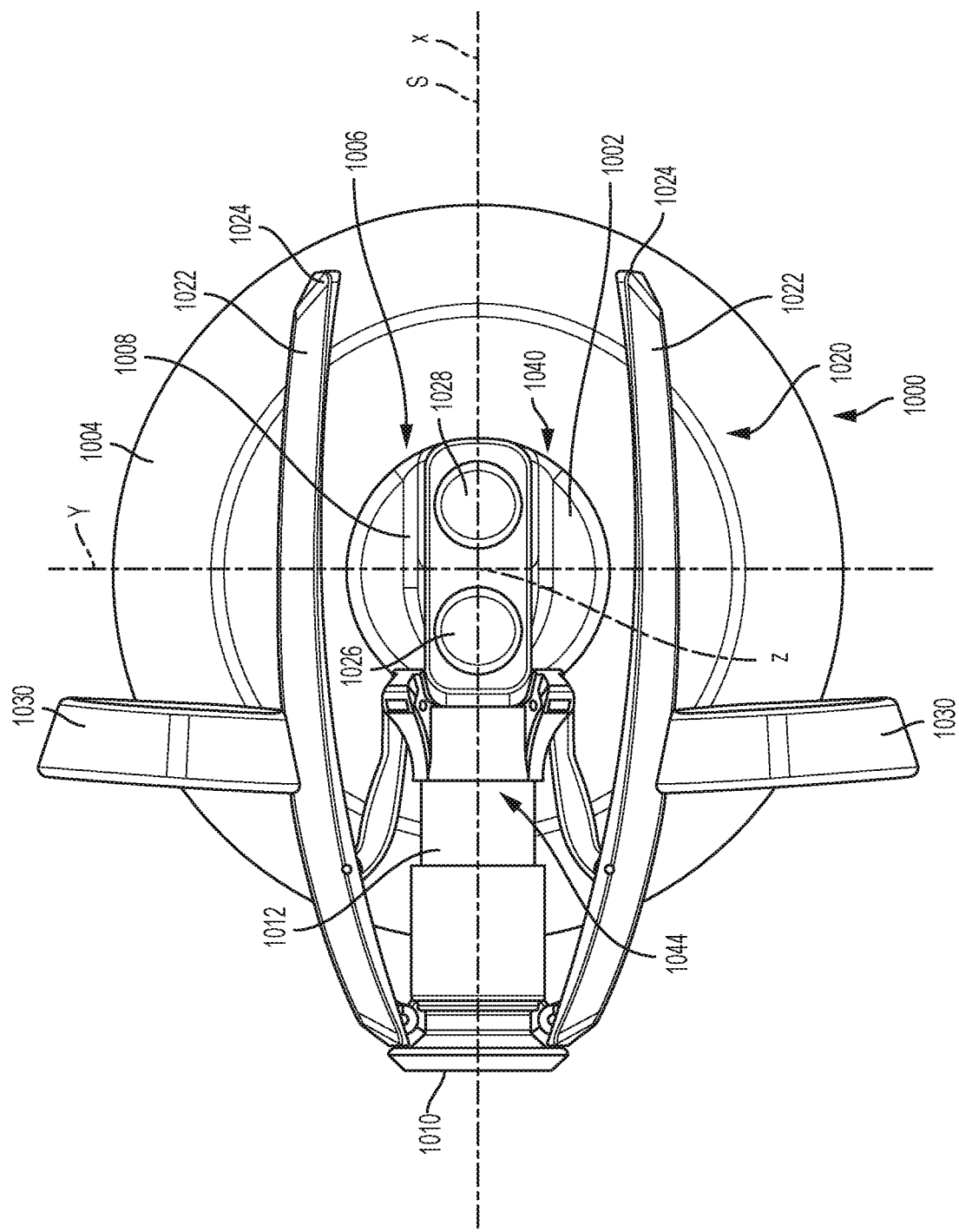
FIG. 7 is a plan view of the user input device of FIG. 6, according to at least one aspect of the present disclosure.
Figure 8:
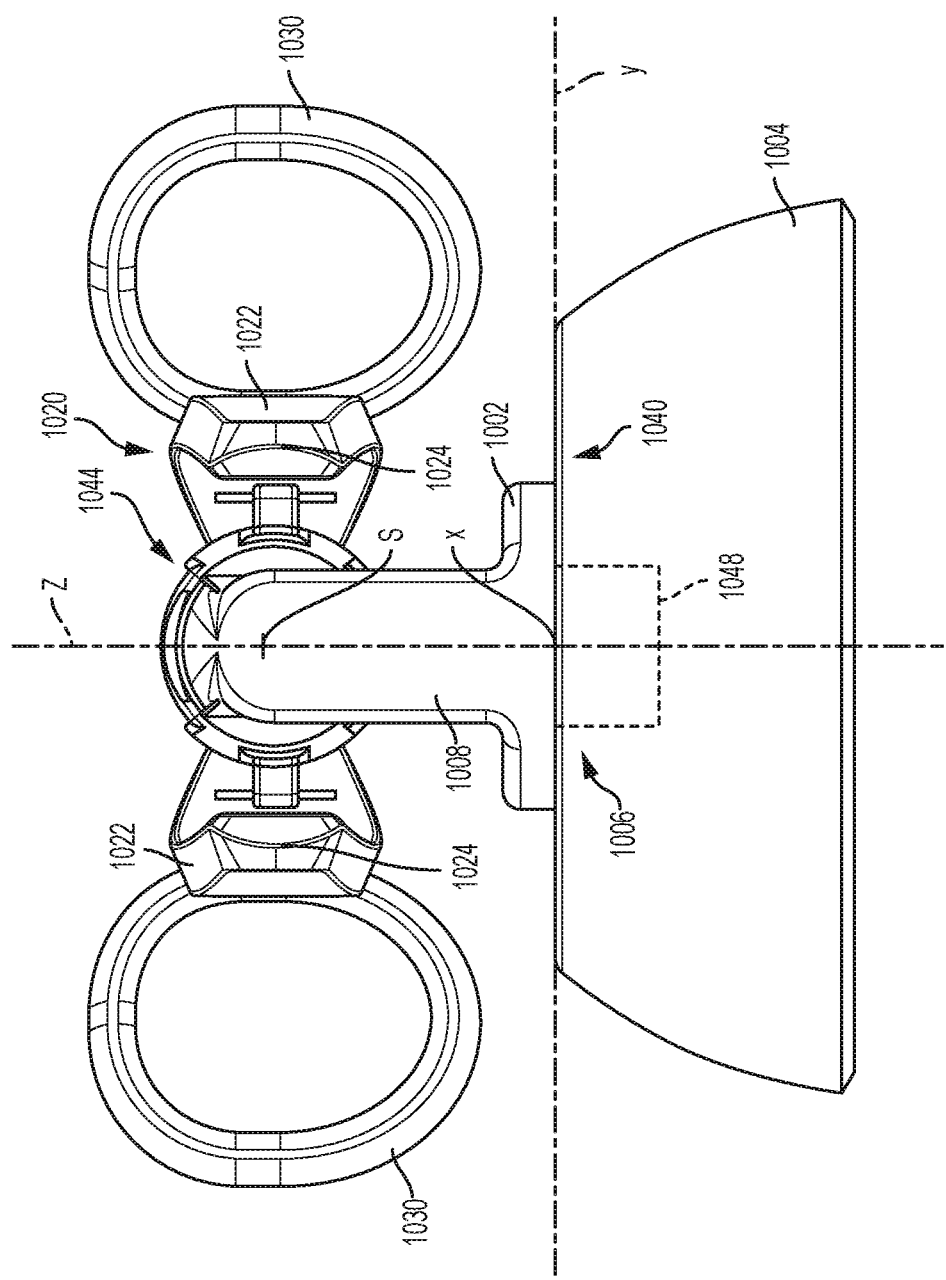
FIG. 8 is a rear elevation view of the user input device of FIG. 6, according to at least one aspect of the present disclosure.
Figure 9:
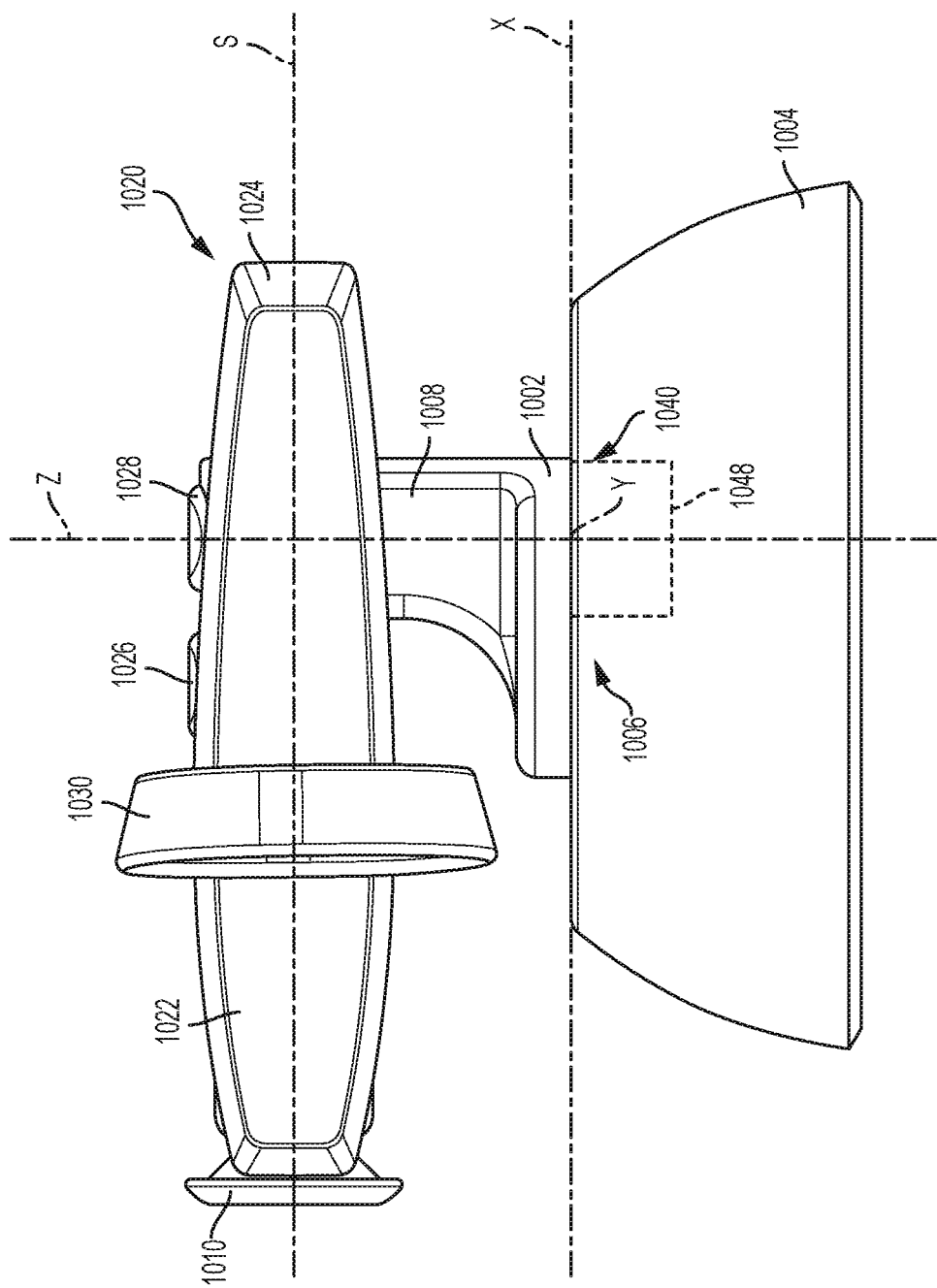
FIG. 9 is a side elevation view of the user input device of FIG. 6, according to at least one aspect of the present disclosure.

A handle assembly for use at a surgeon's console is further depicted in FIG. 5. The handle assembly of FIG. 5 includes a control input wrist 352 and a touch sensitive handle 325. The control input wrist 352 is a gimbaled device that pivotally supports the touch sensitive handle 325 to generate control signals that are used to control a robotic surgical manipulator and the robotic surgical tools. A pair of control input wrists 352 and touch sensitive handles 325 can be supported by a pair of control input arms in a workspace of the surgeon's console.

The control input wrist 352 includes first, second, and third gimbal members 362, 364, and 366, respectively. The third gimbal member 366 can be rotationally mounted to a control input arm. The touch sensitive handle 325 include a tubular support structure 351, a first grip 350A, and a second grip 350B. The first grip 350A and the second grip 350B are supported at one end by the tubular support structure 351. The touch sensitive handle 325 can be rotated about axis G. The grips 350A, 350B can be squeezed or pinched together about the tubular support structure 351. The "pinching" or grasping degree of freedom in the grips is indicated by arrows Ha and Hb.

The touch sensitive handle 325 is rotatably supported by the first gimbal member 362 by means of a rotational joint 356g. The first gimbal member 362 is in turn, rotatably supported by the second gimbal member 364 by means of the rotational joint 356f. Similarly, the second gimbal member 364 is rotatably supported by the third gimbal member 366 using a rotational joint 356e. In this manner, the control input wrist 352 allows the touch sensitive handle 325 to be moved and oriented in the workspace using three degrees of freedom.

The movements in the gimbals 362, 364, 366 of the control input wrist 352 to reorient the touch sensitive handle 325 in space can be translated into control signals to control a robotic surgical manipulator and the robotic surgical tools. The movements in the grips 350A and 350B of the touch sensitive handle 325 can also be translated into control signals to control the robotic surgical manipulator and the robotic surgical tools. In particular, the squeezing motion of the grips 350A and 350B over their freedom of movement indicated by arrows Ha and Hb, may be used to control the end effectors of the robotic surgical tools.

To sense the movements in the touch sensitive handle 325 and generate controls signals, sensors can be mounted in the handle 325 as well as the first gimbal member 362 of the control input wrist 352. Exemplary sensors may be a pressure sensor, Hall Effect transducer, a potentiometer, and/or an encoder, for example. The robotic surgical systems and handle assembly of FIG. 5 are further described in U.S. Pat. No. 8,224,484, titled METHODS OF USER INTERFACE WITH ALTERNATIVE TOOL MODE FOR ROBOTIC SURGICAL TOOLS, which issued Jul. 17, 2012, the entire disclosure of which is incorporated by reference herein.

Existing robotic systems can incorporate a surgical visualization system, as further described herein. In such instances, additional information regarding the surgical site can be determined and/or conveyed to the clinician(s) in the surgical theater, such as to a surgeon positioned at a surgeon's console. For example, the clinician(s) can observe an augmented view of reality of the surgical site that includes additional information such as various contours of the tissue surface, hidden critical structures, and/or one or more distances with respect to anatomical structures. In various instances, proximity data can be leveraged to improve one or more operations of the robotic surgical system and or controls thereof, as further described herein.

Input Control Devices

Referring again to the robotic system 150 in FIG. 3, the surgeon's console 152 allows the surgeon to provide manual input commands to the surgical robot 154 to effect control of the surgical tool and the various actuations thereof. Movement of an input control device by a surgeon at the surgeon's console 152 within a predefined working volume, or work envelope, results in a corresponding movement or operation of the surgical tool. For example, referring again to FIG. 2, a surgeon can engage each input control device 136 with one hand and move the input control devices 136 within the work envelope to provide control motions to the surgical tool. Surgeon's consoles (e.g. the surgeon's console 116 in FIGS. 1 and 2 and the surgeon's console 250 in FIG. 4) can be expensive and require a large footprint. For example, the working volume of the user input device (e.g. the handle/wrist assembly 262 in FIG. 4 and the control input wrist 352 and touch sensitive handle 325 in FIG. 5) at the surgeon's consoles can necessitate a large footprint, which impacts the usable space in the operating room (OR), training modalities, and cooperative procedures, for example. For example, such a large footprint can preclude the option of having multiple control stations in the OR, such as additional control stations for training or use by an assistant. Additionally, the size and bulkiness of a surgeon's console can be cumbersome to relocate within an operating room or move between operating rooms, for example.

Ergonomics is an important consideration for surgeons who may spend many hours each day in surgery and/or at the surgeon's console. Excessive, repetitive motions during surgical procedures can lead to fatigue and chronic injury for the surgeon. It can be desirable to maintain a comfortable posture and/or body position while providing inputs to the robotic system. However, in certain instances, the surgeon's posture and/or position may be compromised to ensure proper positioning of a surgical tool. For example, surgeons are often prone to contort their hands and/or extend their arms for long durations of time. In one instance, a gross control motion to move the surgical tool to the surgical site may result in the surgeon's arms being uncomfortably too outstretched and/or cramped uncomfortably close upon reaching the surgical site. In certain instances, poor ergonomic posturing achieved during the gross control motion may be maintained during a subsequent fine control motion, e.g. when manipulating tissue at the surgical site, which can further exasperate the poor ergonomics for the surgeon. Existing input control devices propose a one-size-fits-all approach regardless of the surgeon's anthropometrics; however, the ergonomic impact to a surgeon can vary and certain body types may be more burdened by the architecture of existing input control devices.

In certain instances, an input control device can be restrained within the work envelope that defines its range of motion. For example, the structure of the surgeon's console and/or the linkages on the input control device can limit the range of the motion of the input control device. In certain instances, the input control device can reach the end of its range of motion before the surgical tool is appropriately positioned. In such instances, a clutching mechanism can be required to reposition the input control device within the work envelope to complete the positioning of the surgical tool. A hypothetical work envelope 280 is shown in FIG. 4, for example. In various instances, the surgeon can be required to actuate a clutch (often in the form of a foot pedal or additional button on the handle of the input control device) to temporarily disengage the input control device from the surgical tool while the input control device is relocated to a desired position within the work envelope. This non-surgical motion by the surgeon can be referred to as a "rowing" motion to properly reposition the user input device within the work envelope because of the arm motion of the surgeon at the surgeon's console. Upon release of the clutch, the motions of the input control device can again control the surgical tool.

Clutching the input control device to maintain a suitable position within the work envelope poses an additional cognitive burden to the surgeon. In such instances, the surgeon is required to constantly monitor the position and orientation of his/her hands relative to the boundaries of the work envelope. Additionally, the clutching or "rowing" motion can be tedious to the surgeon and such a monotonous, repetitive motion does not match the analogous workflow of a surgical procedure outside the context of robotic surgery. Clutching also requires the surgeon to match a previous orientation of the handle when reengaging the system. For example, upon completion of a complex range of motion in which the surgeon "rows" or clutches the input control device back to a comfortable, home position, the surgeon and/or surgical robot must match the orientation of the handle of the input control device in the home position to the previous orientation of the handle in the extended position, which can be challenging and/or require complex logic and/or mechanics.

Requiring a clutch mechanism also limits the availability of controls on the handle of the input control device. For example, a clutch actuator can take up valuable real estate on the handle, which cognitively and physically limits the availability of other controls on the handle. In turn, the complexity of other subsystems, such as a peddle board, is increased and the surgeon may be required to utilize multiple input systems to complete a simple task.

Non-clutched alternatives to such input control devices can reduce the footprint and cost of the surgeon's console, improve the surgeon's ergonomic experience, eliminate the physical and cognitive burdens associated with clutching, and/or provide additional real estate on the input control device for additional input controls, for example. Exemplary non-clutched input control devices are further described herein. Such non-clutched input control devices can be employed with a variety of robotic systems. Moreover, as further described herein, the non-clutched input control devices can leverage information from various distance determining subsystems also disclosed herein. For example, real-time structured light and three-dimensional shape modeling can inform the logic of such non-clutched input control devices such that a first mode and/or first collection of controls are enabled outside a predefined distance from an anatomical surface and/or critical structure and a second mode and/or second collection of controls are enabled within a predefined distance of the anatomical structure and/or critical structure. Various tissue proximity applications are further described herein.

Referring now to FIGS. 6-11, an input control device 1000 is shown. The input control device 1000 is a clutchless input control device, as further described herein. The input control device 1000 can be utilized at a surgeon's console or workspace for a robotic surgical system. For example, the input control device 1000 can be incorporated into a surgical system, such as the surgical system 110 (FIG. 1) or the surgical system 150 (FIG. 3), for example, to provide control signals to a surgical robot and/or surgical tool coupled thereto. The input control device 1000 includes input controls for moving the robotic arm and/or the surgical tool in three-dimensional space. For example, the surgical tool controlled by the input control device 1000 can be configured to move and/or rotate relative to X, Y, and Z axes.

Figure 12:
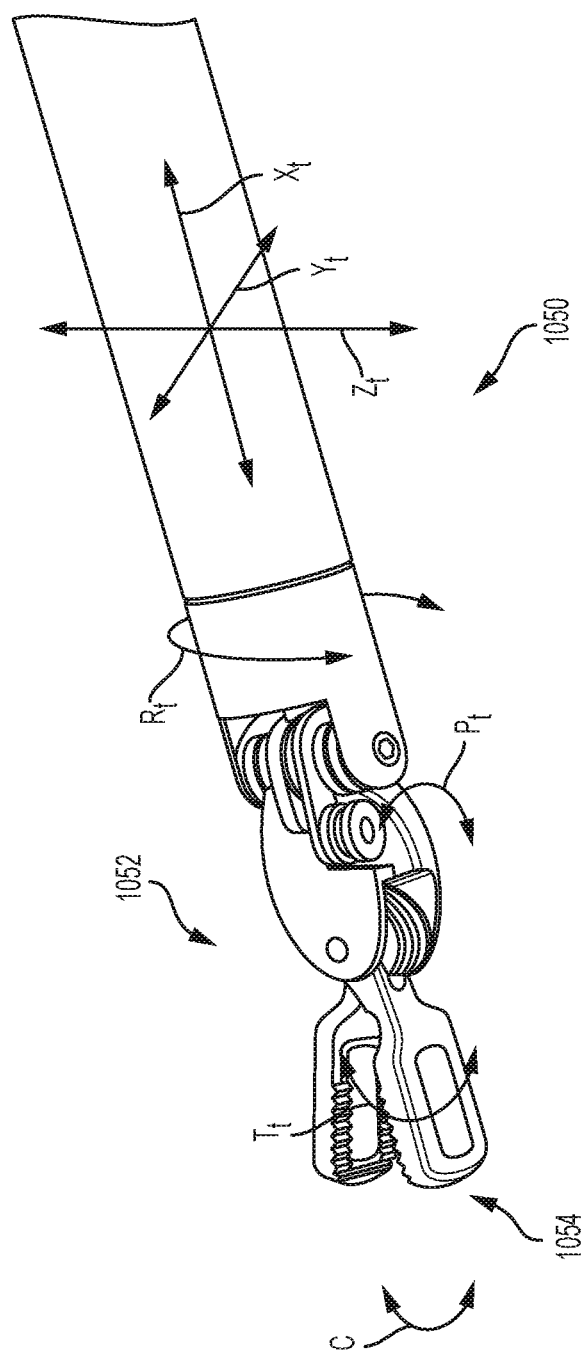
FIG. 12 is a perspective view of an end effector of a surgical tool operably controllable by control motions supplied to the user input device of FIG. 6, according to at least one aspect of the present disclosure.

An exemplary surgical tool 1050 is shown in FIG. 12. The surgical tool 1050 is a grasper that includes an end effector 1052 having opposing jaws 1054, which are configured to releasably grab tissue. The surgical tool 1050 can be maneuvered in three dimensional space by translating the surgical tool 1050 along the $X_t$, $Y_t$, and $Z_t$ axes thereof. The surgical tool 1050 also includes a plurality of joints such that the surgical tool can be rotated and/or articulated into a desired configuration. The surgical tool 1050 can be configured to rotate or roll about the $X_t$ axis defined by the longitudinal shaft of the surgical tool 1050, rotate or articulate about a first articulation axis parallel to the $Y_t$ axis, and rotate or articulate about a second articulation axis parallel to the $Z_t$ axis. Rolling about the $X_t$ axis corresponds to a rolling motion of the end effector 1052 in the direction $R_t$, articulation about the first articulation axis corresponds to a pitching motion of the end effector 1052 in the direction $P_t$, and articulation about the second articulation axis corresponds to a yawing or twisting motion in the direction $T_t$.

An input control device, such as the input control device 1000, for example, can be configured to control the translation and rotation of the end effector 1052. To control such motion, the input control device 1000 includes corresponding input controls. For example, the input control device 1000 includes at least six degrees of freedom of input controls for moving the surgical tool 1050 in three dimensional space along the $X_t$, $Y_t$, and $Z_t$ axes, for rolling the end effector 1052 about the $X_t$ axis, and for articulating the end effector 1052 about the first and second articulation axes. Additionally, the input control device 1000 includes an end effector actuator for actuating the opposing jaws of the end effector 1052 to manipulate or grip tissue. Additional features of the input control device 1000 with respect to a surgical tool, such as the surgical tool 1050, for example, are further described herein.

Referring again to FIGS. 6-11, the input control device 1000 includes a multi-dimensional space joint 1006 having a central portion 1002 supported on a base 1004. The base 1004 is structured to rest on a surface, such as a desk or work surface at a surgeon's console/workspace or at the patient's bedside, for example. The base 1004 defines a circular base with a contoured edge; however, alternative geometries are contemplated. The base 1004 can remain in a fixed, stationary position relative to an underlying surface upon application of the input controls thereto. In certain instances, the base 1004 can be releasably secured and/or clamped to the underlying surface with fasteners, such as threaded fasteners, for example. In other instances, fasteners may not be required to hold the base 1004 to the underlying surface. In various instances, the base 1004 can include a sticky or tacking bottom surface and/or suction features (e.g. suction cups or magnets) for gripping an underlying surface. In certain instances, the base 1004 can include a ribbed and/or grooved bottom surface for engaging a complementary underlying support surface.

The space joint 1006 is configured to receive multi-dimensional manual inputs from a surgeon (e.g. the surgeon's hand or arm) corresponding to control motions for the surgical tool in multi-dimensional space. The central portion 1002 of the space joint 1006 is configured to receive input forces in multiple directions, such as forces along and/or about the X, Y, and Z axes. The central portion 1002 can include a raising, lowering, and rotating cylinder, shaft, or hemisphere, for example, projecting from the base 1004. The central portion 1002 is flexibly supported relative to the base 1004 such that the cylinder, shaft, and/or hemisphere is configured to move or float within a small predefined zone upon receipt of force control inputs thereto. For example, the central portion 1002 can be a floating shaft that is supported on the base 1004 by one or more elastomeric members such as springs, for example. The central portion 1002 can be configured to move or float within a predefined three-dimensional volume. For example, elastomeric couplings can permit movement of the central portion 1002 relative to the base 1004; however, restraining plates, pins, and/or other structures can be configured to limit the range of motion of the central portion 1002 relative to the base 1004. In one aspect, movement of the central portion 1002 from a central or "home" position relative to the base 1004 can be permitted within a range of about 1.0 mm to about 5.0 mm in any direction (up, down, left, right, backwards and forwards). In other instances, movement of the central portion 1002 relative to the base 1004 can be restrained to less than 1.0 mm or more than 5.0 mm. In certain instances, the central portion 1002 can move about 2.0 mm in all directions relative to the base 1004. In various instances, the space joint 1006 can be similar to a multi-dimensional mouse, or space mouse. An exemplary space mouse is provided by 3Dconnexion Inc., for example.

In various instances, the space joint 1006 includes a multi-axis force and/or torque sensor arrangement 1048 (see FIGS. 8 and 9) configured to detect the input forces and moments applied to the central portion 1002 and transferred to the space joint 1006. The sensor arrangement 1048 is positioned on one or more of the surfaces at the interface between the central portion 1002 and the base 1004. In other instances, the sensor arrangement 1048 can be embedded in the central portion 1002 or the base 1004. In still other instances, the sensor arrangement 1048 can be positioned on a floating member positioned intermediate the central portion 1002 and the base 1004.

The sensor arrangement 1048 can include one or more resistive strain gauges, optical force sensors, optical distance sensors, miniature cameras in the range of about 1.0 mm to about 3.0 mm in size, and/or time of flight sensors utilizing a pulsed light source, for example. In one aspect, the sensor arrangement 1048 includes a plurality of resistive strain gauges configured to detect the different force vectors applied thereto. The strain gauges can define a Wheatstone bridge configuration, for example. Additionally or alternatively, the sensor arrangement 1048 can include a plurality of optoelectronic sensors, such as measuring cells comprising a position-sensitive detector illuminated by a light-emitting element, such as an LED. Alternative force-detecting sensor arrangements are also contemplated. Exemplary multi-dimensional input devices and/or sensor arrangements are further described in the following references, which are incorporated by reference herein in their respective entireties:

U.S. Pat. No. 4,785,180, titled OPTOELECTRIC SYSTEM HOUSED IN A PLASTIC SPHERE, issued Nov. 15, 1988;

U.S. Pat. No. 6,804,012, titled ARRANGEMENT FOR THE DEFECTION OF RELATIVE MOVEMENTS OR RELATIVE POSITION OF TWO OBJECTS, issued Oct. 12, 2004;

European Patent Application No. 1,850,210, titled OPTOELECTRONIC DEVICE FOR DETERMINING RELATIVE MOVEMENTS OR RELATIVE POSITIONS OF TWO OBJECTS, published Oct. 31, 2007;

U.S. Patent Application Publication No. 2008/0001919, titled USER INTERFACE DEVICE, published Jan. 3, 2008; and U.S. Pat. No. 7,516,675, titled JOYSTICK SENSOR APPARATUS, issued Apr. 14, 2009.

Referring again to the input control device 1000 in FIGS. 6-11, a joystick 1008 extends from the central portion 1002. Forces exerted on the central portion 1002 via the joystick 1008 define input motions for the sensor arrangement 1048. For example, the sensor arrangement 1048 (FIGS. 8 and 9) in the base 1004 can be configured to detect the input forces and moments applied by a surgeon to the joystick 1008. The joystick 1008 can be spring-biased toward a central, or home, position, in which the joystick 1008 is aligned with the Z axis, a vertical axis through the joystick 1008, central portion 1002, and the space joint 1006. Driving (e.g. pushing and/or pulling) the joystick 1008 away from the Z axis in any direction can be configured to "drive" an end effector of an associated surgical tool in the corresponding direction. When the external driving force is removed, the joystick 1008 can be configured to return to the central, or home, position and motion of the end effector can be halted. For example, the central portion 1002 and joystick 1008 can be spring-biased toward the home position.

In various instances, the space joint 1006 and the joystick 1008 coupled thereto define a six degree-of-freedom input control. Referring again now to the end effector 1052 of the surgical tool 1050 in FIG. 12, the forces on the joystick 1008 of the input control device 1000 in the X direction correspond to displacement of the end effector 1052 along the $X_t$ axis thereof (e.g. longitudinally), forces on the joystick 1008 in the Y direction correspond to displacement of the end effector 1052 along the $Y_t$ axis thereof (e.g. laterally), and forces on the joystick 1008 in the Z direction correspond to displacement of the end effector 1052 along the $Z_t$ axis (e.g. vertically/up and down). Additionally, forces on the joystick 1008 about the X axis (the moment forces R) result in rotation of the end effector 1052 about the $X_t$ axis (e.g. a rolling motion about a longitudinal axis in the direction $R_t$), forces on the joystick 1008 about the Y axis (the moments forces P) result in articulation of the end effector 1052 about the $Y_t$ axis (e.g. a pitching motion in the direction $P_t$), and forces on the joystick 1008 about the Z axis (the moment forces T) result in articulation of the end effector 1052 about the $Z_t$ axis of the end effector (e.g. a yawing or twisting motion in the direction $T_t$). In such instances, the input control device 1000 comprises a six-degree of freedom joystick, which is configured to receive and detect six degrees-of-freedom—forces along the X, Y, and Z axes and moments about the X, Y, and Z axes. The forces can correspond to translational input and the moments can correspond to rotational inputs for the end effector 1052 of the associated surgical tool 1050. Six degree-of-freedom input devices are further described herein. Additional degrees of freedom (e.g. for actuating the jaws of an end effector or rolling the end effector about a longitudinal axis) can be provided by additional joints supported by the joystick 1008, as further described herein.

In various instances, the input control device 1000 includes a wrist or joint 1010 that is offset from the space joint 1006. The wrist 1010 is offset from the space joint 1006 by a shaft, or lever, 1012 extending along the shaft axis S that is parallel to the axis X in the configuration shown in FIG. 6. For example, the joystick 1008 can extend upright vertically from the central portion 1002 and the base 1004, and the joystick 1008 can support the shaft 1012.

As further described herein, the space joint 1006 can define the input control motions for multiple degrees of freedom. For example, the space joint 1006 can define the input control motions for translation of the surgical tool in three-dimensional space and articulation of the surgical tool about at least one axis. Rolling motions can also be controlled by inputs to the space joint 1006, as further described herein. Moreover, the wrist 1010 can define input control motions for at least one degree of freedom. For example, the wrist 1010 can define the input control motions for the rolling motion of the end effector. Moreover, the wrist 1010 can support an end effector actuator 1020, which is further described herein, to apply open and closing motions to the end effector.

In certain instances, the rolling, yawing, and pitching motions of the input control device 1000 are translatable motions that define corresponding input control motions for the related end effector. In various instances, the input control device 1000 can utilize adjustable scaling and/or gains such that the motion of the end effector is scalable in relationship to the control motions delivered at the wrist 1010.

In one aspect, the input control device 1000 includes a plurality of mechanical joints, which can be elastically-coupled components, sliders, journaled shafts, hinges, and/or rotary bearings, for example. The mechanical joints include a first joint 1040 (at the space joint 1006) intermediate the base 1004 and the central portion 1002, which allows rotation and tilting of the central portion 1002 relative to the base 1004, and a second joint 1044, which allows rotation of the wrist 1010 relative to the joystick 1008. In various instances, six degrees of freedom of a robotic end effector (e.g. three-dimensional translation and rotation about three different axes) can be controlled by user inputs at only these two joints 1040, 1044, for example. With respect to motion at the first joint 1040, the central portion 1002 can be configured to float relative to the base 1004 at elastic couplings, as further described herein. With respect to the second joint 1044, the wrist 1010 can be rotatably coupled to the shaft 1012, such that the wrist 1010 can rotate in the direction R (FIG. 6) about the shaft axis S. Rotation of the wrist 1010 relative to the shaft 1012 can correspond to a rolling motion of an end effector about a central tool axis, such as the rolling of the end effector 1052 about the $X_t$ axis. Rotation of the wrist 1010 by the surgeon to roll an end effector provides control of the rolling motion at the surgeon's fingertips and corresponds to a first-person perspective control of the end effector (i.e. from the surgeon's perspective, being "positioned" at the jaws of the remotely-positioned end effector at the surgical site). As further described herein, such placement and perspective can be utilized to supply precision control motions to the input control device 1000 during portions of a surgical procedure (e.g. a precision motion mode).

The various rotary joints of the input control device can include a sensor arrangement configured to detect the rotary input controls applied thereto. The wrist 1010 can include a rotary sensor (e.g. the sensor 1049 in FIG. 25), which can be a rotary force/torque sensor and/or transducer, rotary strain gauge and/or strain gauge on a spring, rotary encoder, and/or an optical sensor to detect rotary displacement at the joint, for example.

In certain instances, the input control device 1000 can include one or more additional joints and/or hinges for the application of rotational input motions corresponding to articulation of an end effector. For example, the input control device 1000 can include a hinge along the shaft 1012 and/or between the shaft 1012 and the joystick 1008. In one instance, hinged input motions at such a joint can be detected by another sensor arrangement and converted to rotary input control motions for the end effector, such as a yawing or pitching articulation of the end effector. Such an arrangement requires one or more additional sensor arrangements and would increase the mechanical complexity of the input control device.

The input control device 1000 also includes the end effector actuator 1020. The end effector actuator 1020 includes opposing fingers 1022 extending from the wrist 1010 toward the joystick 1008 and the central portion 1002 of the space joint 1006. The opposing fingers 1022 extend distally beyond the space joint 1006. In such instances, the wrist 1010 is proximal to the space joint 1006, and the distal ends 1024 of the opposing fingers 1022 are distal to the space joint 1006, which mirrors the jaws being positioned distal to the articulation joints of a robotic tool, for example. Applying an actuation force to the opposing fingers 1022 comprises an input control for a surgical tool. For example, referring again to FIG. 12, applying a pinching force to the opposing fingers 1022 can close and/or clamp the jaws 1054 of the end effector 1052 (see arrows C in FIG. 12). In various instances, applying a spreading force can open and/or release the jaws 1054 of the end effector 1052, such as for a spread dissection task, for example. The end effector actuator 1020 can include at least one sensor for detecting input control motions applied to the opposing fingers 1022. For example, the end effector actuator can include a displacement sensor and/or a rotary encoder for detecting the input control motions applied to pivot the opposing fingers 1022 relative to the shaft 1012.

In various instances, the end effector actuator 1020 can include one or more loops 1030, which are dimensioned and positioned to receive a surgeon's digits. For example, referring primarily to FIGS. 10 and 11, the surgeon's thumb T is positioned through one of the loops 1030 and the surgeon's middle finger M is positioned through the other loop 1030. In such instances, the surgeon can pinch and/or spread his thumb T and middle finger M to actuate the end effector actuator 1020. In other instances, the loops 1030 can be structured to receive more than one digit and, depending on the placement of the loops 1030, different digits may engage the loops. In various instances, the finger loops 1030 can facilitate spread dissection functions and/or translation of the robotic tool upward or downward (i.e. the application of a vertical force at the space joint 1006, for example). In certain instances, the loops 1030 can define complete loops; however, in other instances, partial loops (e.g. half-circles) can be utilized. In still other instances, the end effector actuator 1020 may not include the loops 1030. For example, the end effector actuator 1020 can be spring-biased outwardly such that loops are not needed to draw the opposing fingers 1022 apart, such as for spread dissection functions.

The opposing fingers 1022 of the end effector actuator 1020 define a line of symmetry that is aligned with the longitudinal shaft axis S along which the shaft 1012 extends when the fingers 1022 are in unactuated positions. The line of symmetry is parallel to the axis X through the multi-dimensional space joint 1006. Moreover, the central axis of the joystick 1008 is aligned with the line of symmetry. In various instances, the motion of the opposing fingers 1022 can be independent. In other words, the opposing fingers 1022 can be displaced asymmetrically relative to the longitudinal shaft axis S during an actuation. The displacement of the opposing fingers 1022 can depend on the force applied by the surgeon, for example. With certain surgical tools, the jaws of the end effector can pivot about an articulation axis such that various closed positions of the jaws are not longitudinally aligned with the shaft of the surgical tool. Moreover, in certain instances, it can be desirable to hold one jaw stationary, such as against fragile tissue and/or a critical structure, and to move the other jaw relative to the non-moving jaw. To accommodate such closure motions, the range of motion of the opposing fingers 1022 on the input control device 1000 can be larger than the range of motion of the jaws of the end effector, for example. For example, referring to FIG. 12A, the surgical tool 1050' is shown in an articulated configuration in which the jaws can be clamped together out of alignment with a longitudinal shaft axis of the surgical tool 1050'. In such instances, the jaws and, thus the fingers 1022 on the input control device 1000 (FIGS. 6-11) would be actuated asymmetrically to move the jaws of the end effector 1052 to a closed configuration.

Referring now to FIGS. 13A-15B, various control motions applied to the end effector actuator 1020 and corresponding actuations of an end effector 1062 are shown. The end effector 1062 includes opposing jaws 1064 that are movable between an open configuration (FIG. 13A), an intermediate configuration (FIG. 14A), and a closed configuration (FIG. 15A) as the opposing fingers 1022 of the end effector actuator 1020 move between an open configuration (FIG. 13B), an intermediate configuration (FIG. 14B), and a closed configuration (FIG. 15B), respectively.

The input control device 1000 also includes at least one additional actuator, such as the actuation buttons 1026, 1028, for example, which can provide additional controls at the surgeon's fingertips. For example, the actuation buttons 1026, 1028 are positioned on the joystick 1008 of the input control device 1000 such that the surgeon can access the buttons 1026, 1026 with a digit, such as an index finger I. The actuation buttons 1026, 1028 can correspond to buttons for activating the surgical tool, such as firing, extending, activating, translating, and/or retracting a knife, energizing one or more electrodes, adjusting an energy modularity, affecting diagnostics, biopsy sampling, ablation, and/or other surgical tasks, for example. In other instances, the actuation buttons 1026, 1028 can provide inputs to an imaging system to adjust a view of the surgical tool, such as zooming in/out, panning, tracking, titling and/or rotating, for example. In certain instance the actuators can be positioned in different locations than the actuation buttons 1026, 1028, such as positioned for use by a thumb or another digit, for example. Additionally or alternatively, the actuators can be provided on a touch screen and/or foot pedal, for example.

Figure 10:
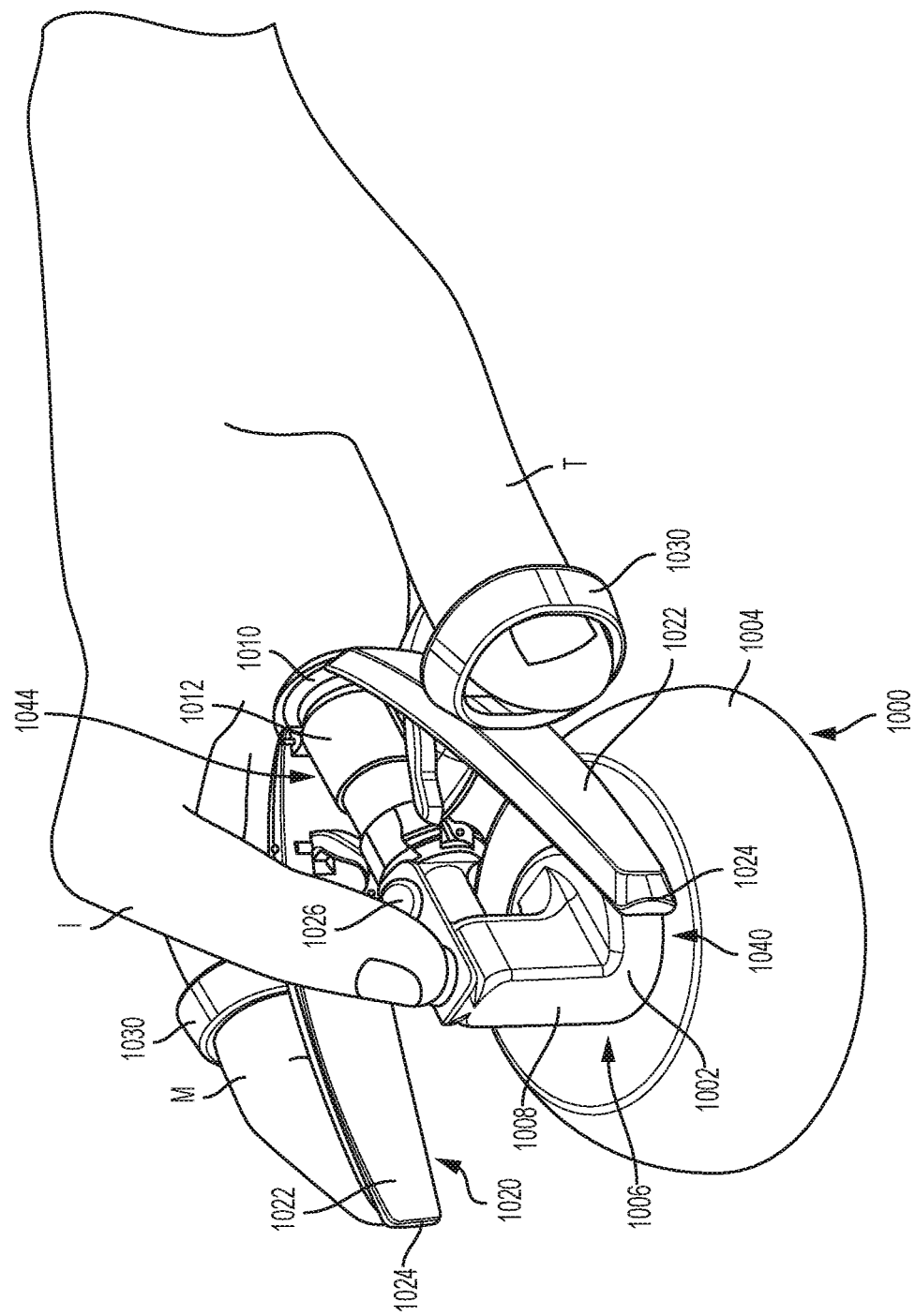
FIG. 10 is a perspective view of a user's hand engaged with the user input device of FIG. 6, according to at least one aspect of the present disclosure.
Figure 11:
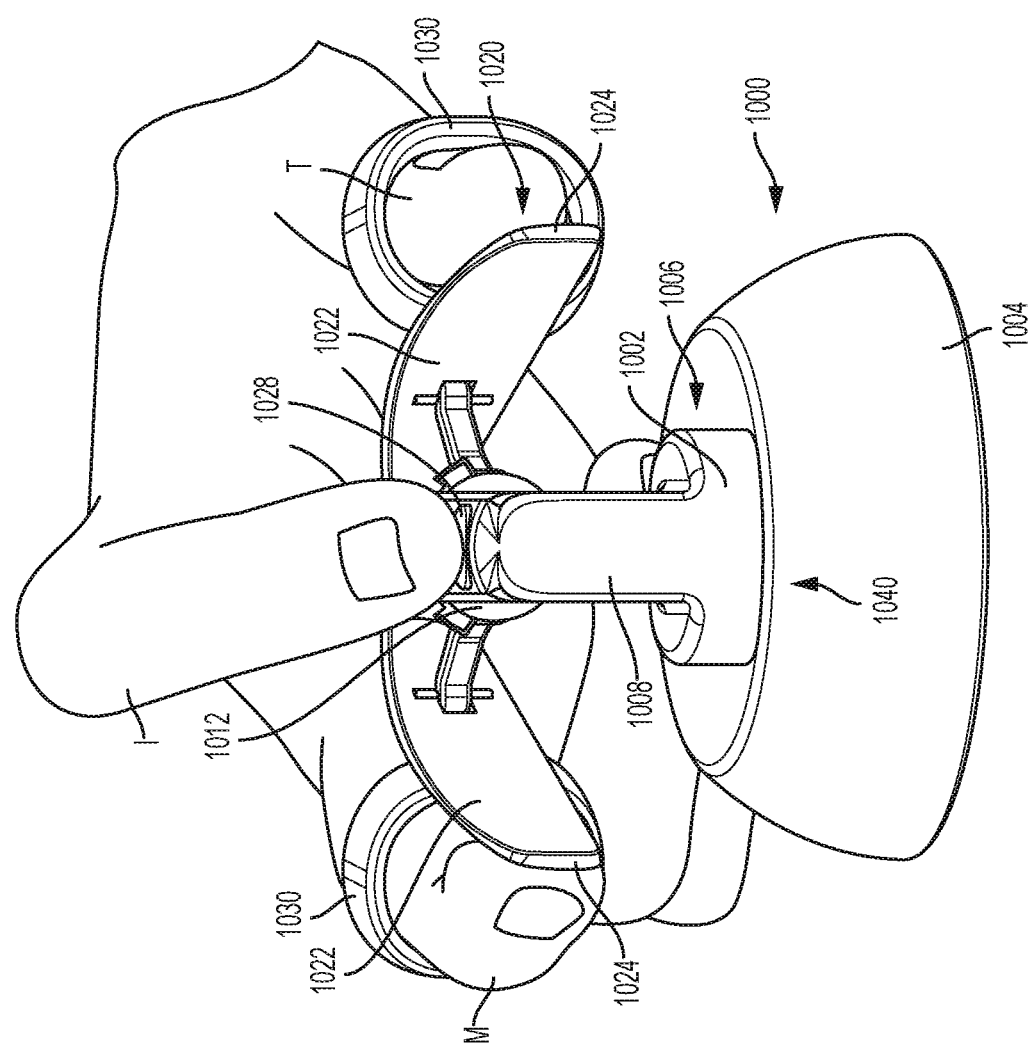
FIG. 11 is a rear elevation view of a user's hand engaged with the user input device of FIG. 6, according to at least one aspect of the present disclosure.
Figure 12A:
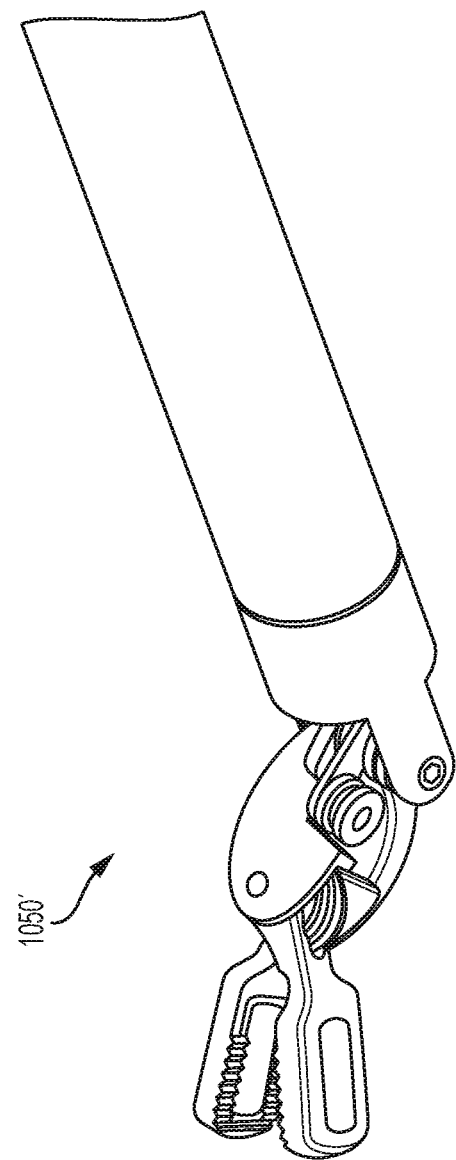
FIG. 12A is a perspective view of the end effector of FIG. 12, depicting the end effector in an articulated configuration, according to at least one aspect of the present disclosure.
Figure 13A:
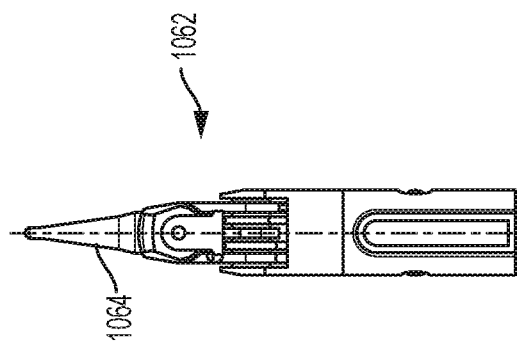
Figure 13B:
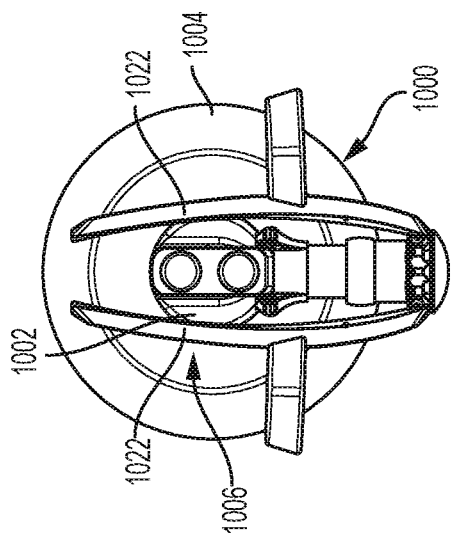
Figure 14A:
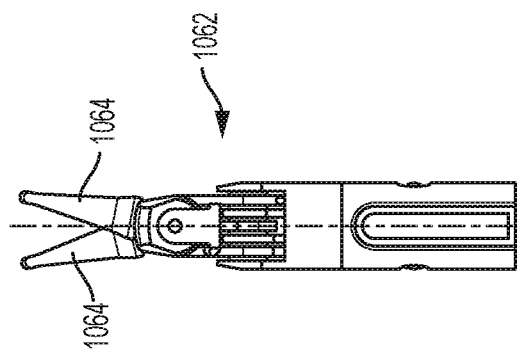
Figure 14B:
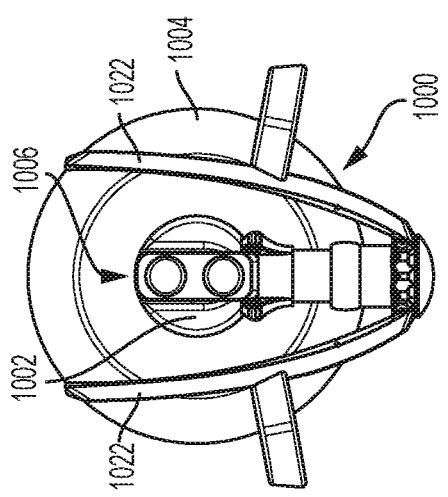
Figure 15A:
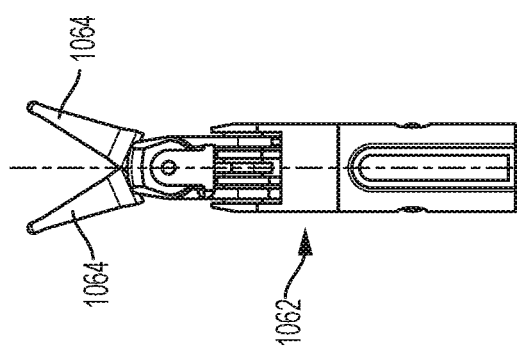
Figure 15B:
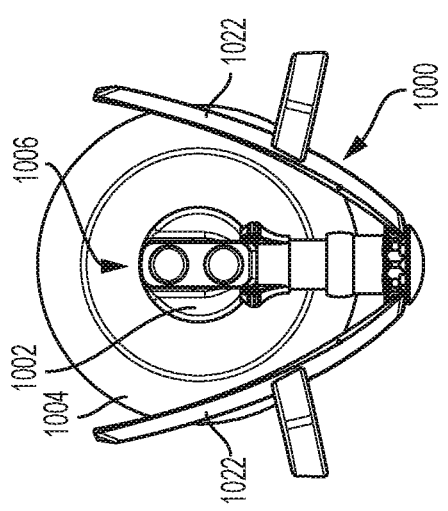

Referring primarily now to FIGS. 10 and 11, a user is configured to position his or her hand relative to the input control device 1000 such that the wrist 1010 is proximal to the space joint 1006. More specifically, the user's palm is positioned adjacent to the wrist 1010 and the user's fingers extend distally toward the joystick 1008 and the central portion 1002 of the space joint 1006. Distally-extending fingers 1022 (for actuation of the jaws) and the actuation buttons 1026, 1028 (for actuation of a surgical function at the jaws) are distal to the space joint 1006 and wrist 1010. Such a configuration mirrors the configuration of a surgical tool in which the end effector is distal to a more-proximal articulation joint(s) and/or rotatable shaft and, thus, provides an intuitive arrangement that facilitates a surgeon's training and adoption of the input control device 1000.

In various instances, a clutch-less input control device including a six degree-of-freedom input control, an end effector actuator, and additional actuation buttons can define alternative geometries to the input control device 1000. Stated differently, a clutch-less input control device does not prescribe the specific form of the joystick assembly of the input control device 1000. Rather, a wide range of interfaces may be designed based on formative testing and user preferences. In various instances, a robotic system can allow for users to choose from a variety of different forms to select the style that best suits his/her needs. For example, a pincher, pistol, ball, pen, and/or a hybrid grip, among other input controls, can be supported. Alternative designs are further described herein and in various commonly-owned patent applications that have been incorporated by reference herein in their respective entireties.

In various instances, the input controls for the input control device 1000 are segmented between first control motions and second control motions. For example, first control motions and/or parameters therefor can be actuated in a first mode and second control motions and/or parameters therefor can be actuated in a second mode. The mode can be based on a factor provided by the surgeon and/or the surgical robot control system and/or detected during the surgical procedure. For example, the mode can depend on the proximity of the surgical tool to tissue, such as the proximity of the surgical tool to the surface of tissue and/or to a critical structure. Various distance determining systems for determining proximity to one or more exposed and/or at least partially hidden critical structures are further described herein.

Figure 25:
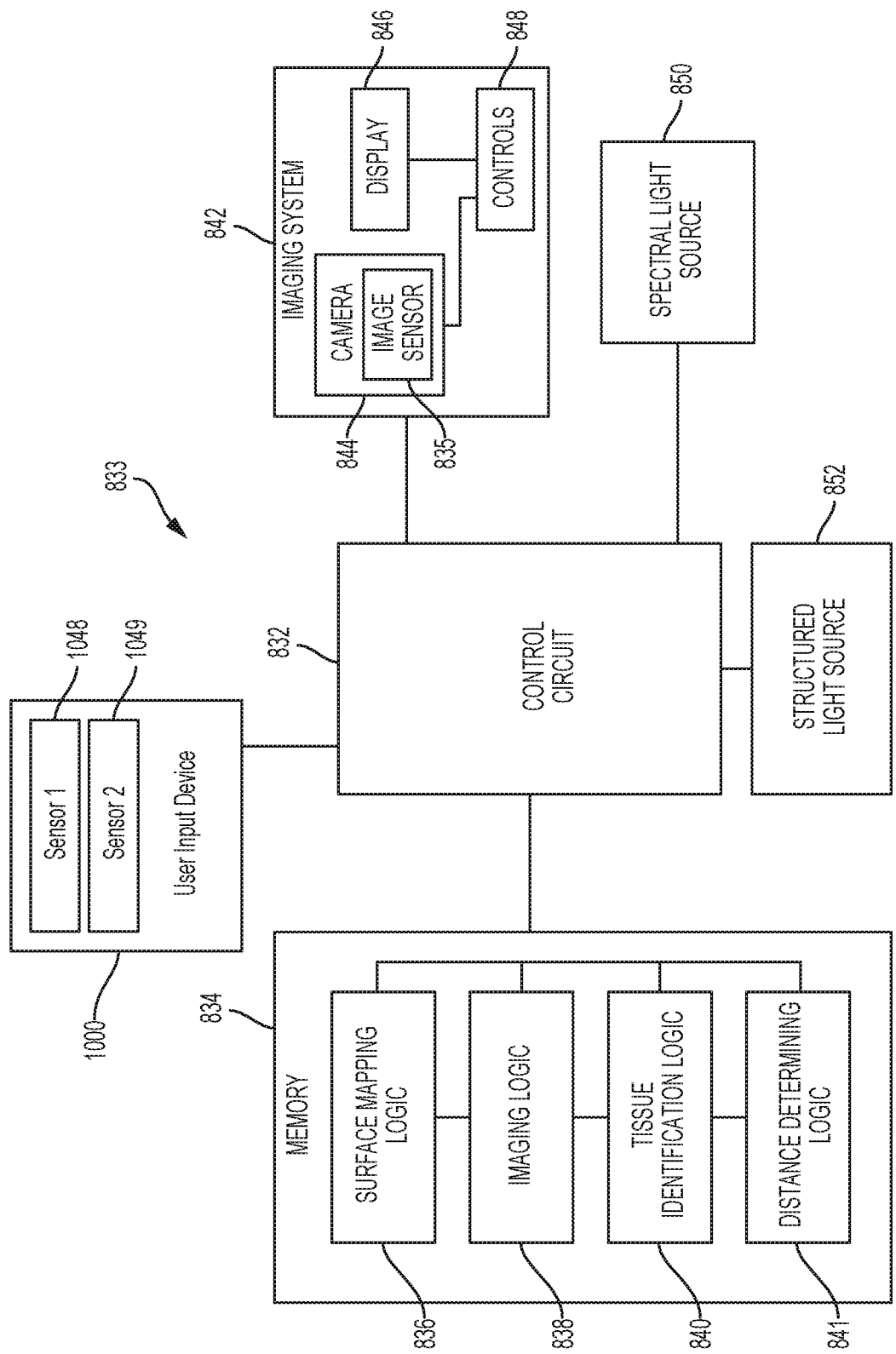
FIG. 25 is a schematic of a control system for a surgical visualization system configured to receive inputs from a user input device, according to at least one aspect of the present disclosure.

In one instance, referring now to FIG. 25, the input control device 1000 can be communicatively coupled to a control circuit 832 of a control system 833, which is further described herein. In the control system 833, the control circuit 832 can receive input signals from the input control device 1000, such as feedback detected by the various sensors therein and related to control inputs at the joystick 1008 and/or wrist 1010 and/or outputs from the various sensors thereon (e.g. the sensor arrangement 1048 and/or the rotary sensor 1049 at the wrist 1010. For example, signals detected by the sensor arrangement 1048, i.e. the multi-axis force and torque sensor of the space joint 1006, can be provided to the control circuit 832. Additionally, signals detected by the sensor 1049, i.e., the rotary sensor of the wrist 1010, can be provided to the control circuit 832. A memory 834 for the control system 833 also includes control logic for implementing the input controls provided to the input control device 1000 and detected by the various sensors (e.g. the sensors 1048 and 1049).

Figures 11A, 11B:
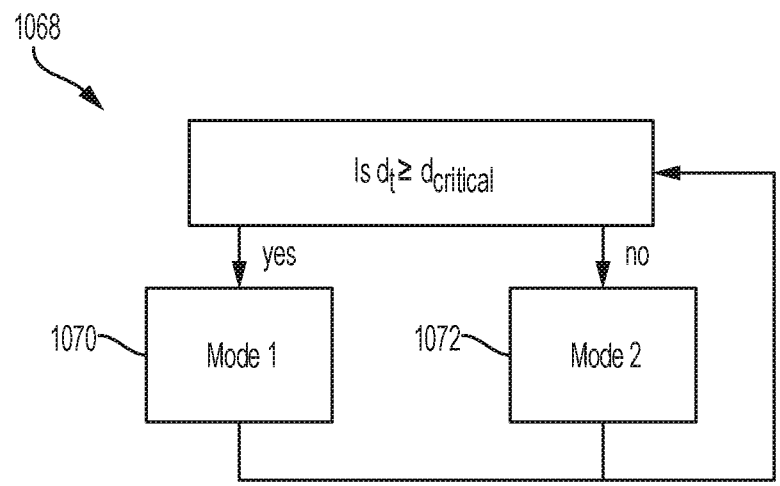
FIG. 11A is a control logic flowchart for the user input device of FIG. 6, according to at least one aspect of the present disclosure.
FIG. 11B is a table depicting control parameters for operational modes of the user input device of FIG. 6, according to at least one aspect of the present disclosure.

Referring now to FIG. 11A, control logic 1068 for the input control device 1000 can implement a first mode 1070 if the distance determined by a distance determining subsystem is greater than or equal to a critical distance and can implement a second mode 1072 if the distance determined by the distance determining subsystem is less than the critical distance. The control logic can be utilized in the control circuit 832, a control circuit 1400 (FIG. 11C), a combinational logical circuit 1410 (FIG. 11D), and/or a sequential logic circuit 1420 (FIG. 11E), for example, where an input is provided from inputs to the input control device 1000 (FIGS. 6-11) and/or a surgical visualization system or distance determining subsystem thereof, as further described herein.

Figure 11C:
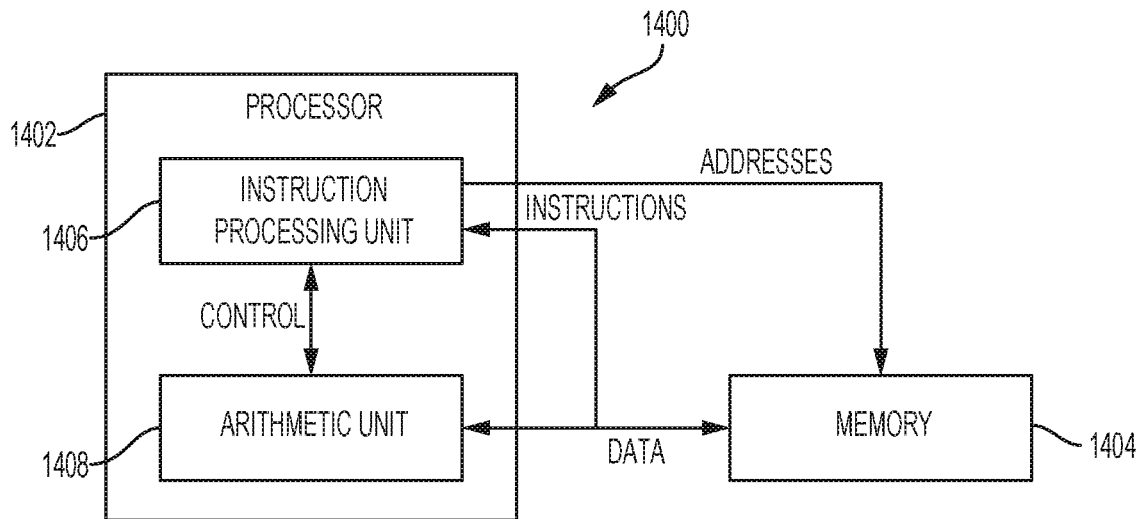
FIG. 11C illustrates a control circuit configured to control aspects of the user input device of FIG. 6, according to at least one aspect of the present disclosure.

For example, turning to FIG. 11C, the control circuit 1400 can be configured to control aspects of the input control device 1000, according to at least one aspect of this disclosure. The control circuit 1400 can be configured to implement various processes described herein. The control circuit 1400 may comprise a microcontroller comprising one or more processors 1402 (e.g., microprocessor, microcontroller) coupled to at least one memory circuit 1404. The memory circuit 1404 stores machine-executable instructions that, when executed by the processor 1402, cause the processor 1402 to execute machine instructions to implement various processes described herein. The processor 1402 may be any one of a number of single-core or multi-core processors known in the art. The memory circuit 1404 may comprise volatile and non-volatile storage media. The processor 1402 may include an instruction processing unit 1406 and an arithmetic unit 1408. The instruction processing unit 1406 may be configured to receive instructions from the memory circuit 1404 of this disclosure.

Figure 11D:
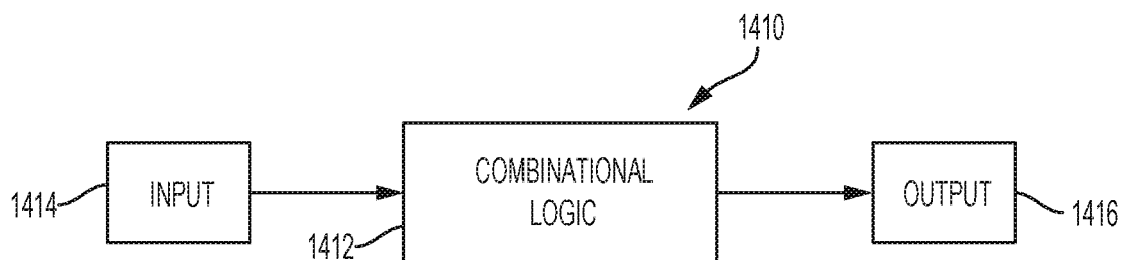
FIG. 11D illustrates a combinational logic circuit configured to control aspects of the user input device of FIG. 6, according to at least one aspect of the present disclosure.

FIG. 11D illustrates the combinational logic circuit 1410 that can be configured to control aspects of the input control device 1000, according to at least one aspect of this disclosure. The combinational logic circuit 1410 can be configured to implement various processes described herein. The combinational logic circuit 1410 may comprise a finite state machine comprising a combinational logic 1412 configured to receive data associated with the input control device 1000 (FIGS. 6-11) and a surgical visualization system and/or distance determining subsystem thereof from an input 1414, process the data by the combinational logic 1412, and provide an output 1416.

Figure 11E:
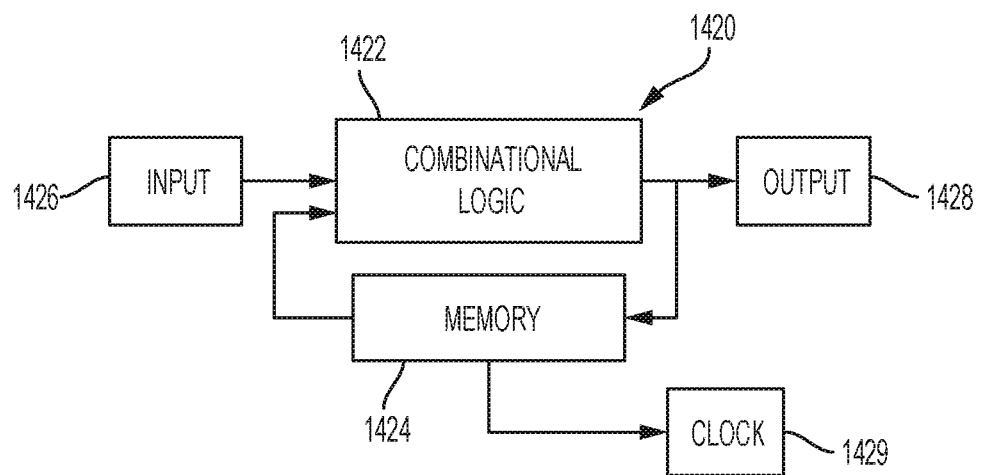
FIG. 11E illustrates a sequential logic circuit configured to control aspects of the user input device of FIG. 6, according to at least one aspect of the present disclosure.

FIG. 11E illustrates a sequential logic circuit 1420 configured to control aspects of the input control device 1000 (FIGS. 6-11), according to at least one aspect of this disclosure. For example, the sequential logic circuit 1420 or the combinational logic 1422 can be configured to implement various processes described herein. The sequential logic circuit 1420 may comprise a finite state machine. The sequential logic circuit 1420 may comprise a combinational logic 1422, at least one memory circuit 1424, and a clock 1429, for example. The at least one memory circuit 1424 can store a current state of the finite state machine. In certain instances, the sequential logic circuit 1420 may be synchronous or asynchronous. The combinational logic 1422 is configured to receive data associated with the input control device 1000 (FIGS. 6-11) and a surgical visualization system and/or distance determining subsystem thereof from an input 1426, process the data by the combinational logic 1422, and provide an output 1428. In other aspects, the circuit may comprise a combination of a processor (e.g., processor 1402 in FIG. 11C) and a finite state machine to implement various processes herein. In other aspects, the finite state machine may comprise a combination of a combinational logic circuit (e.g., combinational logic circuit 1410 in FIG. 11D) and the sequential logic circuit 1420. Control circuits similar to the control circuits 1400, 1410, and 1420 can also be utilized to control various aspects of a surgical robot and/or surgical visualization system, as further described herein.

In various instances, the input control device 1000 is configured to operate in different modes, such as a gross mode and a precision mode, for example. The variation in control motions in the different modes can be accomplished by selecting a preset scaling profile. For example, control motions with the multi-dimensional space joint 1006 can be scaled up for gross mode such that small forces on the space joint 1006 result in significant displacements of the end effector. Moreover, the control motions with the wrist 1010 can be scaled down for precision mode such that large moments at the wrist 1010 result in fine rotational displacements of the end effector. The preset scaling profile can be user-selected and/or depend on the type and/or complexity of a surgical procedure and/or the experience of the surgeon, for example. Alternative operational modes and settings are also contemplated.

Referring again to FIG. 11A, in certain instances, the first mode 1070 can correspond to a gross control mode and the second mode 1072 can correspond to a precision control mode. One or more user inputs to the space joint 1006 can correspond to control inputs to affect gross motion of the surgical tool in the first mode 1070, such as the large displacements of the surgical tool toward the surgical site. One or more inputs to the wrist 1010 can define the rotational displacements of the surgical tool, such as the rolling rotary displacement of the surgical end effector at the surgical site. The segmented controls can be selectively locked out, such that rolling rotational inputs at the wrist 1010 are disabled during portions of a surgical procedure and one or more inputs at the space joint 1006 are disabled during other portions of the surgical procedure. For example, it can be desirable to lock out the rolling rotational inputs during the first mode 1070, such as when the surgical end effector is positioned outside a threshold proximity zone around a surgical site and/or critical structure. Moreover, in various instances, the control motions for the space joint 1006 and/or the wrist 1010 can be scaled up or down based on input from the distance determining system. The scaling parameters for the control motions provided to the space joint 1006 and the wrist 1010 can be different in the first mode 1070 and the second mode 1072. For example, the velocity of the robotic tool can be slowed down during a precision motion mode and sped up during a gross motion mode.

Referring now to FIG. 11B, a table depicting scaling scenarios in various operational modes is depicted. An input control device, such as the input control device 1000 (FIGS. 6-11) can be configured to receive at least six different inputs (e.g. Input A, Input B, etc.) corresponding to six degrees of freedom of a surgical tool coupled thereto. The inputs can be scaled based on the operational mode (e.g. the first mode 1070, the second mode 1072, etc.), which is determined by an input to the control circuit, such as proximity data from a distance determining subsystem of a surgical visualization system, for example. A first list of rules 1074 comprises first control parameters for controlling the surgical tool based on input from the input control device 1000. A second list of rules 1076 comprise second control parameters for controlling the surgical tool based on input from the input control device 1000. In certain instances, such as when an input is "locked out", the variable value in the list of rules 1074, 1076 can be zero. Additional modes and additional rules/control parameters are contemplated.

In various aspects, the gross motions described in the present disclosure are gross translational motions characterized by speeds selected from a range of about 3 inches/second to about 4 inches/second. In at least one example, a gross translational motion, in accordance with the present disclosure, is about 3.5 inches/second. In various aspects, by contrast, the fine motions described in the present disclosure can be fine translational motions characterized by speeds less than or equal to 1.5 inch/second. In various aspects, the fine motions described in the present disclosure can be fine translational motions characterized by speeds selected from a range of about 0.5 inches/second to about 2.5 inches/second.

In various aspects, the gross motions described in the present disclosure are gross rotational motions characterized by speeds selected from a range of about 10 radians/second to about 14 radians/second. In at least one example, a gross rotational motion, in accordance with the present disclosure, is about 12.6 radians/second. In various aspects, by contrast, the fine motions described in the present disclosure can be fine rotational motions characterized by speeds selected from a range of about 2 radians/second to about 4 radians/second. In at least one example, a fine rotational motion, in accordance with the present disclosure, is about 2.3 radians/second.

In various aspects, the gross motions of the present disclosure are two to six times greater than the fine motions. In various aspects, the gross motions of the present disclosure are three to five times greater than the fine motions.

As described herein, the space joint 1006 can define input control motions for six degrees of freedom. For example, the space joint 1006 can define the input control motions for non-rotational translation of the surgical tool in three-dimensional space and rotation of the surgical tool about three different axes. In such instances, the joystick 1008 is configured to receive inputs in three-dimensional space and about three axes of rotation. Moreover, the end effector actuator 1020 (e.g. a jaw closure mechanism) is built into a six degree-of-freedom joystick assembly comprising the joystick 1008 and associated sensors in the base 1004. The input control motions from the space joint 1006 can be selectively locked out and/or scaled during different portions of a surgical procedure.

An exemplary six-degree of freedom input control device 1100 is depicted in FIGS. 18-22. In various instances, such an input device can be incorporated into a user input device for a surgical robot, such as the input control device 1000 (FIGS. 6-11), for example. The input control device 1100 includes a frame or base 1101, which typically remains stationary on a surface such as a desk or table during use, and a cap 1102, which is movably mounted on the base 1101 and forms the input mechanism by which a user may input movements that are detected and interpreted by the input control device 1100. In particular, the cap 1102 of the input control device 1100 is designed to be grasped by the user and manipulated relative to the base 1101 to generate the desired input. To determine the relative movements or positions of the cap 1102 and base 1101, the input control device 1100 includes a first board member 1110 fixed relative to the base 1101 of the input control device 1100, a second board member 1120 resiliently mounted in spaced relation to the first board member 1110 and adapted for movement or displacement relative thereto, and a plurality of optoelectronic measuring cells 1118 for determining relative movements or displacements between the first and second board members 1110, 1120. The second board member 1120 is elastically connected to the first board 1110 by a plurality of equally-spaced coil spring elements 1106.

Each of the measuring cells 1118 for determining the relative movements and/or positions of the first and second boards 1110, 1120 comprises a light emitting element in the form of an infrared light-emitting diode (ILED) 1113 (FIGS. 18 and 19) projecting from on an upper side the first board 1110 and a position-sensitive infrared detector (PSID) 1123 (FIG. 20) mounted on an underside of the second board 1120 and facing the first board 1110. Furthermore, a light shield housing 1130 is provided between the first board 1110 and the second board 1120 for effectively housing the ILEDs 1113 and for shielding the PSIDs 1123 from any unwanted or extraneous light that might otherwise affect the accuracy of the readings the PSIDs 1123 provide.

Figure 19:
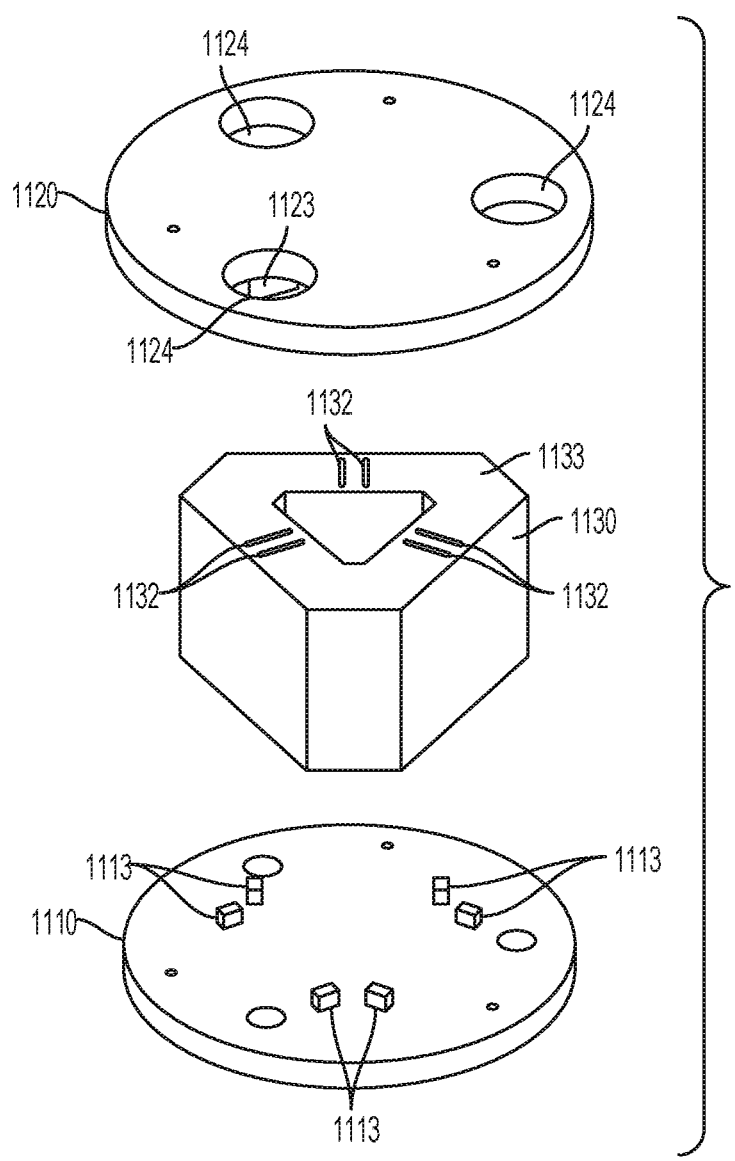
FIG. 19 is an exploded top perspective view of the first and second board members and the light shield of FIG. 18, according to at least one aspect of the present disclosure.

The light shield housing 1130 has a generally hollow structure with a number of cavities 1131 defined therein that form individual light-path channels between each ILED 1113 on the first board 1110 and its respective PSID 1123 mounted on the second board 1120. Furthermore, as shown in FIG. 19, the light shield housing 1130 includes slit diaphragms 1132 formed in a top wall 1133 thereof such that each of the slit diaphragms 1132 is arranged in the light-path between an ILED 1113 and the respective PSID 1123 that the ILED 1113 is intended to illuminate.

The light shield housing 1130 is thus configured to define a plurality of light beam paths between the ILEDs 1113 on the first board 1110 and the PSIDs 1123 on the second board 1120, such that each of the light beam paths is arranged to extend at an angle in the range of about 30° to about 60° (and preferably at about 45°) relative to the plane of the first board 1110, i.e. relative to a base reference plane for the input control device 1100. Furthermore, the light beam paths which are defined by the light-path channels 1131 formed along each side of the light shield housing 1130 thereby extend in three separate, intersecting planes corresponding to the planes of the housing sides. That is, the light beam paths of the two measuring cells 1118 having a common PSID 1123 may be considered to lie within the same plane. The light shield housing 1130 is thereby designed to form a three-dimensional array of light beam paths between the ILEDs 1113 and the PSIDs 1123. This, in turn, provides for a particularly compact optoelectronic device 1100, while also affording great flexibility in modifications to the shape of the light shield housing 1130.

Figure 20:
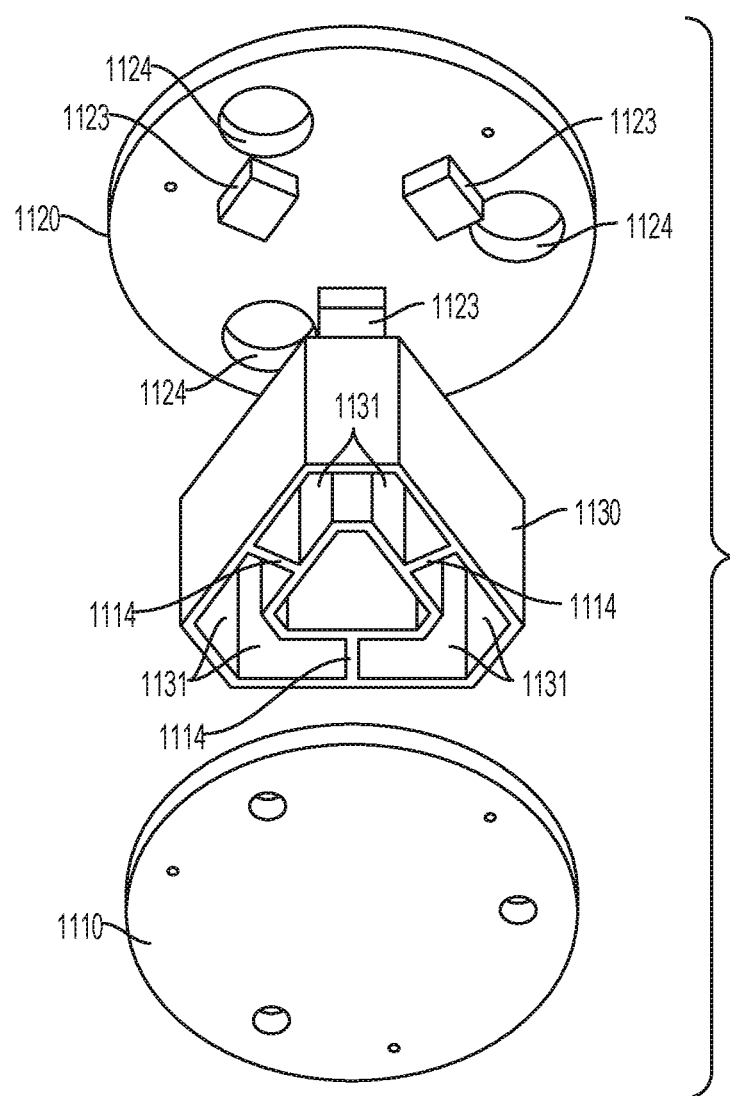
FIG. 20 is an exploded bottom perspective view of the first and second board members and the light shield of FIG. 19, according to at least one aspect of the present disclosure.

With further reference to FIG. 20, because each of the PSIDs 1123 is illuminated by two separate ILEDs 1113, each of the sides of the generally three-sided light shield housing 1130 is divided into two separate light-path channels 1131 by a central dividing wall 1114. In this way, each PSID 1123 is illuminated by its two separate ILEDs 1113 via two separate slit diaphragms 1132. Each of the slits 1132 provides optical communication with the associated PSID for only one of the ILEDs 1113. That is, each ILED 1113 is provided with its own dedicated slit diaphragm 1132. The slit diaphragms 1132 of each pair are arranged substantially parallel and extend generally perpendicular to a light-sensitive part of the associated PSID 1123.

Figure 18:
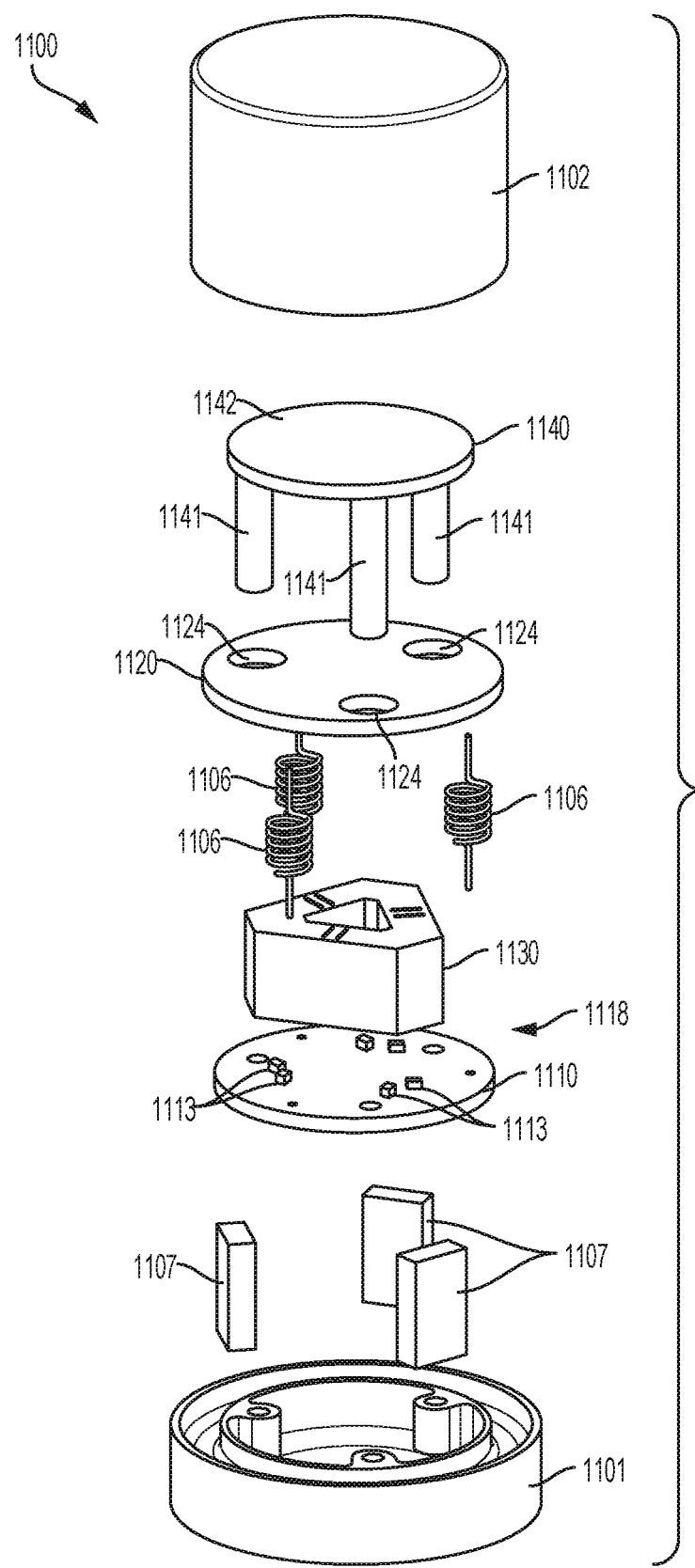
FIG. 18 is an exploded perspective view of an input device including first and second board members, a light shield, a stop arrangement, and a cap, according to at least one aspect of the present disclosure.

Referring primarily to FIG. 18, the optoelectronic device 1100 further includes a stop arrangement 1140, which is designed to provide a physical barrier to movement or displacement of the second board 1120 relative to the first board 1110 beyond a specific predetermined limit. The stop arrangement 1140 thereby prevents any inadvertent overloading of the input control device 1100 during use. The stop arrangement 1140 includes a plate-like connecting member 1142 and pin member 1141.

Figure 21:
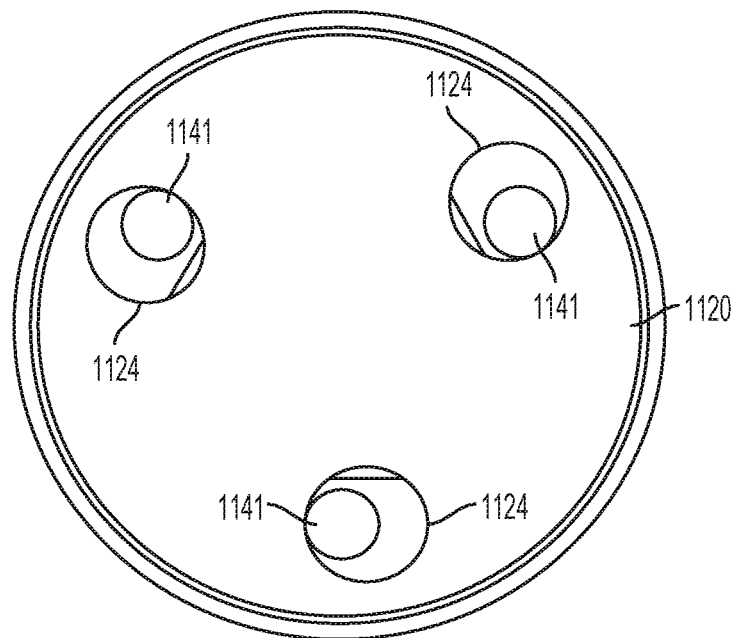
FIG. 21 is a plan view of pin members of the stop arrangement of FIG. 18 positioned in openings in the second board member of FIG. 18 in a rotated configuration, according to at least one aspect of the present disclosure.

Openings or holes 1124 formed through the second board 1120 have a diameter substantially larger than the diameter of the pin members 1141 they receive. In the neutral position of the second board 1120 relative to the first board 1110, each of the pin members 1141 can be positioned substantially centrally in its respective hole 1124 through the second board 1120. By virtue of the resilient deformability of the three coil spring elements 1106 connecting the board members 1110, 1120, the second board 1120 is able to move laterally and rotationally in a plane parallel to the first board 1110 within the limits defined by the holes 1124 and the sides of the pin members 1141. As shown in FIG. 21, as the second board 1120 is rotated counterclockwise from its neutral position relative to the first board 1110 against the bias of the coil spring elements 1106, the edges of the holes 1124 eventually engage the lateral sides of the pin members 1141, which in turn act as a stop and prevent further rotation of the second board 1120. The same effect naturally also occurs for clockwise rotations or lateral translations of the second board 1120. In various instances, elastomeric elements 1107 in the form of foam blocks, for example, can form a cushion for the pin members 1141 of the stop arrangement 1140.

Figure 22:
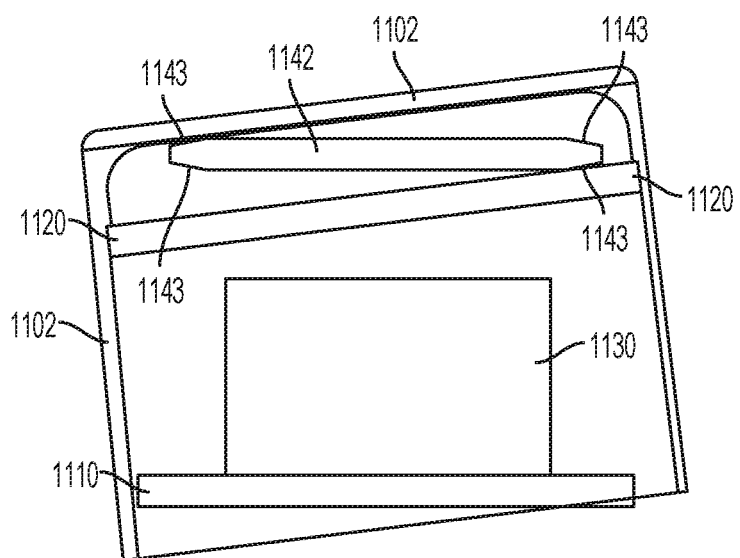
FIG. 22 is cross-sectional elevation view of the first and second board members, the light shield, the stop arrangement, and the cap of FIG. 18 in a tilted configuration, according to at least one aspect of the present disclosure.

With particular reference to FIG. 22, when a tilting (i.e. rotational) movement is applied to the second board 1120 (via the cap 1102) as shown, the second board 1120 will deflect until, after a predetermined amount of tilting has occurred, the second board 1120 engages the plate-like connecting member 1142 in an angled peripheral region 1143. The contact or engagement with the angled peripheral region 1143 of the fixed plate-like connecting member 1142 acts to stop further relative movement of the second board 1120 in that direction. Simultaneously, or even alternatively, an upper inside surface of the cap 1102 may engage a corresponding angled peripheral region 1143 of the plate-like connecting member 1142 as indicated in FIG. 22. The first board 1110, the light shield housing 1130 and the stop arrangement 1140 can all remain stationary relative to the frame of the input control device 1100, while the cap 1102 and the second board 1120 are moved relative thereto during operation of the device. The input control device 1100 as well as various alternative designs and/or features thereof are further described in European Patent Application No. 1,850,210, titled OPTOELECTRONIC DEVICE FOR DETERMINING RELATIVE MOVEMENTS OR RELATIVE POSITIONS OF TWO OBJECTS, published Oct. 31, 2007, which is incorporated by reference herein in its entirety.

Certain input control devices, such as the input devices at the surgeon's console 116 in FIGS. 1 and 2 can be bulky and require a large footprint within an operating room. Additionally, the surgeon can be required to stay in a predefined location (e.g. sitting at the surgeon's console 116) as long as the surgeon remains actively involved in the surgical procedure. Additionally, the ergonomics of the input control devices may be less than desirable for many surgeons and can be difficult to adjust and/or customize, which can take a toll on the health and longevity of the surgeon's career and/or lead to fatigue within a surgical case.

A compact input control device, which requires a smaller footprint, can be incorporated into an adjustable workspace rather than the surgeon's console 116. The adjustable workspace can allow a range of positioning of the input control device. In various instances, one or more compact input control devices can be positioned and/or moved around the operating room, such as near a patient table and/or within a sterile field, such that the surgeon can select a preferred position for controlling the robotic surgical procedure without being confined to a predefined location at a bulky surgeon's console. Moreover, the adaptability of the compact input control device can allow the input control device to be positioned at an adjustable workspace.

Figure 16:
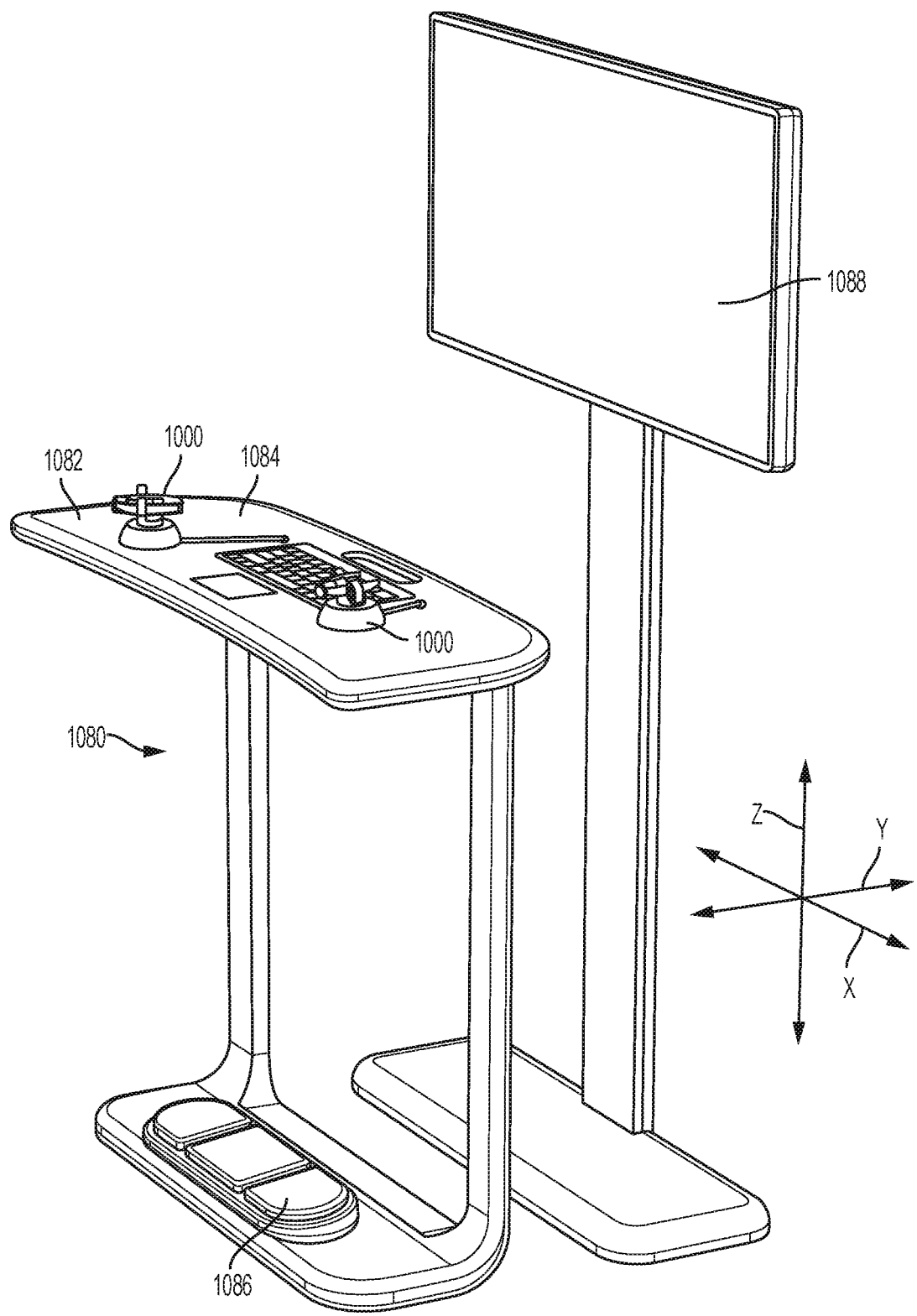
FIG. 16 is a perspective view of a workspace including two of the user input devices of FIG. 6 positioned on a surface, according to at least one aspect of the present disclosure.
Figure 17:
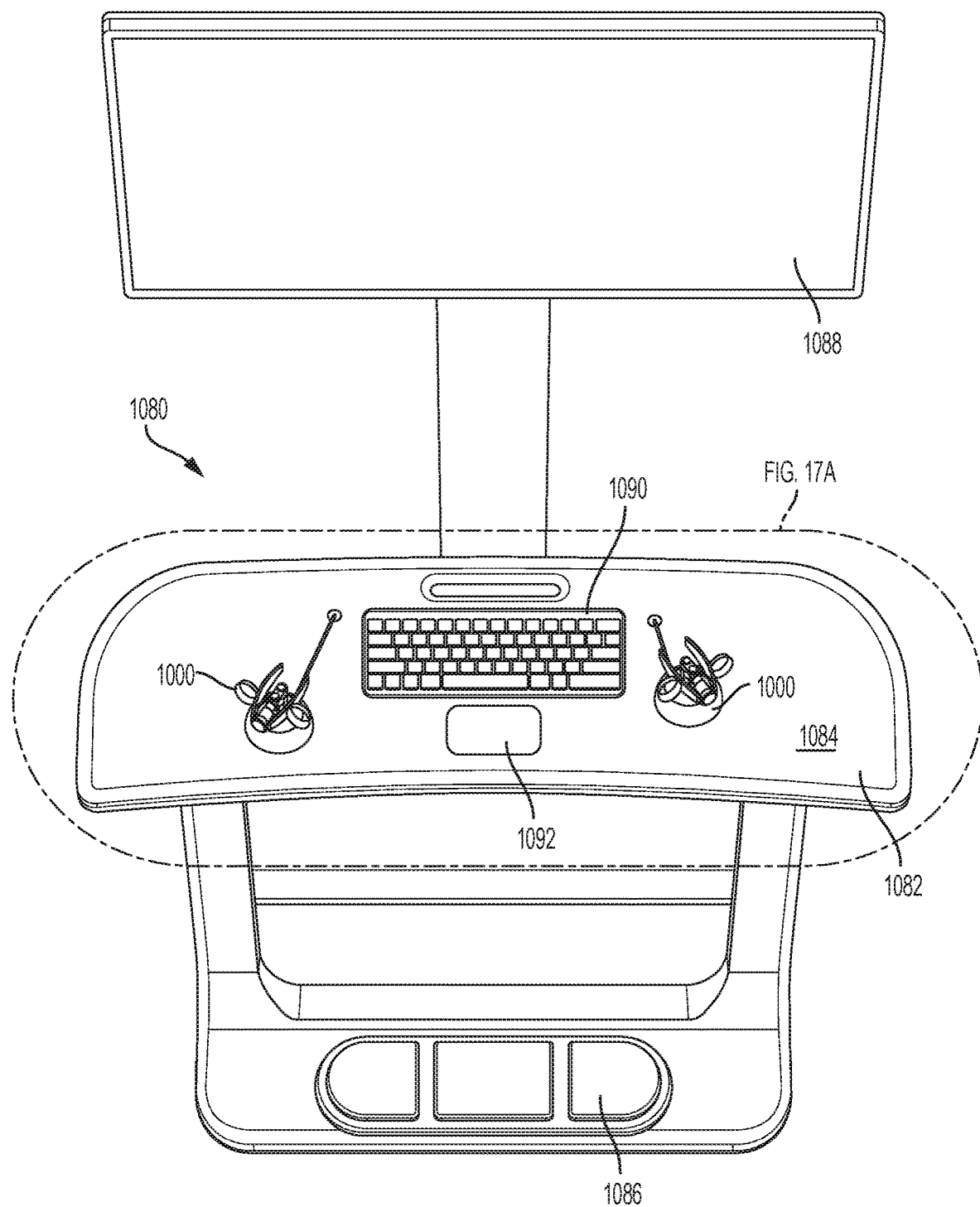
FIG. 17 is another perspective view of the workspace of FIG. 16, according to at least one aspect of the present disclosure.
Figure 17A:
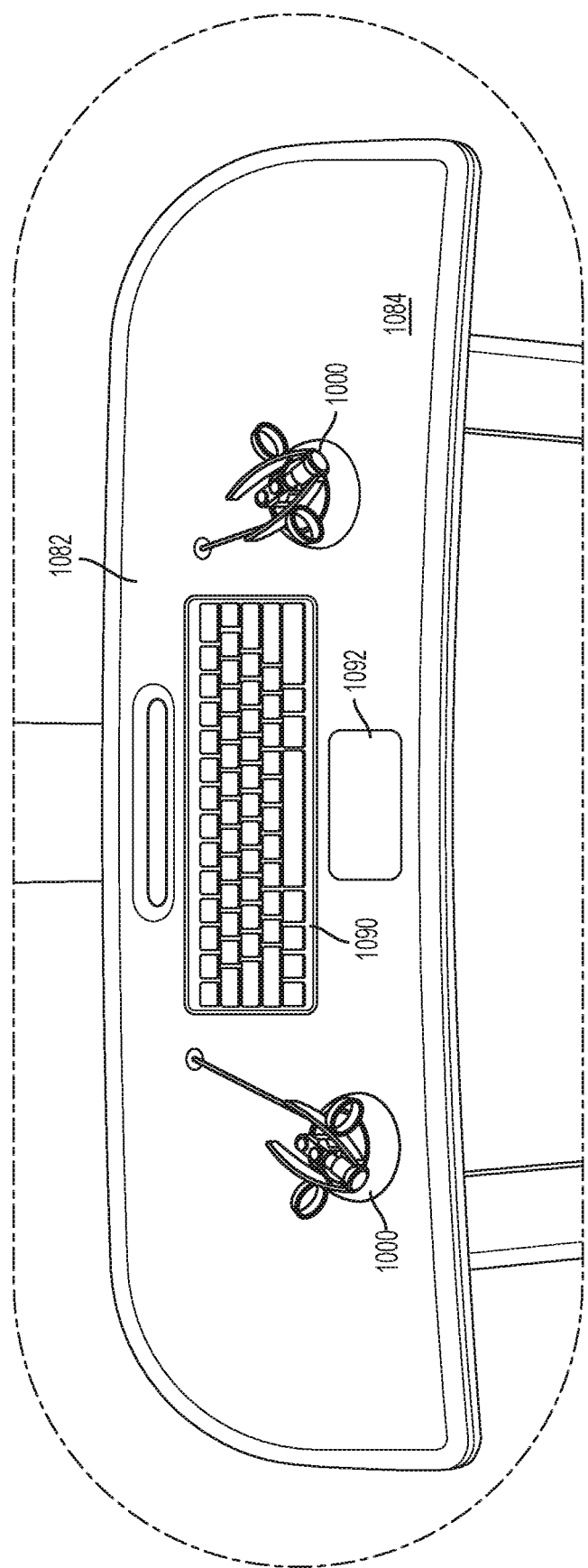
FIG. 17A is a detail view of a portion of the workspace of FIG. 17, according to at least one aspect of the present disclosure.

For example, referring now to FIGS. 16-17A, the input control device 1000 is incorporated into an adjustable workspace 1080 for a surgeon. The adjustable workspace 1080 includes a surface or desk 1082 and a monitor 1088 for viewing the surgical procedure via the endoscope. The desk 1082 and/or the monitor 1088 can be repositioned at different heights. In various instances, a first height can be selected such that the surgeon can stand at the desk 1082 and, at a different time, a second height can be selected such that the surgeon can sit at the desk 1082. Additionally or alternatively, the sitting and standing heights can be adjusted for different surgeons. Moreover, the desk 1082 can be moved relative to the monitor 1088 and the monitor 1088 can be moved relative to the desk 1082. For example, the desk 1082 and/or the monitor 1088 can be supported on releasably lockable wheels or casters. Similarly, a chair can be moved relative to the desk 1082 and the monitor 1088. In such instances, the X, Y, and Z positions of the various components of the adjustable workspace 1080 can be customized by the surgeon.

The desk 1082 includes a foot pedal board 1086; however, in other instances, a foot pedal board 1086 may not be incorporated into the desk 1082. In certain instances, the foot pedal board 1086 can be separate from the desk 1082, such that the position of the foot pedal board 1086 relative to the desk 1082 and/or chair can be adjustable as well.

In various instances, the adjustable workspace 1080 can be modular and moved toward the patient table or bedside. In such instances, the adjustable workspace 1080 can be draped with a sterile barrier and positioned within the sterile field. The adjustable workspace 1080 can house and/or support the processors and/or computers for implementing the teleoperation of the surgical robot from inputs to the input control device 1000 at the adjustable workspace 1080. Moreover, the desk 1082 includes a platform or surface 1084 that is suitable for supporting the arm(s)/wrist(s) of the surgeon with limited mechanical adjustments thereto.

Owing to the smaller size and reduced range of motion of the input control device 1000, as well as the adjustability of the workspace 1080, the surgeon's console can define a low profile and require a smaller footprint in the operating room. Smaller consoles can provide more space in the operating room. Additionally, the smaller footprint can allow multiple users (e.g. an experienced surgeon and less experienced surgeon or trainee, such as a medical student or resident) to cooperatively perform a surgical procedure in close proximity, which can facilitate training. The small input control devices can be utilized in a stimulator or real system, for example, and can be remote to the surgical theater and/or at the robotic surgical system.

Referring primarily to FIGS. 16 and 17A, the adjustable workspace 1080 also supports additional axillary devices. For example, a keyboard 1090 and a touchpad 1092 are supported on the surface 1084 of the desk 1082. Alternative axillary devices are also contemplated, such as a traditional computer mouse and other imaging and diagnostic equipment such as registered magnetic resonance imaging (MRI) or computerized tomography (CT) scan data, images, and medical histories, for example. The axillary devices can control the graphical user interface on the monitor 1088, and the input control devices 1000 can control the teleoperation of the surgical robot. In such instances, the two distinct control inputs allow the surgeon to control teleoperation functions using the clutch-less, input control device(s) 1000 while engaging with the graphical user interface on the monitor 1088 with more conventional techniques. As a result, the user can interact with applications on the monitor 1088 concurrently with the teleoperation of the surgical robot. Moreover, the dual, segregated control input creates a clear cognitive distinction between the teleoperation environment and the graphical user interface environment.

In various instances, an adjustable workspace for the surgeon can be desired. For example, the surgeon may want to be free and/or untethered and/or unconfined to a predefined location at the surgeon's console, as further described herein. In certain instances, a surgeon may want to relocate during a surgical procedure. For example, a surgeon may want to "scrub in" quickly during a surgical procedure and enter the sterile field in order to view the surgical procedure and/or the patient in-person, rather than on a video monitor. Moreover, a surgeon may not want to give up control of the surgical robot as the surgeon relocates.

A mobile input control device can allow the surgeon to relocate and even enter the sterile field during a surgical procedure. The mobile input control device can be modular, for example, and compatible with different docking stations within an operating room. In various instances, the mobile portion of the input control device can be a single-use device, which can be sterilized for use within the sterile field.

Figure 23:
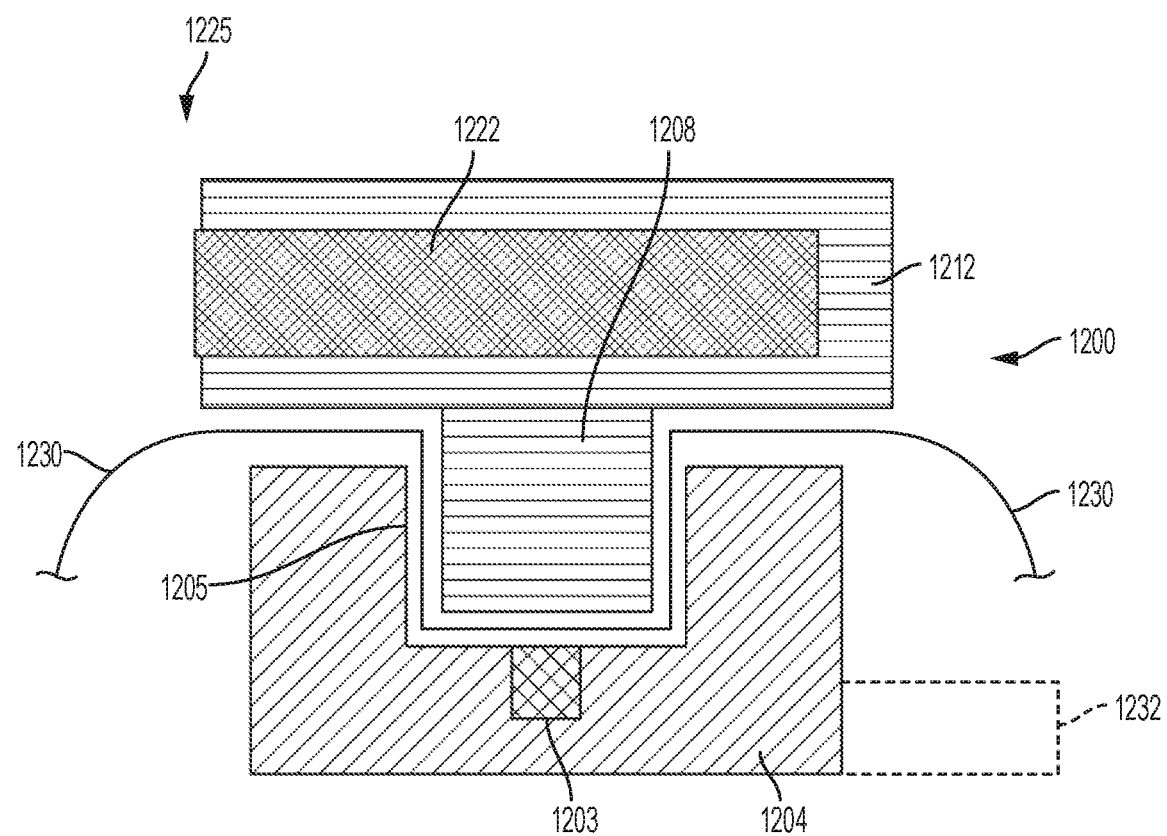
FIG. 23 is a cross-sectional elevation view of a user input device, according to at least one aspect of the present disclosure.

As an example, referring now to FIG. 23, an input control device 1200 is shown. The input control device 1200 includes a base 1204, which is similar to the base 1004 of the input control device 1000 in many respects. The input control device 1200 can include a multi-axis force and torque sensor 1203, as described herein, which is configured to detect forces and moments applied to the base 1204 by a modular joystick component 1208, which is similar to the joystick 1008 in many respects. The modular joystick component 1208 can be releasably docked in the base 1204 to apply forces for detection by the sensor 1203 housed therein. A shaft 1212, which is similar to the shaft 1012 in many respects, extends from the joystick 1208 and supports at least one movable finger 1222, which is similar to the fingers 1022 in many respects. Similar to the input control device 1000, the input control device 1200 can also include a wrist rotatably coupled to the modular joystick component 1208, which can be rotated to supply control motions such as a rolling control motion for a surgical end effector. For example, the shaft 1212 can include a wrist component at a proximal end 1225 thereof.

In operation, the input control device 1200 can be engaged by the hand of a surgeon. Forces applied by the surgeon's hand are detected and corresponding signals are conveyed to a control unit for controlling a robotic surgical tool in signal communication with the input control device 1200. In such instances, forces applied in the X, Y, and Z directions can correspond to translation of the end effector of the surgical tool in the X, Y, and Z directions, and moments about the X, Y, and Z axes can correspond to rotation of the end effector about the X, Y, and Z axes. In various instances, controls by the input control device 1200 can be segmented based on the detected input and/or position of the end effector at the surgical site (e.g. proximity to an anatomical and/or critical structure).

The input control device 1200 includes separable components including the base 1204, which is separable from the modular joystick component 1208. In certain instances, the modular joystick component 1208 can nest and/or fit within an opening 1205 in the base 1204. In various instances, the joystick 1208 and the base 1204 can mechanically and electrically couple. In various instances, the opening 1205 in the base 1204 can include a registration key, which allows the joystick component 1208 to be received within the opening 1205 at a set angular orientation, such that the position of the modular joystick component 1208 relative to the base 1204 is known.

In various instances, the modular joystick component 1208 and the base 1204 can include communication modules that enable communication therebetween. Because the communication does not require high powered signals, near-field communication protocols can be utilized in various instances. A sterile barrier 1230 can extend between the modular components of the input control device 1200. The sterile barrier 1230 is a thin and flexible sheet positioned between the modular components, for example. Near-field communication signals can travel through such a layer of material. The sterile barrier 1230 can define a drape or sheet that covers the base 1204, for example. In one aspect, the drape can include a thin element of plastic or elastomeric material for positioning, location, and transference of forces.

In certain instances, the base 1204 can be positioned in the sterile field during a surgical procedure. For example, the base 1204 can be mounted onto a bedrail 1232 and/or table adjacent to the patient. In certain instances, the base 1204 can be a reusable or multi-use component of the input control device 1200. A plurality of bases 1204 can be positioned around a surgical theater, such as a remote surgeon's console outside the sterile field and on the patient table within the sterile field, among other locations, for example.

The joystick component 1208 can be compatible with each base 1204. In various instances, the joystick component 1208 can be a disposable and/or single-use component. In other instances, the joystick component 1208 can be re-sterilized between uses. For example, the joystick component 1208 can be sterilized (e.g. low-temperature sterilization) and sealed prior to use. When the surgeon moves into the sterile field during a surgical procedure, the sealed joystick component 1208 can be unsealed and ready to use. After the use, the joystick component 1208 can be disposed and/or sterilized for a subsequent use.

Visualization Systems

"Digital surgery" can embrace robotic systems, advanced imaging, advanced instrumentation, artificial intelligence, machine learning, data analytics for performance tracking and benchmarking, connectivity both inside and outside of the operating room (OR), and more. Although various surgical platforms described herein can be used in combination with a robotic surgical system, such surgical platforms are not limited to use with a robotic surgical system. In certain instances, advanced surgical visualization can occur without robotics, without the telemanipulation of robotic tools, and/or with limited and/or optional robotic assistance. Similarly, digital surgery can occur without robotics, without the telemanipulation of robotic tools, and/or with limited and/or optional robotic assistance.

In one instance, a surgical visualization system can include a first light emitter configured to emit a plurality of spectral waves, a second light emitter configured to emit a light pattern, and one or more receivers, or sensors, configured to detect visible light, molecular responses to the spectral waves (spectral imaging), and/or the light pattern. The surgical visualization system can also include an imaging system and a control circuit in signal communication with the receiver(s) and the imaging system. Based on output from the receiver(s), the control circuit can determine a geometric surface map, i.e. three-dimensional surface topography, of the visible surfaces at the surgical site and one or more distances with respect to the surgical site. In certain instances, the control circuit can determine one more distances to an at least partially concealed structure. Moreover, the imaging system can convey the geometric surface map and the one or more distances to a clinician. In such instances, an augmented view of the surgical site provided to the clinician can provide a representation of the at least partially concealed structure within the relevant context of the surgical site. For example, the imaging system can virtually augment the concealed structure on the geometric surface map of the concealing and/or obstructing tissue similar to a line drawn on the ground to indicate a utility line below the surface. Additionally or alternatively, the imaging system can convey the proximity of one or more surgical tools to the visible and obstructing tissue and/or to the at least partially concealed structure and/or the depth of the concealed structure below the visible surface of the obstructing tissue. For example, the visualization system can determine a distance with respect to an augmented line on the surface of the visible tissue and convey the distance to the imaging system. In various instances, the surgical visualization system can gather data and convey information intraoperatively.

Figure 24:
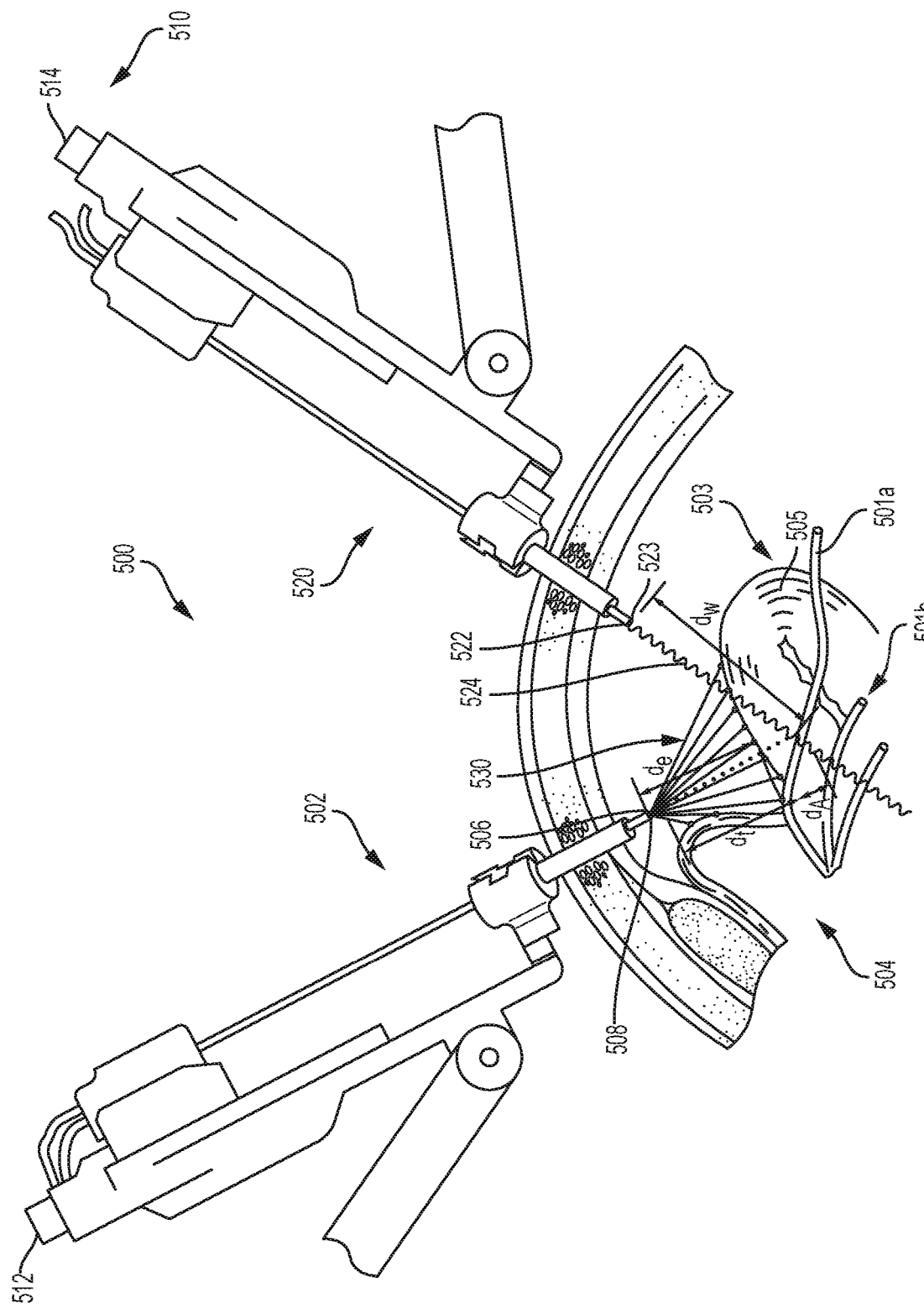
FIG. 24 is a schematic of a surgical visualization system including an imaging device and a surgical device, the surgical visualization system configured to identify a critical structure below a tissue surface, according to at least one aspect of the present disclosure.

FIG. 24 depicts a surgical visualization system 500 according to at least one aspect of the present disclosure. The surgical visualization system 500 may be incorporated into a robotic surgical system, such as a robotic system 510. The robotic system 510 can be similar to the robotic system 110 (FIG. 1) and the robotic system 150 (FIG. 3) in many respects. Alternative robotic systems are also contemplated. The robotic system 510 includes at least one robotic arm, such as the first robotic arm 512 and the second robotic arm 514. The robotic arms 512, 514 include rigid structural members and joints, which can include servomotor controls. The first robotic arm 512 is configured to maneuver a surgical device 502, and the second robotic arm 514 is configured to maneuver the imaging device 520. A robotic control unit can be configured to issue control motions to the robotic arms 512, 514, which can affect the surgical device 502 and an imaging device 520, for example. The surgical visualization system 500 can create a visual representation of various structures within an anatomical field. The surgical visualization system 500 can be used for clinical analysis and/or medical intervention, for example. In certain instances, the surgical visualization system 500 can be used intraoperatively to provide real-time, or near real-time, information to the clinician regarding proximity data, dimensions, and/or distances during a surgical procedure.

In certain instances, a surgical visualization system is configured for intraoperative, real-time identification of one or more critical structures, such as critical structures 501a, 501b in FIG. 24 and/or to facilitate the avoidance of the critical structure(s) 501a, 501b by a surgical device. In other instances, critical structures can be identified preoperatively. In this example, the critical structure 501a is a ureter and the critical structure 501b is a vessel in tissue 503, which is an organ, i e the uterus. Alternative critical structures are contemplated and numerous examples are provided herein. By identifying the critical structure(s) 501a, 501b, a clinician can avoid maneuvering a surgical device too close to the critical structure(s) 501a, 501b and/or into a region of predefined proximity to the critical structure(s) 501a, 501b during a surgical procedure. The clinician can avoid dissection of and/or near a vein, artery, nerve, and/or vessel, for example, identified as the critical structure, for example. In various instances, the critical structures can be determined on a procedure-by-procedure basis. The critical structures can be patient specific.

Critical structures can be structures of interest. For example, critical structures can include anatomical structures such as a ureter, an artery such as a superior mesenteric artery, a vein such as a portal vein, a nerve such as a phrenic nerve, and/or a tumor, among other anatomical structures. In other instances, a critical structure can be a foreign structure in the anatomical field, such as a surgical device, surgical fastener, clip, tack, bougie, band, and/or plate, for example. Critical structures can be determined on a patient-by-patient and/or a procedure-by-procedure basis. Example critical structures are further described herein and in U.S. patent application Ser. No. 16/128,192, titled VISUALIZATION OF SURGICAL DEVICES, filed Sep. 11, 2018, which is incorporated by reference herein in its entirety.

Referring again to FIG. 24, the critical structures 501a, 501b may be embedded in tissue 503. Stated differently, the critical structures 501a, 501b may be positioned below the surface 505 of the tissue 503. In such instances, the tissue 503 conceals the critical structures 501a, 501b from the clinician's view. The critical structures 501a, 501b are also obscured from the view of the imaging device 520 by the tissue 503. The tissue 503 can be fat, connective tissue, adhesions, and/or organs, for example. In various instances, the critical structures 501a, 501b can be partially obscured from view.

FIG. 24 also depicts the surgical device 502. The surgical device 502 includes an end effector having opposing jaws extending from the distal end of the shaft of the surgical device 502. The surgical device 502 can be any suitable surgical device such as, for example, a dissector, a stapler, a grasper, a clip applier, and/or an energy device including mono-polar probes, bi-polar probes, ablation probes, and/or an ultrasonic end effector. Additionally or alternatively, the surgical device 502 can include another imaging or diagnostic modality, such as an ultrasound device, for example. In one aspect of the present disclosure, the surgical visualization system 500 can be configured to achieve identification of one or more critical structures and the proximity of the surgical device 502 to the critical structure(s).

The surgical visualization system 500 includes an imaging subsystem that includes an imaging device 520, such as a camera, for example, configured to provide real-time views of the surgical site. The imaging device 520 can include a camera or imaging sensor that is configured to detect visible light, spectral light waves (visible or invisible), and/or a structured light pattern (visible or invisible), for example. In various aspects of the present disclosure, the imaging system can include an imaging device such as an endoscope, for example. Additionally or alternatively, the imaging system can include an imaging device such as an arthroscope, angioscope, bronchoscope, choledochoscope, colonoscope, cytoscope, duodenoscope, enteroscope, esophagogastro-duodenoscope (gastroscope), laryngoscope, nasopharyngo-neproscope, sigmoidoscope, thoracoscope, ureteroscope, or exoscope, for example. In other instances, such as in open surgery applications, the imaging system may not include a scope.

The imaging device 520 of the surgical visualization system 500 can be configured to emit and detect light at various wavelengths, such as, for example, visible light, spectral light wavelengths (visible or invisible), and a structured light pattern (visible or invisible). The imaging device 520 may include a plurality of lenses, sensors, and/or receivers for detecting the different signals. For example, the imaging device 520 can be a hyperspectral, multispectral, or selective spectral camera, as further described herein. The imaging device 520 can also include a waveform sensor 522 (such as a spectral image sensor, detector, and/or three-dimensional camera lens). For example, the imaging device 520 can include a right-side lens and a left-side lens used together to record two two-dimensional images at the same time and, thus, generate a three-dimensional image of the surgical site, render a three-dimensional image of the surgical site, and/or determine one or more distances at the surgical site. Additionally or alternatively, the imaging device 520 can be configured to receive images indicative of the topography of the visible tissue and the identification and position of hidden critical structures, as further described herein. For example, the field of view of the imaging device 520 can overlap with a pattern of light (structured light) formed by light arrays 530 projected on the surface 505 of the tissue 503, as shown in FIG. 24.

Views from the imaging device 520 can be provided to a clinician and, in various aspects of the present disclosure, can be augmented with additional information based on the tissue identification, landscape mapping, and the distance sensor system 504. In such instances, the surgical visualization system 500 includes a plurality of subsystems—an imaging subsystem, a surface mapping subsystem, a tissue identification subsystem, and/or a distance determining subsystem, as further described herein. These subsystems can cooperate to intraoperatively provide advanced data synthesis and integrated information to the clinician(s) and/or to a control unit. For example, information from one or more of these subsystems can inform a decision-making process of a clinician and/or a control unit for an input control device of the robotic system.

The surgical visualization system 500 can include one or more subsystems for determining the three-dimensional topography, or surface maps, of various structures within the anatomical field, such as the surface of tissue. Exemplary surface mapping systems include Lidar (light radar), Structured Light (SL), three-dimensional (3D) stereoscopy (stereo), Deformable-Shape-from-Motion (DSfM), Shape-from-Shading (SfS), Simultaneous Localization and Mapping (SLAM), and Time-of-Flight (ToF). Various surface mapping systems are further described herein and in L. Maier-Hein et al., "Optical techniques for 3D surface reconstruction in computer-assisted laparoscopic surgery", Medical Image Analysis 17 (2013) 974-996, which is incorporated by reference herein in its entirety. The surgical visualization system 500 can also determine proximity to various structures within the anatomical field, including the surface of tissue, as further described herein.

In various aspect of the present disclosure, the surface mapping subsystem can be achieved with a light pattern system, as further described herein. The use of a light pattern (or structured light) for surface mapping is known. Known surface mapping techniques can be utilized in the surgical visualization systems described herein.

Structured light is the process of projecting a known pattern (often a grid or horizontal bars) on to a surface. U.S. Patent Application Publication No. 2017/0055819, titled SET COMPRISING A SURGICAL INSTRUMENT, published Mar. 2, 2017, and U.S. Patent Application Publication No. 2017/0251900, titled DEPICTION SYSTEM, published Sep. 7, 2017, disclose a surgical system comprising a light source and a projector for projecting a light pattern. U.S. Patent Application Publication No. 2017/0055819, titled SET COMPRISING A SURGICAL INSTRUMENT, published Mar. 2, 2017, and U.S. Patent Application Publication No. 2017/0251900, titled DEPICTION SYSTEM, published Sep. 7, 2017, are incorporated by reference herein in their respective entireties.

Figure 37:
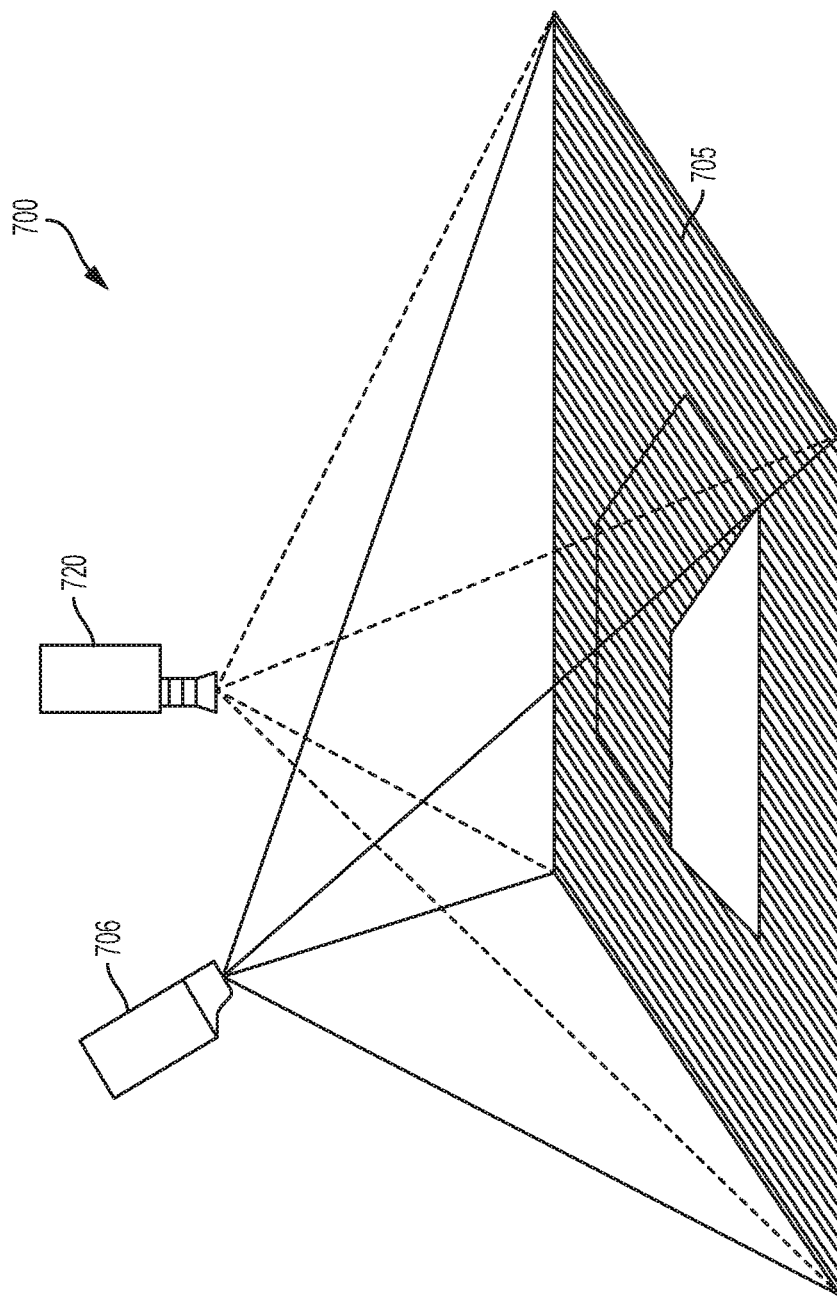
FIG. 37 is a schematic of a structured light source for a surgical visualization system, according to at least one aspect of the present disclosure.

FIG. 37 illustrates a structured (or patterned) light system 700, according to at least one aspect of the present disclosure. As described herein, structured light in the form of stripes or lines, for example, can be projected from a light source and/or projector 706 onto the surface 705 of targeted anatomy to identify the shape and contours of the surface 705. A camera 720, which can be similar in various respects to the imaging device 520 (FIG. 24), for example, can be configured to detect the projected pattern of light on the surface 705. The way that the projected pattern deforms upon striking the surface 705 allows vision systems to calculate the depth and surface information of the targeted anatomy.

In certain instances, invisible (or imperceptible) structured light can be utilized. The structured light can be used without interfering with other computer vision tasks for which the projected pattern may be confusing. For example, the frames with the light pattern can be isolated from the frames that are shown (e.g. augmented out). In still other instances, infrared light or extremely fast frame rates of visible light that alternate between two exact opposite patterns can be utilized to prevent interference.

Referring again to FIG. 24, in one aspect, the surgical visualization system 500 includes an emitter 506, which is configured to emit a pattern of light, such as stripes, grid lines, and/or dots, to enable the determination of the topography or landscape of the surface 505 of the tissue 503. For example, projected light arrays 530 can be used for three-dimensional scanning and registration on the surface 505 of the tissue 503. The projected light arrays 530 can be emitted from the emitter 506 located on the surgical device 502 and/or the robotic arm 512, 514 and/or the imaging device 520, for example. In one aspect, the projected light array 530 is employed to determine the shape defined by the surface 505 of the tissue 503 and/or the motion of the surface 505 intraoperatively. The imaging device 520 is configured to detect the projected light arrays 530 reflected from the surface 505 to determine the topography of the surface 505 and various distances with respect to the surface 505. One or more additional and/or alternative surface mapping techniques may also be employed.

In various aspects of the present disclosure, a tissue identification subsystem can be achieved with a spectral imaging system. The spectral imaging system can rely on hyperspectral imaging, multispectral imaging, or selective spectral imaging, for example. Hyperspectral imaging of tissue is further described in U.S. Pat. No. 9,274,047, titled METHODS AND APPARATUS FOR IMAGING OF OCCLUDED OBJECTS, issued Mar. 1, 2016, which is incorporated by reference herein in its entirety.

In various instances, the imaging device 520 is a spectral camera (e.g. a hyperspectral camera, multispectral camera, or selective spectral camera), which is configured to detect reflected spectral waveforms and generate a spectral cube of images based on the molecular response to the different wavelengths. Spectral imaging is further described herein.

In various instances, hyperspectral imaging technology, can be employed to identify signatures in anatomical structures in order to differentiate a critical structure from obscurants. Hyperspectral imaging technology may provide a visualization system that can provide a way to identify critical structures such as ureters and/or blood vessels, for example, especially when those structures are obscured by fat, connective tissue, blood, or other organs, for example. The use of the difference in reflectance of different wavelengths in the infrared (IR) spectrum may be employed to determine the presence of key structures versus obscurants. Referring now to FIGS. 38-40, illustrative hyperspectral signatures for a ureter, an artery, and nerve tissue with respect to obscurants such as fat, lung tissue, and blood, for example, are depicted.

FIG. 38 is a graphical representation 950 of an illustrative ureter signature versus obscurants. The plots represent reflectance as a function of wavelength (nm) for wavelengths for fat, lung tissue, blood, and a ureter. FIG. 39 is a graphical representation 952 of an illustrative artery signature versus obscurants. The plots represent reflectance as a function of wavelength (nm) for fat, lung tissue, blood, and a vessel. FIG. 40 is a graphical representation 954 of an illustrative nerve signature versus obscurants. The plots represent reflectance as a function of wavelength (nm) for fat, lung tissue, blood, and a nerve.

Referring again to FIG. 24, the imaging device 520 may include an optical waveform emitter 523 that is configured to emit electromagnetic radiation 524 (NIR photons) that can penetrate the surface 505 of the tissue 503 and reach the critical structures 501a, 501b. The imaging device 520 and the optical waveform emitter 523 thereon can be positionable by the robotic arm 512, 514. A corresponding waveform sensor 522 (an image sensor, spectrometer, or vibrational sensor, for example) on the imaging device 520 is configured to detect the effect of the electromagnetic radiation 524 received by the waveform sensor 522. The wavelengths of the electromagnetic radiation 524 emitted by the optical waveform emitter 523 can be configured to enable the identification of the type of anatomical and/or physical structure, such as the critical structures 501a, 501b. In one aspect, the wavelengths of the electromagnetic radiation 524 may be variable. The waveform sensor 522 and optical waveform emitter 523 may be inclusive of a multispectral imaging system and/or a selective spectral imaging system, for example.

The identification of the critical structures 501a, 501b can be accomplished through spectral analysis, photo-acoustics, and/or ultrasound, for example. In certain instances, the waveform sensor 522 and optical waveform emitter 523 may be inclusive of a photoacoustic imaging system, for example. In various instances, the optical waveform emitter 523 can be positioned on a separate surgical device from the imaging device 520. Alternative tissue identification techniques are also contemplated. In certain instances, the surgical visualization system 500 may not be configured to identify hidden critical structures.

In one instance, the surgical visualization system 500 incorporates tissue identification and geometric surface mapping in combination with a distance determining subsystems, such as the distance sensor system 504. The distance sensor system 504 is configured to determine one or more distances at the surgical site. The distance sensor system 504 is a time-of-flight system that is configured to determine the distance to one or more anatomical structures. Alternative distance determining subsystems are also contemplated. In combination, the tissue identification systems, geometric surface mapping, and the distance determining subsystem can determine a position of the critical structures 501a, 501b within the anatomical field and/or the proximity of a surgical device 502 to the surface 505 of the visible tissue 503 and/or to the critical structures 501a, 501b.

In various aspects of the present disclosure, the distance determining system can be incorporated into the surface mapping system. For example, structured light can be utilized to generate a three-dimensional virtual model of the visible surface and determine various distances with respect to the visible surface. In other instances, a time-of-flight emitter can be separate from the structured light emitter.

In various instances, the distance determining subsystem can rely on time-of-flight measurements to determine one or more distances to the identified tissue (or other structures) at the surgical site. In one aspect, the distance sensor system 504 may be a time-of-flight distance sensor system that includes an emitter, such as the emitter 506, and a receiver 508, which can be positioned on the surgical device 502. In one general aspect, the emitter 506 of the distance sensor system 504 may include a very tiny laser source and the receiver 508 of the distance sensor system 504 may include a matching sensor. The distance sensor system 504 can detect the "time of flight," or how long the laser light emitted by the emitter 506 has taken to bounce back to the sensor portion of the receiver 508. Use of a very narrow light source in the emitter 506 can enable the distance sensor system 504 to determine the distance to the surface 505 of the tissue 503 directly in front of the distance sensor system 504.

Referring still to FIG. 24, $d_e$ is the emitter-to-tissue distance from the emitter 506 to the surface 505 of the tissue 503 and $d_t$ is the device-to-tissue distance from the distal end of the surgical device 502 to the surface 505 of the tissue. The distance sensor system 504 can be employed to determine the emitter-to-tissue distance $d_e$. The device-to-tissue distance $d_t$ is obtainable from the known position of the emitter 506 on the shaft of the surgical device 502 relative to the distal end of the surgical device 502. In other words, when the distance between the emitter 506 and the distal end of the surgical device 502 is known, the device-to-tissue distance $d_t$ can be determined from the emitter-to-tissue distance $d_e$.

In various instances, the receiver 508 for the distance sensor system 504 can be mounted on a separate surgical device instead of the surgical device 502. For example, the receiver 508 can be mounted on a cannula or trocar through which the surgical device 502 extends to reach the surgical site. In still other instances, the receiver 508 for the distance sensor system 504 can be mounted on a separate robotically-controlled arm (e.g. the robotic arm 512, 514), on a movable arm that is operated by another robot, and/or to an operating room (OR) table or fixture. In certain instances, the imaging device 520 includes the time-of-flight receiver 508 to determine the distance from the emitter 506 to the surface 505 of the tissue 503 using a line between the emitter 506 on the surgical device 502 and the imaging device 520. For example, the distance $d_e$ can be triangulated based on known positions of the emitter 506 (e.g, on the surgical device 502) and the receiver 508 (e.g. on the imaging device 520) of the distance sensor system 504. The three-dimensional position of the receiver 508 can be known and/or registered to the robot coordinate plane intraoperatively.

In certain instances, the position of the emitter 506 of the distance sensor system 504 can be controlled by the first robotic arm 512 and the position of the receiver 508 of the distance sensor system 504 can be controlled by the second robotic arm 514. In other instances, the surgical visualization system 500 can be utilized apart from a robotic system. In such instances, the distance sensor system 504 can be independent of the robotic system.

In certain instances, one or more of the robotic arms 512, 514 may be separate from a main robotic system used in the surgical procedure. At least one of the robotic arms 512, 514 can be positioned and registered to a particular coordinate system without servomotor control. For example, a closed-loop control system and/or a plurality of sensors for the robotic arms 512, 514 can control and/or register the position of the robotic arm(s) 512, 514 relative to the particular coordinate system. Similarly, the position of the surgical device 502 and the imaging device 520 can be registered relative to a particular coordinate system.

Referring still to FIG. 24, $d_W$ is the camera-to-critical structure distance from the optical waveform emitter 523 located on the imaging device 520 to the surface of the critical structure 501a, and $d_A$ is the depth of the critical structure 501b below the surface 505 of the tissue 503 (i.e., the distance between the portion of the surface 505 closest to the surgical device 502 and the critical structure 501b). In various aspects, the time-of-flight of the optical waveforms emitted from the optical waveform emitter 523 located on the imaging device 520 can be configured to determine the camera-to-critical structure distance $d_W$. The use of spectral imaging in combination with time-of-flight sensors is further described herein.

In one aspect, the surgical visualization system 500 is configured to determine an emitter-to-tissue distance $d_e$ from an emitter 506 on the surgical device 502 to a surface 505 of the uterus via structured light. The surgical visualization system 500 is configured to extrapolate a device-to-tissue distance $d_t$ from the surgical device 502 to the surface 505 of the uterus based on the emitter-to-tissue distance $d_e$. The surgical visualization system 500 is also configured to determine a tissue-to-ureter distance $d_A$ from the critical structure (the ureter) 501a to the surface 505 and a camera-to ureter distance $d_W$ from the imaging device 520 to the critical structure (the ureter) 501a. As described herein, the surgical visualization system 500 can determine the distance $d_W$ with spectral imaging and time-of-flight sensors, for example. In various instances, the surgical visualization system 500 can determine (e.g. triangulate) the tissue-to-ureter distance $d_A$ (or depth) based on other distances and/or the surface mapping logic described herein.

Figure 29:
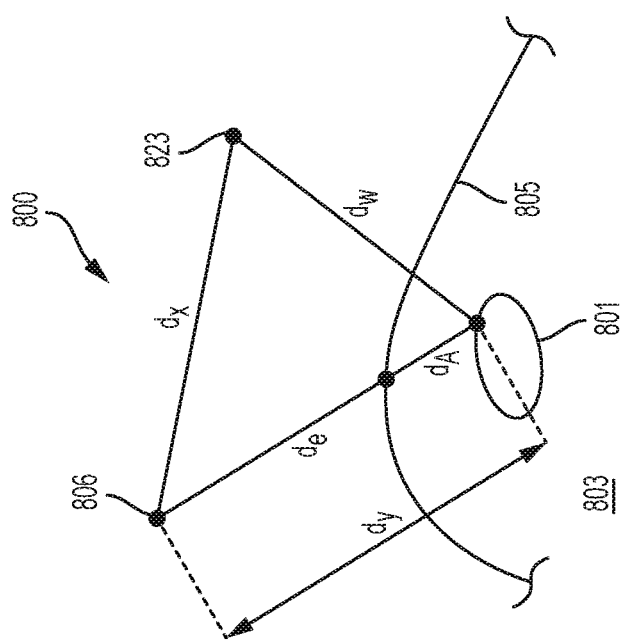
FIG. 29 is a schematic depicting triangularization to determine a depth $d_A$ of a critical structure below the tissue surface, according to at least one aspect of the present disclosure.

Referring now to FIG. 29, in various aspects of the present disclosure, in a surgical visualization system 800, the depth $d_A$ of a critical structure 801 relative to a surface 805 of a tissue 803 can be determined by triangulating from the distance $d_W$ and known positions of an emitter 806 and an optical waveform emitter 823 and detector 823 (and, thus, the known distance $d_x$ therebetween) to determine the distance $d_y$, which is the sum of the distance $d_e$ and the depth $d_A$.

Additionally or alternatively, time-of-flight from the optical waveform emitter 823 can be configured to determine the distance from the optical waveform emitter 823 to the surface 805 of the tissue 803. For example, a first waveform (or range of waveforms) can be utilized to determine the camera-to-critical structure distance $d_W$ and a second waveform (or range of waveforms) can be utilized to determine the distance to the surface 805 of the tissue 803. In such instances, the different waveforms can be utilized to determine the depth of the critical structure 801 below the surface 805 of the tissue 803. Spectral time-of-flight systems are further described herein.

Additionally or alternatively, in certain instances, the distance $d_A$ can be determined from an ultrasound, a registered magnetic resonance imaging (MRI) or computerized tomography (CT) scan. In still other instances, the distance $d_A$ can be determined with spectral imaging because the detection signal received by the imaging device can vary based on the type of material. For example, fat can decrease the detection signal in a first way, or a first amount, and collagen can decrease the detection signal in a different, second way, or a second amount.

Figure 30:
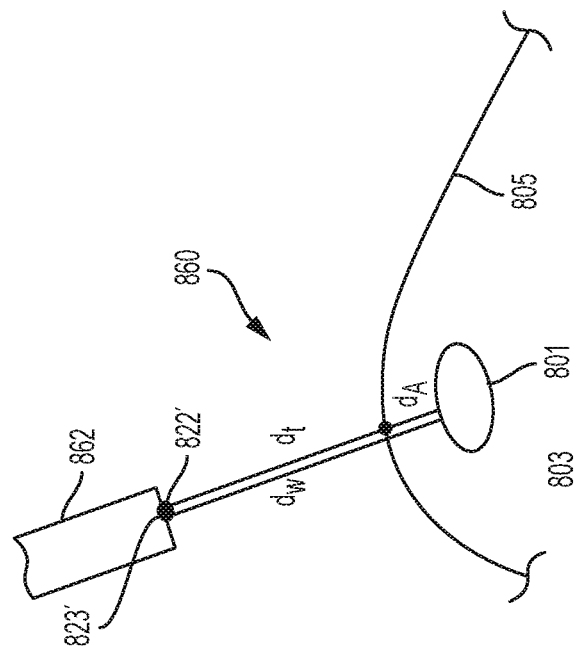
FIG. 30 is a schematic of a surgical visualization system configured to identify a critical structure below a tissue surface, wherein the surgical visualization system includes a pulsed light source for determining a depth $d_A$ of the critical structure below the tissue surface, according to at least one aspect of the present disclosure.

Referring now to a surgical visualization system 860 in FIG. 30, in which a surgical device 862 includes the optical waveform emitter 823' and the waveform sensor 822' that is configured to detect the reflected waveforms. The optical waveform emitter 823' can be configured to emit waveforms for determining the distances $d_t$ and $d_W$ from a common device, such as the surgical device 862, as further described herein. In such instances, the distance $d_A$ from the surface 805 of the tissue 803 to the surface of the critical structure 801 can be determined as follows:

$$d_A = d_W - d_t.$$

As disclosed herein, various information regarding visible tissue, embedded critical structures, and surgical devices can be determined by utilizing a combination approach that incorporates one or more time-of-flight distance sensors, spectral imaging, and/or structured light arrays in combination with an image sensor configured to detect the spectral wavelengths and the structured light arrays. Moreover, an image sensor can be configured to receive visible light and, thus, provide images of the surgical site to an imaging system. Logic or algorithms are employed to discern the information received from the time-of-flight sensors, spectral wavelengths, structured light, and visible light and render three-dimensional images of the surface tissue and underlying anatomical structures. In various instances, the imaging device 520 can include multiple image sensors.

Figure 31:
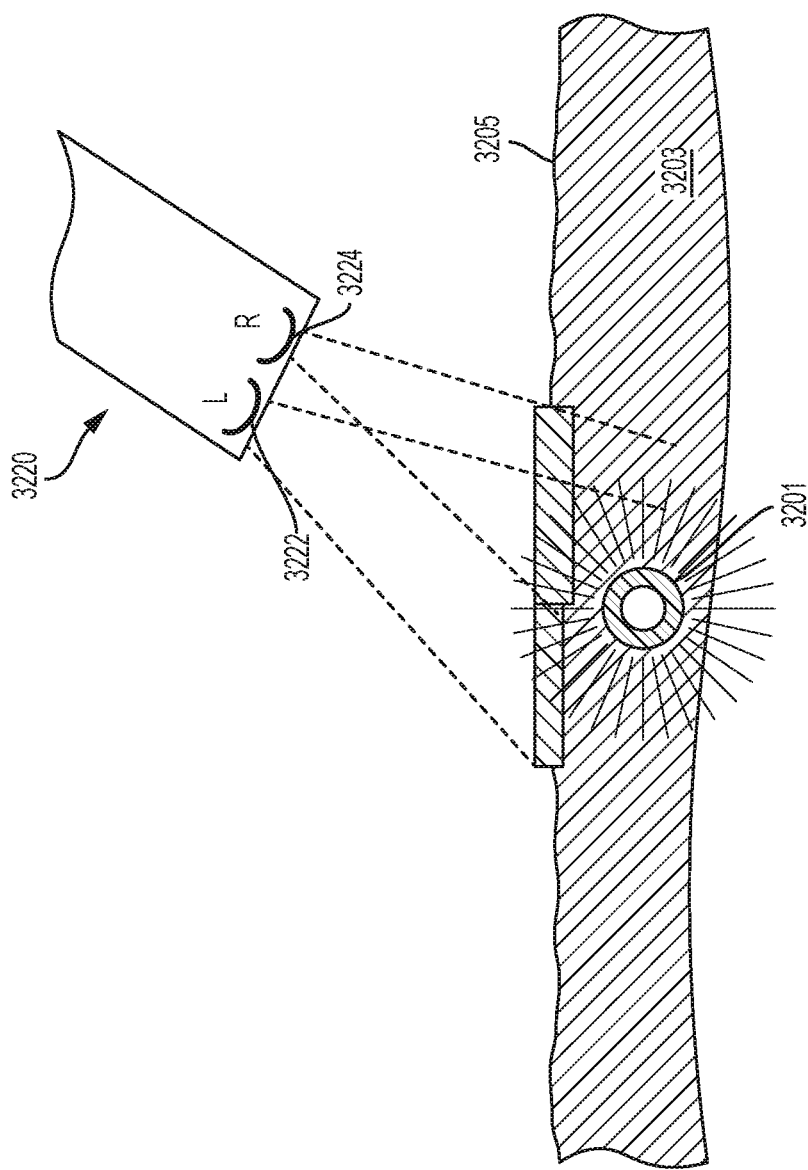
FIG. 31 is a schematic of a surgical visualization system including a three-dimensional camera, wherein the surgical visualization system is configured to identify a critical structure that is embedded within tissue, according to at least one aspect of the present disclosure.

The camera-to-critical structure distance $d_W$ can also be detected in one or more alternative ways. In one aspect, a fluoroscopy visualization technology, such as fluorescent indosciedine green (ICG), for example, can be utilized to illuminate a critical structure 3201, as shown in FIGS. 31-33. A camera 3220 can include two optical waveforms sensors 3222, 3224, which take simultaneous left-side and right-side images of the critical structure 3201 (FIGS. 32A and 32B). In such instances, the camera 3220 can depict a glow of the critical structure 3201 below the surface 3205 of the tissue 3203, and the distance $d_W$ can be determined by the known distance between the sensors 3222 and 3224. In certain instances, distances can be determined more accurately by utilizing more than one camera or by moving a camera between multiple locations. In certain aspects, one camera can be controlled by a first robotic arm and a second camera by another robotic arm. In such a robotic system, one camera can be a follower camera on a follower arm, for example. The follower arm, and camera thereon, can be programmed to track the other camera and to maintain a particular distance and/or lens angle, for example.

Figure 34:
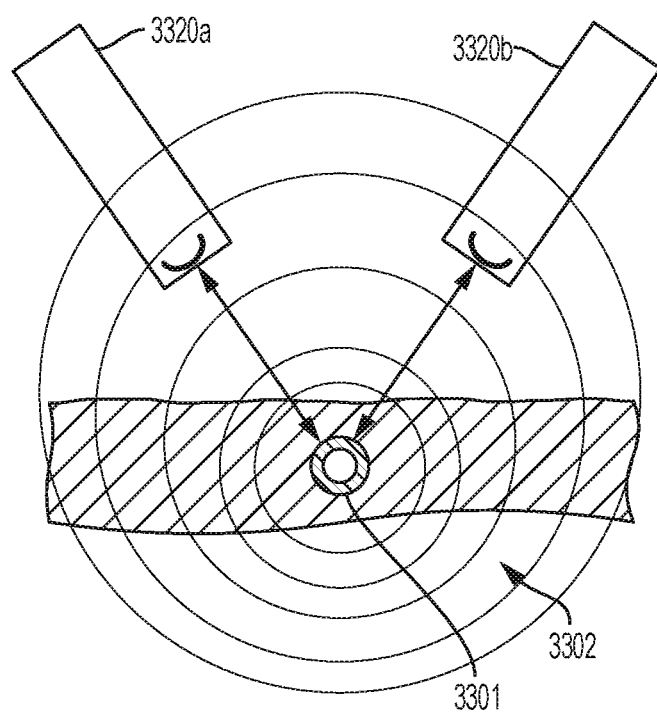
FIG. 34 is a schematic of a surgical visualization system utilizing two cameras to determine the position of an embedded critical structure, according to at least one aspect of the present disclosure.

In still other aspects, the surgical visualization system 500 may employ two separate waveform receivers (i.e. cameras/image sensors) to determine $d_W$. Referring now to FIG. 34, if a critical structure 3301 or the contents thereof (e.g. a vessel or the contents of the vessel) can emit a signal 3302, such as with fluoroscopy, then the actual location can be triangulated from two separate cameras 3320a, 3320b at known locations.

Figure 35B:
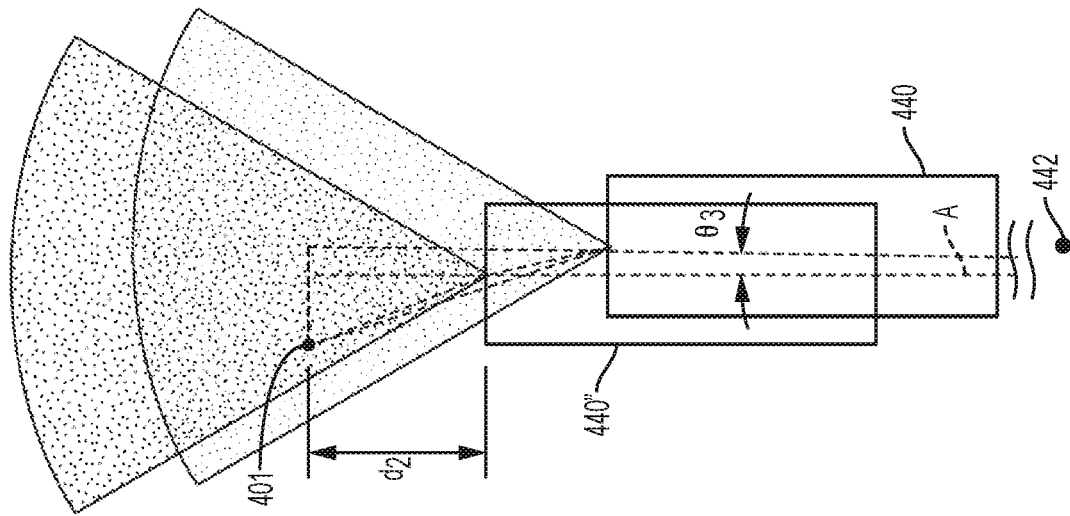
FIG. 35B is a schematic of the surgical visualization system of FIG. 35A, in which the camera is moved axially and rotationally between a plurality of known positions to determine a position of the embedded critical structure, according to at least one aspect of the present disclosure.
Figure 35A:
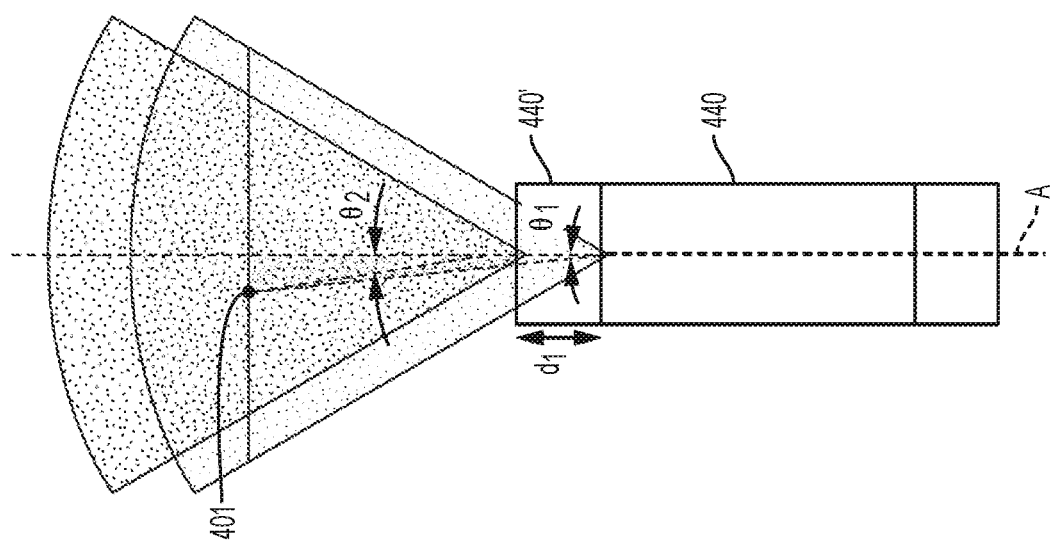
FIG. 35A is a schematic of a surgical visualization system utilizing a camera that is moved axially between a plurality of known positions to determine a position of an embedded critical structure, according to at least one aspect of the present disclosure.

In another aspect, referring now to FIGS. 35A and 35B, a surgical visualization system may employ a dithering or moving camera 440 to determine the distance $d_W$. The camera 440 is robotically-controlled such that the three-dimensional coordinates of the camera 440 at the different positions are known. In various instances, the camera 440 can pivot at a cannula or patient interface. For example, if a critical structure 401 or the contents thereof (e.g. a vessel or the contents of the vessel) can emit a signal, such as with fluoroscopy, for example, then the actual location can be triangulated from the camera 440 moved rapidly between two or more known locations. In FIG. 35A, the camera 440 is moved axially along an axis A. More specifically, the camera 440 translates a distance $d_1$ closer to the critical structure 401 along the axis A to the location indicated as a location 440', such as by moving in and out on a robotic arm.

As the camera 440 moves the distance $d_1$ and the size of view change with respect to the critical structure 401, the distance to the critical structure 401 can be calculated. For example, a 4.28 mm axial translation (the distance $d_1$) can correspond to an angle $\theta_1$ of 6.28 degrees and an angle $\theta_2$ of 8.19 degrees.

Additionally or alternatively, the camera 440 can rotate or sweep along an arc between different positions. Referring now to FIG. 35B, the camera 440 is moved axially along the axis A and is rotated an angle $\theta_3$ about the axis A. A pivot point 442 for rotation of the camera 440 is positioned at the cannula/patient interface. In FIG. 35B, the camera 440 is translated and rotated to a location 440". As the camera 440 moves and the edge of view changes with respect to the critical structure 401, the distance to the critical structure 401 can be calculated. In FIG. 35B, a distance $d_2$ can be 9.01 mm, for example, and the angle $\theta_3$ can be 0.9 degrees, for example.

FIG. 25 is a schematic diagram of the control system 833, which can be utilized with the surgical visualization system 500 and the input control device 1000, for example. The control system 833 includes a control circuit 832 in signal communication with a memory 834. The memory 834 stores instructions executable by the control circuit 832 to determine and/or recognize critical structures (e.g. the critical structures 501a, 501b in FIG. 24), determine and/or compute one or more distances and/or three-dimensional digital representations, and/or to communicate certain information to one or more clinicians, among other things. For example, the memory 834 stores surface mapping logic 836, imaging logic 838, tissue identification logic 840, or distance determining logic 841 or any combinations of the logic 836, 838, 840, and 841. The memory 834 can also include input control device logic for implementing the input controls provided to the input control device 1000, including scaling and/or locking out certain controls in certain circumstances and/or switching between operational modes based on real-time, intraoperative tissue proximity data, for example. The control system 833 also includes an imaging system 842 having one or more cameras 844 (like the imaging device 520 in FIG. 24), one or more displays 846, or one or more controls 848 or any combinations of these elements. The camera 844 can include one or more image sensors 835 to receive signals from various light sources emitting light at various visible and invisible spectra (e.g. visible light, spectral imagers, three-dimensional lens, among others). The display 846 can include one or more screens or monitors for depicting real, virtual, and/or virtually-augmented images and/or information to one or more clinicians.

In various aspects, the heart of the camera 844 is the image sensor 835. Generally, modern image sensors 835 are solid-state electronic devices containing up to millions of discrete photodetector sites called pixels. The image sensor 835 technology falls into one of two categories: Charge-Coupled Device (CCD) and Complementary Metal Oxide Semiconductor (CMOS) imagers and more recently, short-wave infrared (SWIR) is an emerging technology in imaging. Another type of image sensor 835 employs a hybrid CCD/CMOS architecture (sold under the name "sCMOS") and consists of CMOS readout integrated circuits (ROICs) that are bump bonded to a CCD imaging substrate. CCD and CMOS image sensors 835 are sensitive to wavelengths from approximately 350-1050 nm, although the range is usually given from 400-1000 nm. CMOS sensors are, in general, more sensitive to IR wavelengths than CCD sensors. Solid state image sensors 835 are based on the photoelectric effect and, as a result, cannot distinguish between colors. Accordingly, there are two types of color CCD cameras: single chip and three-chip. Single chip color CCD cameras offer a common, low-cost imaging solution and use a mosaic (e.g. Bayer) optical filter to separate incoming light into a series of colors and employ an interpolation algorithm to resolve full color images. Each color is, then, directed to a different set of pixels. Three-chip color CCD cameras provide higher resolution by employing a prism to direct each section of the incident spectrum to a different chip. More accurate color reproduction is possible, as each point in space of the object has separate RGB intensity values, rather than using an algorithm to determine the color. Three-chip cameras offer extremely high resolutions.

The control system 833 also includes a spectral light source 850 and a structured light source 852. In certain instances, a single source can be pulsed to emit wavelengths of light in the spectral light source 850 range and wavelengths of light in the structured light source 852 range. Alternatively, a single light source can be pulsed to provide light in the invisible spectrum (e.g. infrared spectral light) and wavelengths of light on the visible spectrum. The spectral light source 850 can be a hyperspectral light source, a multispectral light source, and/or a selective spectral light source, for example. In various instances, the tissue identification logic 840 can identify critical structure(s) via data from the spectral light source 850 received by the image sensor 835 portion of the camera 844. The surface mapping logic 836 can determine the surface contours of the visible tissue based on reflected structured light. With time-of-flight measurements, the distance determining logic 841 can determine one or more distance(s) to the visible tissue and/or a critical structure. One or more outputs from the surface mapping logic 836, the tissue identification logic 840, and the distance determining logic 841, can be provided to the imaging logic 838, and combined, blended, and/or overlaid to be conveyed to a clinician via the display 846 of the imaging system 842.

Figure 26:
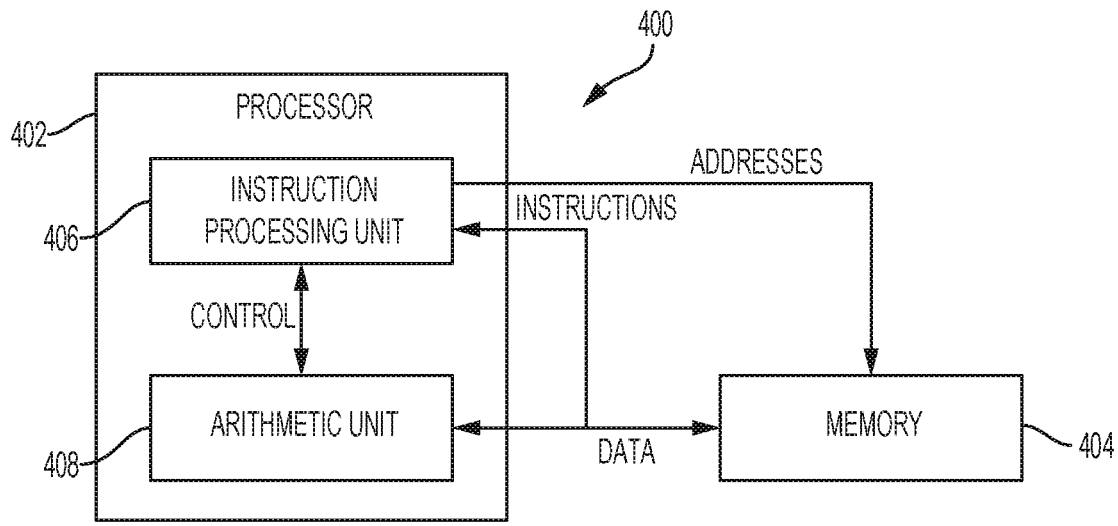
FIG. 26 illustrates a control circuit configured to control aspects of a surgical visualization system, according to at least one aspect of the present disclosure.
Figure 27:
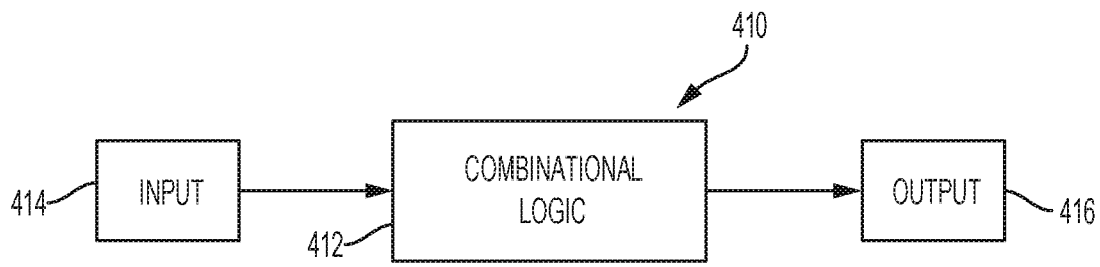
FIG. 27 illustrates a combinational logic circuit configured to control aspects of a surgical visualization system, according to at least one aspect of the present disclosure.
Figure 28:
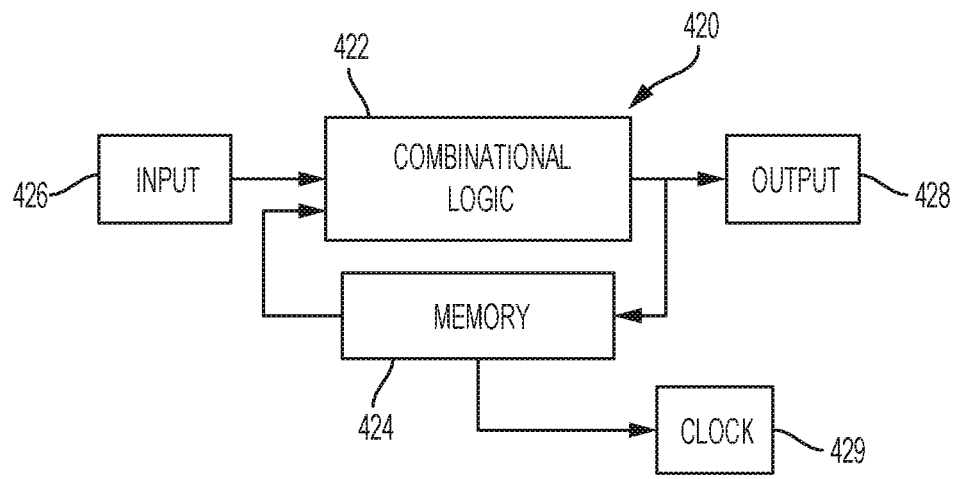
FIG. 28 illustrates a sequential logic circuit configured to control aspects of a surgical visualization system, according to at least one aspect of the present disclosure.

The description now turns briefly to FIGS. 26-28 to describe various aspects of the control circuit 832 for controlling various aspects of the surgical visualization system 500. Turning to FIG. 26, there is illustrated a control circuit 400 configured to control aspects of the surgical visualization system 500, according to at least one aspect of this disclosure. The control circuit 400 can be configured to implement various processes described herein. The control circuit 400 may comprise a microcontroller comprising one or more processors 402 (e.g., microprocessor, microcontroller) coupled to at least one memory circuit 404. The memory circuit 404 stores machine-executable instructions that, when executed by the processor 402, cause the processor 402 to execute machine instructions to implement various processes described herein. The processor 402 may be any one of a number of single-core or multicore processors known in the art. The memory circuit 404 may comprise volatile and non-volatile storage media. The processor 402 may include an instruction processing unit 406 and an arithmetic unit 408. The instruction processing unit may be configured to receive instructions from the memory circuit 404 of this disclosure.

FIG. 27 illustrates a combinational logic circuit 410 configured to control aspects of the surgical visualization system 500, according to at least one aspect of this disclosure. The combinational logic circuit 410 can be configured to implement various processes described herein. The combinational logic circuit 410 may comprise a finite state machine comprising a combinational logic 412 configured to receive data associated with the surgical instrument or tool at an input 414, process the data by the combinational logic 412, and provide an output 416.

FIG. 28 illustrates a sequential logic circuit 420 configured to control aspects of the surgical visualization system 500, according to at least one aspect of this disclosure. The sequential logic circuit 420 or the combinational logic 422 can be configured to implement various processes described herein. The sequential logic circuit 420 may comprise a finite state machine. The sequential logic circuit 420 may comprise a combinational logic 422, at least one memory circuit 424, and a clock 429, for example. The at least one memory circuit 424 can store a current state of the finite state machine. In certain instances, the sequential logic circuit 420 may be synchronous or asynchronous. The combinational logic 422 is configured to receive data associated with a surgical device or system from an input 426, process the data by the combinational logic 422, and provide an output 428. In other aspects, the circuit may comprise a combination of a processor (e.g., processor 402 in FIG. 26) and a finite state machine to implement various processes herein. In other aspects, the finite state machine may comprise a combination of a combinational logic circuit (e.g., combinational logic circuit 410, FIG. 27) and the sequential logic circuit 420.

Figure 36:
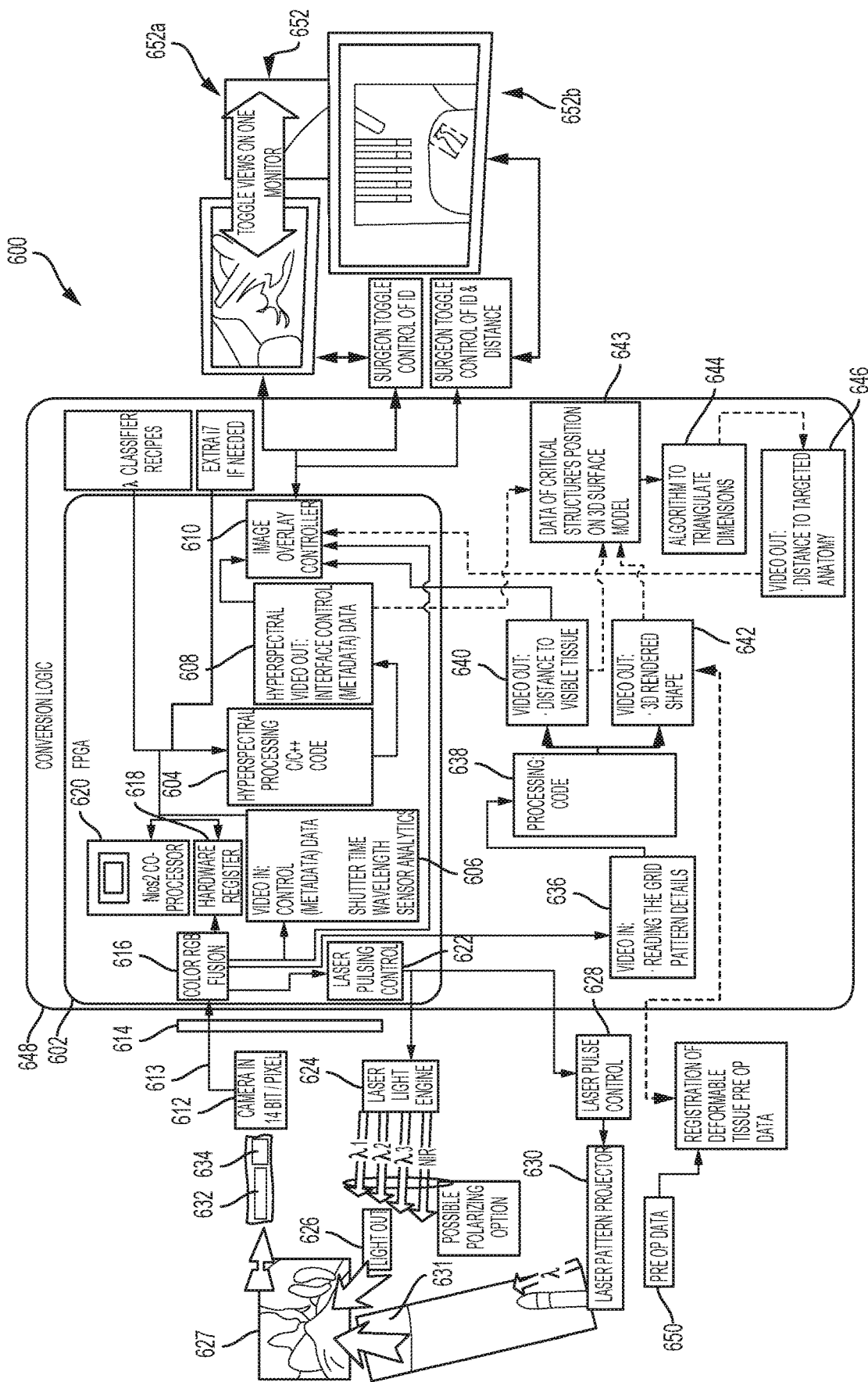
FIG. 36 is a schematic of a control system for a surgical visualization system, according to at least one aspect of the present disclosure.

Referring now to FIG. 36, where a schematic of a control system 600 for a surgical visualization system, such as the surgical visualization system 500, for example, is depicted. The control system 600 is a conversion system that integrates spectral signature tissue identification and structured light tissue positioning to identify critical structures, especially when those structures are obscured by other tissue, such as fat, connective tissue, blood, and/or other organs, for example. Such technology could also be useful for detecting tissue variability, such as differentiating tumors and/or non-healthy tissue from healthy tissue within an organ.

The control system 600 is configured for implementing a hyperspectral imaging and visualization system in which a molecular response is utilized to detect and identify anatomy in a surgical field of view. The control system 600 includes a conversion logic circuit 648 to convert tissue data to surgeon usable information. For example, the variable reflectance based on wavelengths with respect to obscuring material can be utilized to identify the critical structure in the anatomy. Moreover, the control system 600 combines the identified spectral signature and the structural light data in an image. For example, the control system 600 can be employed to create of three-dimensional data set for surgical use in a system with augmentation image overlays. Techniques can be employed both intraoperatively and preoperatively using additional visual information. In various instances, the control system 600 is configured to provide warnings to a clinician when in the proximity of one or more critical structures. Various algorithms can be employed to guide robotic automation and semi-automated approaches based on the surgical procedure and proximity to the critical structure(s).

A projected array of lights is employed to determine tissue shape and motion intraoperatively. Alternatively, flash Lidar may be utilized for surface mapping of the tissue.

The control system 600 is configured to detect the critical structure(s) and provide an image overlay of the critical structure and measure the distance to the surface of the visible tissue and the distance to the embedded/buried critical structure(s). In other instances, the control system 600 can measure the distance to the surface of the visible tissue or detect the critical structure(s) and provide an image overlay of the critical structure.

The control system 600 includes a spectral control circuit 602. The spectral control circuit 602 can be a field programmable gate array (FPGA) or another suitable circuit configuration as described herein in connection with FIGS. 26-28, for example. The spectral control circuit 602 includes a processor 604 to receive video input signals from a video input processor 606. The processor 604 can be configured for hyperspectral processing and can utilize C/C++ code, for example. The video input processor 606 receives video-in of control (metadata) data such as shutter time, wavelength, and sensor analytics, for example. The processor 604 is configured to process the video input signal from the video input processor 606 and provide a video output signal to a video output processor 608, which includes a hyperspectral video-out of interface control (metadata) data, for example. The video output processor 608 provides the video output signal to an image overlay controller 610.

The video input processor 606 is coupled to a camera 612 at the patient side via a patient isolation circuit 614. As previously discussed, the camera 612 includes a solid state image sensor 634. The patient isolation circuit can include a plurality of transformers so that the patient is isolated from other circuits in the system. The camera 612 receives intraoperative images through optics 632 and the image sensor 634. The image sensor 634 can include a CMOS image sensor, for example, or may include any of the image sensor technologies discussed herein in connection with FIG. 25, for example. In one aspect, the camera 612 outputs images in 14 bit/pixel signals. It will be appreciated that higher or lower pixel resolutions may be employed without departing from the scope of the present disclosure. The isolated camera output signal 613 is provided to a color RGB fusion circuit 616, which employs a hardware register 618 and a Nios2 co-processor 620 to process the camera output signal 613. A color RGB fusion output signal is provided to the video input processor 606 and a laser pulsing control circuit 622.

The laser pulsing control circuit 622 controls a laser light engine 624. The laser light engine 624 outputs light in a plurality of wavelengths ($\lambda_1, \lambda_2, \lambda_3 \ldots \lambda_n$) including near infrared (NIR). The laser light engine 624 can operate in a plurality of modes. In one aspect, the laser light engine 624 can operate in two modes, for example. In a first mode, e.g. a normal operating mode, the laser light engine 624 outputs an illuminating signal. In a second mode, e.g. an identification mode, the laser light engine 624 outputs RGBG and NIR light. In various instances, the laser light engine 624 can operate in a polarizing mode.

Light output 626 from the laser light engine 624 illuminates targeted anatomy in an intraoperative surgical site 627. The laser pulsing control circuit 622 also controls a laser pulse controller 628 for a laser pattern projector 630 that projects a laser light pattern 631, such as a grid or pattern of lines and/or dots, at a predetermined wavelength ($\lambda$) on the operative tissue or organ at the surgical site 627. The camera 612 receives the patterned light as well as the reflected light output through the camera optics 632. The image sensor 634 converts the received light into a digital signal.

The color RGB fusion circuit 616 also outputs signals to the image overlay controller 610 and a video input module 636 for reading the laser light pattern 631 projected onto the targeted anatomy at the surgical site 627 by the laser pattern projector 630. A processing module 638 processes the laser light pattern 631 and outputs a first video output signal 640 representative of the distance to the visible tissue at the surgical site 627. The data is provided to the image overlay controller 610. The processing module 638 also outputs a second video signal 642 representative of a three-dimensional rendered shape of the tissue or organ of the targeted anatomy at the surgical site.

The first and second video output signals 640, 642 include data representative of the position of the critical structure on a three-dimensional surface model, which is provided to an integration module 643. In combination with data from the video out processor 608 of the spectral control circuit 602, the integration module 643 can determine the distance $d_A$ (FIG. 24) to a buried critical structure (e.g. via triangularization algorithms 644), and the distance $d_A$ can be provided to the image overlay controller 610 via a video out processor 646. The foregoing conversion logic can encompass the conversion logic circuit 648 intermediate video monitors 652 and the camera 612, the laser light engine 624, and laser pattern projector 630 positioned at the surgical site 627.

Preoperative data 650 from a CT or MRI scan can be employed to register or align certain three-dimensional deformable tissue in various instances. Such preoperative data 650 can be provided to the integration module 643 and ultimately to the image overlay controller 610 so that such information can be overlaid with the views from the camera 612 and provided to the video monitors 652. Registration of preoperative data is further described herein and in U.S. patent application Ser. No. 16/128,195, titled INTEGRATION OF IMAGING DATA, filed Sep. 11, 2018, for example, which is incorporated by reference herein in its entirety.

The video monitors 652 can output the integrated/augmented views from the image overlay controller 610. A clinician can select and/or toggle between different views on one or more monitors. On a first monitor 652a, the clinician can toggle between (A) a view in which a three-dimensional rendering of the visible tissue is depicted and (B) an augmented view in which one or more hidden critical structures are depicted over the three-dimensional rendering of the visible tissue. On a second monitor 652b, the clinician can toggle on distance measurements to one or more hidden critical structures and/or the surface of visible tissue, for example.

The control system 600 and/or various control circuits thereof can be incorporated into various surgical visualization systems disclosed herein.

In various instances, select wavelengths for spectral imaging can be identified and utilized based on the anticipated critical structures and/or obscurants at a surgical site (i.e. "selective spectral" imaging). By utilizing selective spectral imaging, the amount of time required to obtain the spectral image can be minimized such that the information can be obtained in real-time, or near real-time, and utilized intraoperatively. In various instances, the wavelengths can be selected by a clinician or by a control circuit based on input by the clinician. In certain instances, the wavelengths can be selected based on machine learning and/or big data accessible to the control circuit via a cloud, for example.

The foregoing application of spectral imaging to tissue can be utilized intraoperatively to measure the distance between a waveform emitter and a critical structure that is obscured by tissue. In one aspect of the present disclosure, referring now to FIGS. 41 and 42, a time-of-flight sensor system 2104 utilizing waveforms 2124, 2125 is shown. The time-of-flight sensor system 2104 can be incorporated into the surgical visualization system 500 (FIG. 24) in certain instances. The time-of-flight sensor system 2104 includes a waveform emitter 2106 and a waveform receiver 2108 on the same surgical device 2102. The emitted wave 2124 extends to the critical structure 2101 from the emitter 2106 and the received wave 2125 is reflected back to the receiver 2108 from the critical structure 2101. The surgical device 2102 is positioned through a trocar 2110 that extends into a cavity 2107 in a patient.

The waveforms 2124, 2125 are configured to penetrate obscuring tissue 2103. For example, the wavelengths of the waveforms 2124, 2125 can be in the NIR or SWIR spectrum of wavelengths. In one aspect, a spectral signal (e.g. hyperspectral, multispectral, or selective spectral) or a photoacoustic signal can be emitted from the emitter 2106 and can penetrate the tissue 2103 in which the critical structure 2101 is concealed. The emitted waveform 2124 can be reflected by the critical structure 2101. The received waveform 2125 can be delayed due to the distance d between the distal end of the surgical device 2102 and the critical structure 2101. In various instances, the waveforms 2124, 2125 can be selected to target the critical structure 2101 within the tissue 2103 based on the spectral signature of the critical structure 2101, as further described herein. In various instances, the emitter 2106 is configured to provide a binary signal on and off, as shown in FIG. 42, for example, which can be measured by the receiver 2108.

Based on the delay between the emitted wave 2124 and the received wave 2125, the time-of-flight sensor system 2104 is configured to determine the distance d (FIG. 41). A time-of-flight timing diagram 2130 for the emitter 2106 and the receiver 2108 of FIG. 41 is shown in FIG. 42. The delay is a function of the distance d and the distance d is given by:

$$d = \frac{ct}{2} \cdot \frac{q_2}{q_1 + q_2}$$

where:
c=the speed of light;
t=length of pulse;
$q_1$=accumulated charge while light is emitted; and
$q_2$=accumulated charge while light is not being emitted.

As provided herein, the time-of-flight of the waveforms 2124, 2125 corresponds to the distance d in FIG. 41. In various instances, additional emitters/receivers and/or pulsing signals from the emitter 2106 can be configured to emit a non-penetrating signal. The non-penetrating tissue can be configured to determine the distance from the emitter to the surface 2105 of the obscuring tissue 2103. In various instances, the depth of the critical structure 2101 can be determined by:

$$d_A = d_W - d_t.$$

where:
$d_A$=the depth of the critical structure 2101 below the surface 2105 of the obscuring tissue 2103;
$d_W$=the distance from the emitter 2106 to the critical structure 2101 (d in FIG. 41); and
$d_t$=the distance from the emitter 2106 (on the distal end of the surgical device 2102) to the surface 2105 of the obscuring tissue 2103.

In one aspect of the present disclosure, referring now to FIG. 43, a time-of-flight sensor system 2204 utilizing waves 2224a, 2224b, 2224c, 2225a, 2225b, 2225c is shown. The time-of-flight sensor system 2204 can be incorporated into the surgical visualization system 500 (FIG. 24) in certain instances. The time-of-flight sensor system 2204 includes a waveform emitter 2206 and a waveform receiver 2208. The waveform emitter 2206 is positioned on a first surgical device 2202a, and the waveform receiver 2208 is positioned on a second surgical device 2202b. The surgical devices 2202a, 2202b are positioned through their respective trocars 2210a, 2210b, respectively, which extend into a cavity 2207 in a patient. The emitted waves 2224a, 2224b, 2224c extend toward a surgical site from the emitter 2206 and the received waves 2225a, 2225b, 2225c are reflected back to the receiver 2208 from various structures and/or surfaces at the surgical site.

The different emitted waves 2224a, 2224b, 2224c are configured to target different types of material at the surgical site. For example, the wave 2224a targets the obscuring tissue 2203, the wave 2224b targets a first critical structure 2201a (e.g. a vessel), and the wave 2224c targets a second critical structure 2201b (e.g. a cancerous tumor). The wavelengths of the waves 2224a, 2224b, 2224c can be in the visible light, NIR, or SWIR spectrum of wavelengths. For example, visible light can be reflected off a surface 2205 of the tissue 2203 and NIR and/or SWIR waveforms can be configured to penetrate the surface 2205 of the tissue 2203. In various aspects, as described herein, a spectral signal (e.g. hyperspectral, multispectral, or selective spectral) or a photoacoustic signal can be emitted from the emitter 2206. In various instances, the waves 2224b, 2224c can be selected to target the critical structures 2201a, 2201b within the tissue 2203 based on the spectral signature of the critical structures 2201a, 2201b, as further described herein.

The emitted waves 2224a, 2224b, 2224c can be reflected off the targeted material (i.e. the surface 2205, the first critical structure 2201a, and the second structure 2201b, respectively). The received waveforms 2225a, 2225b, 2225c can be delayed due to the distances $d_{1a}, d_{2a}, d_{3a}, d_{1b}, d_{2b}, d_{3b}$ indicated in FIG. 43.

In the time-of-flight sensor system 2204, in which the emitter 2206 and the receiver 2208 are independently positionable (e.g., on separate surgical devices 2202a, 2202b and/or controlled by separate robotic arms), the various distances $d_{1a}, d_{2a}, d_{3a}, d_{1b}, d_{2b}, d_{3b}$ can be calculated from the known position of the emitter 2206 and the receiver 2208. For example, the positions can be known when the surgical devices 2202a, 2202b are robotically-controlled. Knowledge of the positions of the emitter 2206 and the receiver 2208, as well as the time of the photon stream to target a certain tissue and the information received by the receiver 2208 of that particular response can allow a determination of the distances $d_{1a}, d_{2a}, d_{3a}, d_{1b}, d_{2b}, d_{3b}$. In one aspect, the distance to the obscured critical structures 2201a, 2201b can be triangulated using penetrating wavelengths. Because the speed of light is constant for any wavelength of visible or invisible light, the time-of-flight sensor system 2204 can determine the various distances.

Referring still to FIG. 43, in various instances, in the view provided to the clinician, the receiver 2208 can be rotated such that the center of mass of the target structure in the resulting images remains constant, i.e., in a plane perpendicular to the axis of a select target structures 2203, 2201a, or 2201b. Such an orientation can quickly communicate one or more relevant distances and/or perspectives with respect to the critical structure. For example, as shown in FIG. 43, the surgical site is displayed from a viewpoint in which the first critical structure 2201a is perpendicular to the viewing plane (i.e. the vessel is oriented in/out of the page). In various instances, such an orientation can be the default setting; however, the view can be rotated or otherwise adjusted by a clinician. In certain instances, the clinician can toggle between different surfaces and/or target structures that define the viewpoint of the surgical site provided by the imaging system.

In various instances, the receiver 2208 can be mounted on a trocar or cannula, such as the trocar 2210b, for example, through which the second surgical device 2202b is positioned. In other instances, the receiver 2208 can be mounted on a separate robotic arm for which the three-dimensional position is known. In various instances, the receiver 2208 can be mounted on a movable arm that is separate from the robot that controls the first surgical device 2202a or can be mounted to an operating room (OR) table that is intraoperatively registerable to the robot coordinate plane. In such instances, the position of the emitter 2206 and the receiver 2208 can be registerable to the same coordinate plane such that the distances can be triangulated from outputs from the time-of-flight sensor system 2204.

Combining time-of-flight sensor systems and near-infrared spectroscopy (NIRS), termed TOF-NIRS, which is capable of measuring the time-resolved profiles of NIR light with nanosecond resolution can be found in the article titled TIME-OF-FLIGHT NEAR-INFRARED SPECTROSCOPY FOR NONDESTRUCTIVE MEASUREMENT OF INTERNAL QUALITY IN GRAPEFRUIT, in the Journal of the American Society for Horticultural Science, May 2013 vol. 138 no. 3 225-228, which is incorporated by reference herein in its entirety, and is accessible at journal.ashspublications.org/content/138/3/225.full.

In various instances, time-of-flight spectral waveforms are configured to determine the depth of the critical structure and/or the proximity of a surgical device to the critical structure. Moreover, the various surgical visualization systems disclosed herein include surface mapping logic that is configured to create three-dimensional rendering of the surface of the visible tissue. In such instances, even when the visible tissue obstructs a critical structure, the clinician can be aware of the proximity (or lack thereof) of a surgical device to the critical structure. In one instance, the topography of the surgical site is provided on a monitor by the surface mapping logic. If the critical structure is close to the surface of the tissue, spectral imaging can convey the position of the critical structure to the clinician. For example, spectral imaging may detect structures within 5 or 10 mm of the surface. In other instances, spectral imaging may detect structures 10 or 20 mm below the surface of the tissue. Based on the known limits of the spectral imaging system, the system is configured to convey that a critical structure is out-of-range if it is simply not detected by the spectral imaging system. Therefore, the clinician can continue to move the surgical device and/or manipulate the tissue. When the critical structure moves into range of the spectral imaging system, the system can identify the structure and, thus, communicate that the structure is within range. In such instances, an alert can be provided when a structure is initially identified and/or moved further within a predefined proximity zone. In such instances, even nonidentification of a critical structure by a spectral imaging system with known bounds/ranges can provide proximity information (i.e. the lack of proximity) to the clinician.

Various surgical visualization systems disclosed herein can be configured to identify intraoperatively the presence of and/or proximity to critical structure(s) and to alert a clinician prior to damaging the critical structure(s) by inadvertent dissection and/or transection. In various aspects, the surgical visualization systems are configured to identify one or more of the following critical structures: ureters, bowel, rectum, nerves (including the phrenic nerve, recurrent laryngeal nerve [RLN], promontory facial nerve, vagus nerve, and branches thereof), vessels (including the pulmonary and lobar arteries and veins, inferior mesenteric artery [IMA]

and branches thereof, superior rectal artery, sigmoidal arteries, and left colic artery), superior mesenteric artery (SMA) and branches thereof (including middle colic artery, right colic artery, ilecolic artery), hepatic artery and branches thereof, portal vein and branches thereof, splenic artery/vein and branches thereof, external and internal (hypogastric) ileac vessels, short gastric arteries, uterine arteries, middle sacral vessels, and lymph nodes, for example. Moreover, the surgical visualization systems are configured to indicate proximity of surgical device(s) to the critical structure(s) and/or warn the clinician when surgical device(s) are getting close to the critical structure(s).

Various aspects of the present disclosure provide intraoperative critical structure identification (e.g., identification of ureters, nerves, and/or vessels) and instrument proximity monitoring. For example, various surgical visualization systems disclosed herein can include spectral imaging and surgical instrument tracking, which enable the visualization of critical structures below the surface of the tissue, such as 1.0-1.5 cm below the surface of the tissue, for example. In other instances, the surgical visualization system can identify structures less than 1.0 cm or more the 1.5 cm below the surface of the tissue. For example, even a surgical visualization system that can identify structures only within 0.2 mm of the surface, for example, can be valuable if the structure cannot otherwise be seen due to the depth. In various aspects, the surgical visualization system can augment the clinician's view with a virtual depiction of the critical structure as a visible white-light image overlay on the surface of visible tissue, for example. The surgical visualization system can provide real-time, three-dimensional spatial tracking of the distal tip of surgical instruments and can provide a proximity alert when the distal tip of a surgical instrument moves within a certain range of the critical structure, such as within 1.0 cm of the critical structure, for example.

Various surgical visualization systems disclosed herein can identify when dissection is too close to a critical structure. Dissection may be "too close" to a critical structure based on the temperature (i.e. too hot within a proximity of the critical structure that may risk damaging/heating/melting the critical structure) and/or based on tension (i.e. too much tension within a proximity of the critical structure that may risk damaging/tearing/pulling the critical structure). Such a surgical visualization system can facilitate dissection around vessels when skeletonizing the vessels prior to ligation, for example. In various instances, a thermal imaging camera can be utilized to read the heat at the surgical site and provide a warning to the clinician that is based on the detected heat and the distance from a tool to the structure. For example, if the temperature of the tool is over a predefined threshold (such as 120 degrees F., for example), an alert can be provided to the clinician at a first distance (such as 10 mm, for example), and if the temperature of the tool is less than or equal to the predefined threshold, the alert can be provided to the clinician at a second distance (such as 5 mm, for example). The predefined thresholds and/or warning distances can be default settings and/or programmable by the clinician. Additionally or alternatively, a proximity alert can be linked to thermal measurements made by the tool itself, such as a thermocouple that measures the heat in a distal jaw of a monopolar or bipolar dissector or vessel sealer, for example.

Various surgical visualization systems disclosed herein can provide adequate sensitivity with respect to a critical structure and specificity to enable a clinician to proceed with confidence in a quick but safe dissection based on the standard of care and/or device safety data. The system can function intraoperatively and in real-time during a surgical procedure with minimal ionizing radiation risk to a patient or a clinician and, in various instances, no risk of ionizing radiation risk to the patient or the clinician. Conversely, in a fluoroscopy procedure, the patient and clinician(s) may be exposed to ionizing radiation via an X-ray beam, for example, that is utilized to view the anatomical structures in real-time.

Various surgical visualization system disclosed herein can be configured to detect and identify one or more desired types of critical structures in a forward path of a surgical device, such as when the path of the surgical device is robotically controlled, for example. Additionally or alternatively, the surgical visualization system can be configured to detect and identify one or more types of critical structures in a surrounding area of the surgical device and/or in multiple planes/dimensions, for example.

Various surgical visualization systems disclosed herein can be easy to operate and/or interpret. Moreover, various surgical visualization systems can incorporate an "override" feature that allows the clinician to override a default setting and/or operation. For example, a clinician can selectively turn off alerts from the surgical visualization system and/or get closer to a critical structure than suggested by the surgical visualization system such as when the risk to the critical structure is less than risk of avoiding the area (e.g. when removing cancer around a critical structure the risk of leaving the cancerous tissue can be greater than the risk of damage to the critical structure).

Various surgical visualization systems disclosed herein can be incorporated into a surgical system and/or used during a surgical procedure with limited impact to the workflow. In other words, implementation of the surgical visualization system may not change the way the surgical procedure is implemented. Moreover, the surgical visualization system can be economical in comparison to the costs of an inadvertent transection. Data indicates the reduction in inadvertent damage to a critical structure can drive incremental reimbursement.

Various surgical visualization systems disclosed herein can operate in real-time, or near real-time, and far enough in advance to enable a clinician to anticipate critical structure(s). For example, a surgical visualization system can provide enough time to "slow down, evaluate, and avoid" in order to maximize efficiency of the surgical procedure.

Various surgical visualization systems disclosed herein may not require a contrast agent, or dye, that is injected into tissue. For example, spectral imaging is configured to visualize hidden structures intraoperatively without the use of a contrast agent or dye. In other instances, the contrast agent can be easier to inject into the proper layer(s) of tissue than other visualization systems. The time between injection of the contrast agent and visualization of the critical structure can be less than two hours, for example.

Various surgical visualization systems disclosed herein can be linked with clinical data and/or device data. For example, data can provide boundaries for how close energy-enabled surgical devices (or other potentially damaging devices) should be from tissue that the surgeon does not want to damage. Any data modules that interface with the surgical visualization systems disclosed herein can be provided integrally or separately from a robot to enable use with stand-alone surgical devices in open or laparoscopic procedures, for example. The surgical visualization systems can be compatible with robotic surgical systems in various instances. For example, the visualization images/information can be displayed in a robotic console.

Various surgical visualization systems disclosed herein can provide enhanced visualization data and additional information to the surgeon(s) and/or the control unit for a robotic system and/or controller therefor to improve, enhance, and/or inform the input control device and/or controls for the robotic system.

Additional Control Systems

Certain surgeons may be accustomed to using handheld surgical instrument in which a displacement of the handle portion of the surgical instrument effects a corresponding displacement of the end effector portion of the surgical instrument. For example, advancing the handle of a surgical instrument one inch can cause the end effector of the surgical instrument to be advanced a corresponding one inch. Such one-to-one correlations between inputs and outputs can be preferred by certain surgeons utilizing robotic applications as well. For example, when moving a robotic surgical end effector around tissue, one-to-one correlations between input motions and output motions can provide an intuitive control motion. Though one-to-one correlations can be desirable in certain instances, without the assistance of a clutching mechanism, such input motions may not be feasible or practical when displacing a surgical tool across large distances. Moreover, one-to-one correlations may not be necessary or desired in certain instances; however, a surgeon can prefer a displacement input motion (translating and/or rotating) when controlling a robotic surgical tool in certain instances, such as during a precision motion mode.

A clutchless input control device can allow limited translation of a portion thereof during a precision motion mode and can rely on force sensing technology, such as the space joint 1006 and the sensor arrangement 1048 (FIGS. 8 and 9) during a gross motion mode. Tissue proximity data can toggle the input control device between the precision motion mode and the gross motion mode. In such instances, the surgeon can utilize force sensors to drive a surgical end effector large distances toward tissue and, upon reaching a predefined proximity to the tissue, can utilize the limited translation of the portion of the clutchless input control device to provide displacement input motions to control the robotic surgical tool.

Referring now to FIGS. 44-49, an input control device 4000 is shown. The input control device 4000 is a clutchless input control device, as further described herein. The input control device 4000 can be utilized at a surgeon's console or workspace for a robotic surgical system. For example, the input control device 4000 can be incorporated into a surgical system, such as the surgical system 110 (FIG. 1) or the surgical system 150 (FIG. 3), for example, to provide control signals to a surgical robot and/or surgical tool coupled thereto. The input control device 4000 includes manual input controls for moving the robotic arm and/or the surgical tool in three-dimensional space. For example, the surgical tool controlled by the input control device 4000 can be configured to move in three-dimensional space and rotate or articulate about multiple axes (e.g. roll about a longitudinal tool axis and articulate about one or more articulation axes).

The input control device 4000 includes a multi-dimensional space joint 4006 having a central portion 4002 supported on a base 4004, similar to the multi-dimensional space joint 1006, the central portion 1002, and the base 1004 of the input control device 1000 (FIGS. 6-11) in many respects. For example, the base 4004 is structured to rest on a surface, such as a desk or work surface at a surgeon's console or workspace and can remain in a fixed, stationary position relative to an underlying surface upon application of the input control motions to the input control device 4000. The space joint 4006 is configured to receive multi-dimensional inputs corresponding to control motions for the surgical tool in multi-dimensional space. A power cord 4032 extends from the base 4004. The input control device 4000 also include a multi-axis force and/or torque sensor arrangement 4048 (FIG. 46), similar to the sensor arrangement 1048 (FIGS. 8 and 9) in many respects. For example, the sensor arrangement 4048 is configured to detect forces and moments at the space joint 4006, such as forces applied to the central portion 4002. Multi-dimensional space joints and sensor arrangements therefor are further described herein.

The central portion 4002 is flexibly supported relative to the base 4004. In such instances, the central portion 4002 can be configured to move or float within a small predefined zone upon receipt of force control inputs thereto. For example, the central portion 4002 can be a floating shaft that is supported on the base 4004 by one or more elastomeric members such as springs, for example. The central portion 4002 can be configured to move or float within a predefined three-dimensional volume. For example, elastomeric couplings can permit movement of the central portion 4002 relative to the base 4004; however, restraining plates, pins, and/or other structures can be configured to limit the range of motion of the central portion 4002 relative to the base 4004. In one aspect, movement of the central portion 4002 from a central or "home" position relative to the base 4004 can be permitted within a range of about 1.0 mm to about 5.0 mm in any direction (up, down, left, right, backwards and forwards). In other instances, movement of the central portion 4002 relative to the base 4004 can be restrained to less than 1.0 mm or more than 5.0 mm. In certain instances, the central portion 4002 can move about 2.0 mm in all directions relative to the base 4004 and, in still other instances, the central portion 4002 can remain stationary or fixed relative to the base 4004.

In various instances, the central portion 4002 of the space joint 4006 can be spring-biased toward the central or home position, in which the central portion 4002 is aligned with the Z axis, a vertical axis through the central portion 4002 and the space joint 4006. Driving (e.g. pushing and/or pulling) the central portion 4002 away from the Z axis in any direction can be configured to "drive" an end effector of an associated surgical tool in the corresponding direction. When the external driving force is removed, the central portion 4002 can be configured to return to the central or home position and motion of the end effector can be halted. Controlling the robotic surgical tool by forces applied to the sensor arrangement 4048 at the space joint 4006 can be permitted during portions of a surgical procedure, such as during a gross motion mode, as further described herein.

In various instances, the space joint 4006 and the central portion 4002 coupled thereto define a six degree-of-freedom input control. Referring again to the end effector 1052 of the surgical tool 1050 in FIG. 12, the forces on the central portion 4002 of the input control device 4000 in the X direction correspond to displacement of the end effector 1052 along the $X_t$ axis thereof (e.g. longitudinally), forces on the central portion 4002 in the Y direction correspond to displacement of the end effector 1052 along the $Y_t$ axis thereof (e.g. laterally), and forces on the central portion 4002 in the Z direction correspond to displacement of the end effector 1052 along the $Z_t$ axis (e.g. vertically/up and down). Additionally, forces on the central portion 4002 about the X axis (the moment forces R) result in rotation of the end effector 1052 about the $X_t$ axis (e.g. a rolling motion about a longitudinal axis in the direction $R_t$), forces on the central portion 4002 about the Y axis (the moments forces P) result in articulation of the end effector 1052 about the $Y_t$ axis (e.g. a pitching motion in the direction $P_t$), and forces on the central portion 4002 about the Z axis (the moment forces T) result in articulation of the end effector 1052 about the $Z_t$ axis of the end effector (e.g. a yawing or twisting motion in the direction $T_t$). In such instances, the input control device 4000 includes a six-degree of freedom joystick, for example, which is configured to receive and detect six degree-of-freedom—forces along the X, Y, and Z axes and moments about the X, Y, and Z axes. The forces can correspond to translational input and the moments can correspond to rotational inputs for the end effector 1052 of the associated surgical tool 1050. Six degree-of-freedom input devices are further described herein.

Referring again to the input control device 4000 in FIGS. 44-49, a forearm support 4008 is movably coupled to the base 4004. For example, a mechanical joint 4042 incorporated into the central portion 4002 can hold or support the forearm support 4008 such that the forearm support 4008 is movable at the mechanical joint 4042 relative to the base 4004. Referring primarily now to FIG. 47, the forearm support 4008 is shown in a first configuration (solid lines) and in a second configuration (dashed lines). The base 4004 of the input control device 4000 remains stationary as an upper portion (e.g. a collective unit 4011 described herein) of the input control device 4000 is displaced along a longitudinal shaft axis S, which extends parallel to the longitudinal X axis, between the first configuration and the second configuration. In certain instances, the mechanical joint 4042 can permit movement of the forearm support 4008 relative to the base 4004 in multiple directions. For example, the forearm support 4008 can be moveable relative to the base 4004 along one, two or three different axes.

The forearm support 4008 can be movable within a range of motion defined by a travel zone 4050 (FIG. 47) surrounding a forearm home position. For example, the travel zone 4050 can define a one-dimensional path from the forearm home position, wherein the one-dimensional path extends along a longitudinal axis between 2.0 cm and 6.0 cm from the forearm home position. Referring again to FIG. 47, in the first configuration (indicated as input control device 4000 in solid lines), the input control device 4000 has been moved proximally along the longitudinal shaft axis S to the proximal end or limit of the travel zone 4050 and, in the second configuration (indicated as input control device 4000' in dashed lines), the input control device 4000 has been moved distally along the longitudinal shaft axis S to the distal end or limit of the travel zone 4050. In various instances, the travel zone 4050 can define a two-dimensional space extending between 2.0 cm and 6.0 cm in two dimensions from the forearm home position. In still other instances, the travel zone 4050 can define a three-dimensional space extending between 2.0 cm and 6.0 cm in three dimensions from the forearm home position. The type and/or arrangements of joints at the mechanical joint 4042 can determine the degrees of freedom of the forearm support 4008 relative to the base 4004. The mechanical joint 4042, which is supported and/or built on the central portion 4002 of the space joint 4006 can include elastically-coupled components, sliders, journaled shafts, hinges, and/or rotary bearings, for example.

The degrees of freedom and the dimensions of the travel zone 4050 can be selected to provide the surgeon with first-person perspective control of the end effector (i.e. from the surgeon's perspective, being "positioned" at the jaws of the remotely-positioned end effector at the surgical site). In various instances, motion of a handpiece 4020 on the input control device 4000 can correspond to one-to-one corresponding motion of the surgical end effector. For example, moving the handpiece 4020 distally along the shaft axis S a distance of 1.0 cm can correspond to a distal displacement of the end effector a distance of 1.0 cm along the longitudinal shaft axis S of the surgical tool. Similarly, rotating the handpiece 4020 at a wrist or joint 4010 counterclockwise five degrees can correspond to a rotational displacement of the end effector by five degrees in the counterclockwise direction. In various instances, the input control motions to the control input device 4000 can be scaled, as further described herein and in various co-owned applications that have been incorporated by reference herein.

The input control device 4000 also includes a shaft 4012 extending distally from the forearm support 4008 and the handpiece 4020 extending distally from the shaft 4012. The forearm support 4008, the shaft 4012, and the handpiece 4020 form a collective unit 4011, which is movable together as the forearm support 4008 is moved relative to the base 4004 within the travel zone 4050 defined by the mechanical joint 4042. A displacement sensor is configured to detect movement of the collective unit 4011. The handpiece 4020 defines an end effector actuator having at least one jaw, as further described herein. The shaft 4012 includes a linear portion extending along the shaft axis S that is parallel to the axis X in the configuration shown in FIG. 6. The shaft 4012 also includes a contoured "gooseneck" portion 4018 that curves away from the shaft axis S to position the handpiece 4020 in a comfortable position and orientation for the surgeon relative to the forearm support 4008. For example, the contoured portion 4018 defines a curvature of about 90 degrees. In other instances, the curvature can be less than 90 degrees or more than 90 degrees and can be selected based on the surgeon's preference(s) and/or anthropometrics, for example.

The shaft 4012 supports the wrist 4010 intermediate the linear portion and the contoured portion 4018. For example, the wrist 4010 can be positioned at the distal end of the linear portion, such that the contoured portion 4018 is configured to rotate relative to the linear portion upon application of manual control motions thereto. The wrist 4010 is longitudinally offset from the space joint 4006. The wrist 4010 defines a mechanical joint to facilitate rotary motion. The wrist 4010 can include elastically-coupled components, sliders, journaled shafts, hinges, and/or rotary bearings, for example. The wrist 4010 can also include a rotary sensor (e.g. the sensor 1049 in FIG. 25), which can be a rotary force/torque sensor and/or transducer, rotary strain gauge, strain gauge on a spring, rotary encoder, and/or an optical sensor to detect rotary displacement at the joint, for example.

The wrist 4010 can define input control motions for at least one degree of freedom. For example, the wrist 4010 can define the input control motions for the rolling motion of a robotic end effector controlled by the input control device 4000. Rotation of the wrist 4010 by the surgeon to roll an end effector provides control of the rolling motion at the surgeon's fingertips and corresponds to a first-person perspective control of the end effector (i.e. from the surgeon's perspective, being "positioned" at the jaws of the remotely-positioned end effector at the surgical site). As further described herein, such placement and perspective can be utilized to supply precision control motions to the input control device 4000 during portions of a surgical procedure (e.g. a precision motion mode).

In certain instances, the input control device 4000 can include additional wristed joints. For example, the shaft 4012 can include one or more additional rotary joints along the length thereof, such as at a juncture or junction 4014 (FIG. 44) along a linear portion of the shaft 4012 and/or at a juncture or junction 4016 at the distal end of the contoured portion 4018 of the shaft 4012. For example, a mechanical joint at the junction 4016 can permit articulation of the handpiece 4020 relative to the shaft 4012 about at least one axis. In various instances, the handpiece 4020 can be articulated about at least two axes (e.g. the axis $Z_1$ that is parallel to the axis Z in FIG. 45 and the axis $Y_1$ that is parallel to the axis Y in FIG. 45). The additional joints can provide additional degrees of freedom for the input control device 4000, which can detected by a sensor arrangement and converted to rotary input control motions for the end effector, such as a yawing or pitching articulation of the end effector. Such an arrangement requires one or more additional sensor arrangements to detect the rotary input at the junction 4016, for example.

As further described herein, the space joint 4006 can define the input control motions for multiple degrees of freedom. For example, the space joint 4006 can define the input control motions for translation of the surgical tool in three-dimensional space and rotation of the surgical tool about at least one axis. Rolling motions can be controlled by inputs to the space joint 4006 and/or the wrist 4010. Whether a rolling control motion is provided by the wrist 4010 or the space joint 4006 of the input control device 4000 can depend on the actions of the surgeon and/or the operational mode of the input control device 4000, as further described herein. Articulation motions can be controlled by inputs to the space joint 4006 and/or the junction 4016. Whether an articulation control motion is provided by the junction 4016 or the space joint 4006 of the input control device 4000 can depend on the actions of the surgeon and/or the operational mode of the input control device 4000, as further described herein.

The handpiece 4020 includes an end effector actuator having opposing fingers 4022 extending distally from the shaft 4012. The opposing fingers 4022 can be similar to the fingers 1022 (FIGS. 6-11) in many respects. Applying an actuation force to the opposing fingers 4022 comprises an input control motion for a surgical tool. For example, referring again to FIG. 12, applying a pinching force to the opposing fingers 4022 can close and/or clamp the jaws 1054 of the end effector 1052 (see arrows C in FIG. 12). In various instances, applying a spreading force can open and/or release the jaws 1054 of the end effector 1052, such as for a spread dissection task, for example. The fingers 4022 also includes loops 4030, which are similar to the loops 1030 (FIGS. 6-11) in many respects. The opposing fingers 4022 can be displaced symmetrically or asymmetrically relative to the longitudinal shaft axis S during an actuation. The displacement of the opposing fingers 4022 can depend on the force applied by the surgeon, for example, and a desired surgical function. The input control device 4000 includes at least one additional actuator, such as the actuation buttons 4026, 4028, for example, which can provide additional controls at the surgeon's fingertips, e.g. the surgeon's index finger I, similar to the actuation buttons 1026, 1028 (FIGS. 6-11) in many respects. The reader will appreciate that the actuation buttons 4026, 4028 can have different geometries and/or structures, and can include a trigger, a button, a switch, a lever, a toggle, and combinations thereof.

Referring primarily to FIGS. 48 and 49, during use, a surgeon can position a portion of his or her arm on the forearm support 4008 and can provide forces to the space joint 4006 via inputs at the forearm support 4008. The surgeon's forearm can be positioned on the lower portion of the forearm support 4008 and a cuff or sleeve of the forearm support 4008 can at least partially surround the surgeon's arm in certain instances. For example, the forearm support 4008 forms a partial loop having a curvature of more than 180 degrees. In certain instances, the curvature can define an arc of approximately 270 degrees, for example. In other instances, the cuff or sleeve can form an enclosed loop through which the surgeon can position his or her arm. Alternative geometries for the forearm support are envisioned. The surgeon's thumb T is positioned through one of the loops 4030 and the surgeon's middle finger M is positioned through the other loop 4030. In such instances, the surgeon can pinch and/or spread his thumb T and middle finger M to actuate the opposing fingers 4022. The distally-extending fingers 4022 (for actuation of the jaws) and the actuation buttons 4026, 4028 (for actuation of a surgical function at the jaws) are distal to the space joint 4006 and wrist 4010. Such a configuration mirrors the configuration of a surgical tool in which the end effector is distal to the more-proximal articulation joint(s) and/or rotatable shaft and, thus, provides an intuitive arrangement that facilitates a surgeon's training and adoption of the input control device 4000.

In various instances, the input controls for the input control device 4000 are segmented between first control motions and second control motions, similar in many aspects to the operational modes described with respect to the input control device 1000 (FIGS. 6-11). Control logic for the input control device 4000 can be utilized in the control circuit 832 (FIG. 25), the control circuit 1400 (FIG. 11C), the combinational logical circuit 1410 (FIG. 11D), and/or the sequential logic circuit 1420 (FIG. 11E), for example, where an input is provided from inputs to the input control device 4000 and/or a surgical visualization system or distance determining subsystem thereof, as further described herein. Inputs from the input control device 4000 include feedback from the various sensors thereof and related to control inputs at the space joint 4006, the wrist 4010, and/or the handpiece 4020, for example.

Referring now to FIG. 50, control logic 4068 for the input control device 4000 can activate or maintain a gross motion mode at a block 4082 if the distance ($d_t$) determined by a distance determining subsystem is greater than or equal to a threshold distance ($D_{critical}$) and can deactivate the gross motion mode at a block 4076 if the distance ($d_t$) is less than the threshold distance ($D_{critical}$). More specifically, when a force is initially applied to the forearm support 4008 to move the forearm support 4008 to the end of its constrained travel zone (e.g. a boundary of the travel zone 4050 in FIG. 47) at a block 4070, the robotic surgical tool is controlled to move at a surgical site relative to relevant tissue at a block 4072. In various instances, the force required to input control motions via the sensor arrangement 4048 (FIG. 46) can be greater than the force required to move the forearm support 4008 to the end of its travel zone. In other words, the surgeon can move the forearm support 4008 to the ends of its travel zone before effecting control motions with the sensor arrangement 4048.

As the robotic surgical tool is moved relative to tissue, the control logic checks proximity data provided by a tissue proximity detection system to determine if the distance ($d_t$) is greater than or equal to a threshold distance ($D_{critical}$) at a block 4074. The control logic 4068 can periodically and/or continuously compare the distance ($d_t$) to the threshold distance ($D_{critical}$) during the surgical procedure (e.g. intra-operatively and/or in real-time). The threshold distance ($D_{critical}$) can be set by the surgeon in certain instances. Moreover, the surgeon may selectively override the default rules and conditions of the control logic 4068, such as the rules related to the comparison at a block 4074 and/or adjustments to the threshold distance ($D_{critical}$), for example.

If the distance ($d_t$) is greater than or equal to the threshold distance ($D_{critical}$), the gross motion mode can be activated at a block 4082. As a force continues to be applied to the forearm support 4008 to move the forearm support 4008 to the end of its constrained travel zone (the block 4070) and moves the tool relative to tissue (the block 4072), the control circuit can continue to monitor the distance ($d_t$) (the block 4074) and maintain the gross motion mode (block 4082) while the distance ($d_t$) is greater than or equal to the threshold distance ($D_{critical}$).

If the distance ($d_t$) becomes less than the threshold distance ($D_{critical}$), the gross motion mode can be deactivated at a block 4076. With the gross motion mode deactivated, control motions for the robotic tool can be controlled with limited translation of the forearm support 4008 within the travel zone at a block 4078 (e.g. the travel zone 4050 in FIG. 47) and/or with the actuations to the wrist(s) (e.g. the wrist 4010 and/or the junction 4016) and/or to the handpiece 4020 at a block 4080. The control circuit can continue to monitor the distance ($d_t$) (the block 4074) and deactivate the gross motion mode (the block 4076) as long as the distance ($d_t$) is less than the threshold distance ($D_{critical}$).

During the gross motion mode, the surgical tool and end effector thereof can be driven in the directions detected by the forces at the space joint 4006 and applied by the forearm support 4008 until the forces are removed and the central portion 4002 is biased back to the home position. Upon removal of the forces to the space joint 4006 during the gross motion mode, the driving forces supplied to the end effector can terminate as well.

Referring again to FIGS. 44-49, the input control device 4000 has been described as having a mechanical joint 4042 intermediate the space joint 4006 and the forearm support 4008, which permits movement of the forearm support 4008 (and the entire collective unit 4011) relative to the base 4004 within the travel zone 4050. The travel zone 4050 can provide a precision control zone for the surgeon to move the handpiece 4020 to supply precision control motions to an end effector. In other instances, similar to the input control device 1000, for example, the input control device 4000 may not include the additional mechanical joint 4042 intermediate the space joint 4006 and the forearm support 4008. In such instances, precision control motions can be applied to the space joint 4006; however, such control motions can be scaled according to data from a tissue proximity detection system as further described herein. Scaling algorithms can also be applied to the input control device 4000, for example.

Feedback

Surgeons may like to receive feedback during a robotic surgical procedure. Feedback can indicate a changed condition of the control system, such as a changed operational mode of an input control device, for example, and/or an updated condition at the surgical site, such as proximity data regarding the robotic surgical tool relative to tissue and/or relative to another robotic surgical tool and/or robotic arm, for example. Feedback can also be related to the condition of the patient, elapsed time during the surgical procedure or particular steps thereof, and/or an error state of the robotic surgical system and/or robotic surgical tool. Without instantaneous, or nearly instantaneous, indication of certain conditions directly to the surgeon, the surgeon may be unprepared and/or require an extended reaction and/or adjustment period, which may extend the duration of the surgical procedure. It can be challenging to provide such feedback directly to the surgeon during the surgical procedure, especially in instances in which a surgeon is positioned away from the surgeon's console and/or is not looking at the display screen of the surgeon's console.

An input control device can provide feedback to the surgeon to indicate a changed condition of the control system and/or an updated condition at the surgical site. For example, an input control device incorporating feedback capabilities may alert a surgeon when the control system has switched between operational modes, such as between a gross motion mode and a precision motion mode, for example. Additionally or alternatively, an input control device incorporating feedback capabilities may provide proximity alerts to the surgeon. In various instances, a proximity detection system communicatively coupled to the input control device can relay the proximity data to the various clutchless input control devices disclosed herein. Feedback can be provided intraoperatively and in real-time. In certain instances, the feedback can be provided to the surgeon via the input control device regardless of the surgeon's position within the operating room and/or without requiring a surgeon's console and/or display screen, for example. In such instances, the surgeon can obtain instantaneous, or nearly instantaneous, indications and/or alerts, which can enable the surgeon to react in a timely manner and/or to adjust his or her input control motions to the input control device accordingly.

Referring now to FIG. 51, control logic 6068 for an input control device, such as the input control device 4000 (FIGS. 44-49), for example, is shown. The control logic 6068 includes the logic blocks 4070, 4072, 4074, 4076, 4078, 4080, and 4082 described herein with respect to FIG. 50. Additionally, the control logic 6068 includes a block 6084 following a determination that the distance ($d_t$) is less than the threshold distance ($D_{critical}$) at the block 4074. Based on the tissue proximity data, the gross motion mode is deactivated at the block 4076. Feedback is provided to the surgeon via the input control device at the block 6084. In various instances, blocks 6084 and 4076 can be implemented concurrently or nearly concurrently. Block 6084 can immediately precede block 4076 and/or block 4076 can immediately precede block 6084. By providing feedback at the block 6084, the surgeon can be notified and/or alerted to the changed operational mode of the input control device and can adjust his or her input control motions accordingly.

The feedback provided at the block 6084 can include tactile feedback, visual feedback, and/or auditory feedback, for example. Tactile feedback includes vibratory buzzing, clicking, scalable resistance forces, and/or other haptic feedback; visual feedback includes an illuminated light and/or light pattern and/or alert(s) provided via an LED and/or display screen on the input control device; and auditory feedback includes noises like beeping, humming, and/or computer-generated verbal warnings and/or notifications.

In various instances, an input control device having feedback capabilities can include a feedback generator, which is configured to generate vibratory or haptic feedback and provide feedback, such as a buzz and/or series of buzzes, for example, to the surgeon utilizing the input control device. An input control device 6100 is shown in FIG. 52. The input control device 6100 can be similar to the input control device 4000 (FIGS. 44-49) in many respects. In certain instances, the input control device 6100 can be identical to the input control device 4000 except that the input control device 6100 also includes at least one feedback generator and the associated control circuits. The feedback generators can be positioned to provide feedback to the surgeon holding and/or engaged with the input control device 6100. Exemplary feedback generators 6180a, 6180b, 6180c are embedded in the input control device 6100. For example, the feedback generator 6180a is positioned in the forearm support 4008, the feedback generator 6180b is positioned in the shaft 4012, and the feedback generator 6180c is positioned in the opposing fingers 4022 of jaw on the handpiece 4020. In various instances, a feedback generator can be positioned in each opposing finger 4022 of the handpiece 4020. The reader will appreciate that the feedback generators 6180a, 6180b, and 6180c can be positioned at alternative locations in the input control device 6100 (e.g. proximal to the wrist along the shaft 4012 and/or within the base 4004 of the input control device 6100). Moreover, in various instances, the input control device 6100 can include less than three feedback generators or more than three feedback generators. Additionally or alternatively, feedback can be provided by speakers, LEDs, and/or screens, for example, positioned on an outer surface of the input control device 6100.

Referring now to FIG. 53, travel zones for the input control device 6100 are shown. The travel zones include an inner precision motion zone 6150, and an outer gross motion zone 6152. The precision motion zone 6150 can correspond to the travel zone 4050 for the input control device 4000 shown in FIG. 47. For example, the forearm support 4008 (or supporting shaft thereof) is configured to move within the precision motion zone 6150 to supply input control motions to the robotic surgical tool. Upon reaching the end of the precision motion zone 6150, an increased force applied to the forearm support 4008 can move the supporting shaft thereof into the gross motion zone 6152.

The precision motion zone 6150 and the gross motion zone 6152 define concentric rings having different radial distances. The precision motion zone 6150 is defined or bounded by an inner boundary 6151 and an outer boundary 6153. A radial distance or width ($d_{precision}$) spans the space between the inner boundary 6151 and the outer boundary 6153. The gross motion zone 6152 is defined or bounded by an inner boundary 6155 and an outer boundary 6157. A radial distance or width ($d_{gross}$) spans the space between the inner boundary 6155 and the outer boundary 6157. In various instances, the inner boundary 6155 of the gross motion zone 6152 can be collinear with the outer boundary 6153 of the precision motion zone 6150.

The radial distance ($d_{precision}$) defining the precision motion zone 6150 is larger than the radial distance ($d_{gross}$) defining the gross motion mode. For example, the radial distance ($d_{precision}$) for the precision motion mode 6150 can be between 2.0 cm and 6.0 cm, and the radial distance ($d_{gross}$) for the gross motion mode 6152 can be between 1.0 mm and 5.0 mm. In certain instances, the radial distance ($d_{precision}$) of the precision motion zone 6150 can be at least an order of magnitude larger than the radial distance ($d_{gross}$) of the gross motion zone 6152. Although the zones 6150, 6152 are depicted as planar, two-dimensional zones in FIG. 53, the reader will appreciate that the zones 6150, 6152 can define three-dimensional zones in various instances. In still other instances, the forearm support 4008 can be movable along a single axis and, in such instances, the zones 6150, 6152 can define one-dimensional paths.

In various instances, the feedback generators (e.g. one of the generators 6180a, 6180b, and 6180c in FIG. 52) can be configured to provide feedback when the forearm support 4008 approaches and/or reaches the boundary between the precision motion zone 6150 and gross motion zone 6152. In certain instances, the feedback generators can provide different types, degrees, and/or patterns of feedback. For example, a first type of feedback can be provided as the forearm support 4008 approaches the boundary between the precision motion zone 6150 and the gross motion zone 6152, and a different type of feedback can be provided as the forearm support 4008 crosses the boundary. The different types of feedback can provide additional information to the surgeon, which can facilitate the surgeon's decision-making process and/or planning.

Feedback can be provided at the various boundaries of the different zones and/or different operational modes of the user input device 6100. As further described herein, the various input control devices can include multiple joints, including multi-dimensional space joints and wrists, among other joints. Feedback can be provided to the surgeon when any joint limit is approached and/or met. In certain instances, the feedback can include a resistance force that increases as the joint limit is met, such as when the forearm support 4008 moves away from the home position and approaches the boundary 6153, 6155 between the precision motion zone 6150 and the gross motion zone 6152.

In certain instances, referring again to FIG. 52, the input control device 6100 includes at least one detent arrangement for providing tactile feedback to the surgeon. For example, the input control device 6100 includes a detent arrangement 6182 intermediate the base 4004 and the forearm support 4008. The detent arrangement 6182 can be positioned at the limit or boundary 6153, 6155 (FIG. 53) between the precision motion zone 6150 and the gross motion zone 6152. In such instances, when the force exerted by the surgeon on the forearm support 4008 moves the forearm support 4008 from the precision motion mode 6150 to the gross motion mode 6152, the detent arrangement 6182 can provide a tactile indication to the surgeon that the input control device 6100 has transitioned to gross motion control. For example, the detent arrangement 6182 can include a notch and a spring-loaded element, such as a pin, pawl, dog, and/or ball, for example. The notch can be defined in the base 4004 and the spring-loaded element can be supported by the forearm support 4008, for example. As the forearm support 4008 is pushed by the surgeon, the spring-loaded element can engage the notch and be temporarily restrained until a larger force exerted on the forearm support 4008 moves the spring-loaded element past the notch. The geometry of the notch and/or the interplay between the notch and the spring-loaded element can control the amount of resistance and corresponding tactile force delivered to the surgeon. In various instances, a row of notches can provide tactile feedback and/or clicking at more than one location, and, in certain instances, different notch geometries can provide different types of feedback at the different locations.

In various instances, the forearm support 4008 can be biased toward the central home position within the precision motion zone 6150. For example, a spring arrangement can bias the forearm support 4008 toward the center of the concentric rings shown in FIG. 53. In certain instances, the spring arrangement can include a dampener configured to dampen or prevent "snap-back" vibrations.

Feedback generators can be incorporated into alternative input control devices. For example, feedback generators can be incorporated into input control devices having different geometries and/or configurations. Moreover, feedback generators can be incorporated into a wireless and/or untethered input control device and/or modular handpiece portion of an input control device. As another example, an input control device 6200 is shown in FIG. 54. The input control device 6200 can be similar to the input control device 1000 (FIGS. 6-11) in many respects. In certain instances, the input control device 6200 can be identical to the input control device 1000 except that the input control device 6200 also includes at least one feedback generator and the associated control circuits. The feedback generators can be positioned to provide feedback to the surgeon holding and/or engaged with the input control device 6200. Exemplary feedback generators 6280*a* and 6280*b* are embedded in the input control device 6200. For example, the feedback generator 6280*a* is positioned in the end effector actuator 1020 and, specifically in one of the opposing fingers 1022. In certain instances, a feedback generator can be positioned in both opposing fingers 1022. Additionally, the feedback generator 6180*b* is positioned in the joystick 1008. The reader will appreciate that the feedback generators 6280*a* and 6280*b* can be positioned at alternative locations in the input control device 6100 (e.g. in the wrist 1010, the shaft 1012, and/or within the base 1004) of the input control device 6200. Moreover, in various instances, the input control device 6200 can include less than two feedback generators or more than two feedback generators.

In various instances, the feedback generators for an input control device, such as the feedback generators 6180*a*, 6180*b*, 6180*c*, 6280*a*, and 6280*b* (FIGS. 52 and 53), for example, can be haptic feedback generators, which generate vibratory motion of the input control device or a component thereof. Such vibratory motions can be detected, observed and/or felt by the surgeon using the input control device. For example, the feedback generators can create vibratory/haptic feedback using an eccentric rotating mass (ERM) actuator, which includes an unbalanced weight attached to a motor shaft. As the shaft rotates, the spinning of this irregular mass causes the actuator, and in turn, the input control device and/or component thereof, to shake, buzz, or vibrate. Alternative haptic feedback generators can utilize a linear resonant actuator (LRA), which can reciprocate a mass along a linear path utilizing a magnetic coil, and piezoelectric actuators, among other feedback generators, for example. Because various input control devices described herein do not rely on electromagnetic (EM) tracking to determine the input control motions supplied and delivered by the surgeon, mechanical actuators and motors for generating tactile, haptic feedback can be incorporated into such input control devices without interfering with the controlling capabilities thereof.

In various instances, the feedback generators can provide vibratory and/or buzzing feedback to indicate a changed condition, as described herein. In other instances, the input control device can include force feedback generators, which are configured to generate a force and positioned to deliver the force to the surgeon. For example, the forearm support 4008 can exert a scaled resistance as the forearm support 4008 moves toward the gross motion zone 6152. In one aspect, the scaled resistance can increase as the forearm support 4008 moves toward the gross motion zone 6152. In another aspect, the opposing fingers 4022 can be configured to exert a scaled (e.g. increasing) resistance force as the opposing fingers 4022 approach a joint limit thereof and/or approach each other to clamp the tissue, for example.

In still other aspects, the input control device can receive proximity data regarding the proximity of the surgical tool controlled by the input control device with respect to other surgical tools and/or robotic arms at the surgical site. For example, the control system for the input control device can alert the surgeon when the controlled surgical tool is in close proximity to another surgical tool and/or robotic arm. The feedback can be provided as at least one of the various tactile, auditory, and/or visual feedbacks described herein.

Additionally or alternatively, the various feedback actuators described herein in connection with the input control devices 6100 and 6200, for example, can be utilized to communicate a patient alert and/or an error state to the surgeon. Error states include errors to the robotic system and/or the robotic surgical tool, which can occur when a robotic surgical tool is attached to the robotic arm improperly, when the robotic surgical tool is loaded incorrectly and/or positioned out of line, and/or when the robotic surgical tool is fired improperly, for example. Alerts can also be provided to the surgeon based on the elapsed time and/or the physiological condition of the patient. For example, during certain time-sensitive procedures, the condition of the patient can depend on the duration of the procedure. A surgeon may want to receive feedback and/or alerts regarding the condition of the patient and/or the amount of elapsed time. For example, alerts provided directly to the surgeon via the input control device engaged by the surgeon can be used during video-assisted thoracic (VAT) procedures, Pringle maneuvers during a liver procedure to prevent a Pringle blood occlusion, or during a nephrectomy when a bulldog clamp procedure is used to temporarily stop the flow of blood. The feedback can be provided as at least one of the various tactile, auditory, and/or visual feedbacks described herein.

The various feedback data, alerts, and/or error states described herein can also be communicated to the surgeon via the monitor 1088 at the adjustable workspace 1080 (FIGS. 16 and 17). In such instances, the information can be communicated to the surgeon, as well as other personnel in the surgical theater and/or positioned to view the monitor 1088.

Surgeons utilizing surgical robots to perform a surgical procedure may appreciate tactile feedback that corresponds to one or more conditions at the surgical site. For example, the input control device(s) utilized by the surgeon(s) during the surgical procedure may receive feedback signals from the surgical robot corresponding to conditions experienced by a surgical tool at the surgical site. As an example, the surgical tool may experience a force or pressure from the tissue clamped between the jaws of the end effector. Such a tissue force can depend on various characteristics of the tissue, including the type, thickness, density, and/or toughness of the tissue, for example. A surgeon may want to monitor the force exerted by the tissue on the jaws to ensure the tissue is not subjected to excessive forces, which may traumatize and/or damage certain tissue, and/or subjected to insufficient forces, which may correspond to unsatisfactory staple formation and/or tissue seals.

As described herein, various input control devices for robotic surgical tools can include a pair of opposing jaws or fingers that correspond to the opposing jaws of the end effector of the robotic surgical tool. The opposing jaws can extend distally with respect to an articulation joint or wrist of the input control device mirroring the configuration of a robotic surgical tool having an articulation joint along the shaft and jaws extending distally from the shaft. To affect opening or closing motions of one or more of the end effector jaws, the surgeon can apply corresponding opening or closing motions to the appropriate jaw(s)/opposing fingers of the input control device. In such instances, the opposing fingers of the input control device can provide an intuitive actuator for controlling the end effector jaws. In various instances, a surgeon may appreciate force feedback at the opposing fingers of the input control device that corresponds to the force of the tissue on the end effector jaws. Such an arrangement can provide intraoperative, dynamic feedback to the surgeon during the surgical procedure. Moreover, such feedback can be proportionate and commensurate with the input control motions applied to the input control device.

For example, in one aspect, a control system can include a robotic tool configured to detect a property of a tissue at a surgical site. The control system can also include an input control device and a control circuit. The input control device can include a base, a joystick coupled to the base, and a handpiece coupled to the joystick, wherein the handpiece includes a variable resistance assembly comprising a piston. The variable resistance assembly can also include an energized coil, wherein output control signals to the variable resistance assembly are configured to adjust a current supplied to the energized coil. The handpiece can also include a linear actuator configured to translate the piston, which can be a magnetic element, relative to the energized coil. The handpiece can also include a first jaw coupled to the piston and a second jaw coupled to the piston, wherein the first jaw and the second jaw are configured to receive user input control motions. The control circuit can be configured to receive jaw control signals indicative of the user input control motions received by the first jaw and the second jaw, provide first output control signals to the robotic tool based on the jaw control signals, receive tissue property signals indicative of the property of the tissue, and provide second output control signals to the variable resistance assembly in response to the property of the tissue. Alternative variable resistance assemblies and arrangements thereof are further described herein.

Referring now to FIG. 55, an input control device 7000 is shown. The input control device 7000 can be similar to the input control device 1000 (FIGS. 6-11) in many respects. In certain instances, the input control device 7000 can be identical to the input control device 1000 except that the input control device 7000 also includes a variable resistance assembly 7080 and the associated control circuits. For example, the input control device 7000 includes the base 1004, the space joint 1006, the joystick 1008, and the end effector actuator or handpiece 1020. The input control device 7000 also includes the wrist 1010, which is offset from the space joint 1006 by a shaft 7012 extending along a shaft axis S that is parallel to the axis X in the configuration shown in FIG. 55. For example, the joystick 1008 can extend upright vertically from the central portion 1002 and the base 1004, and the joystick 1008 can support the shaft 7012.

The shaft 7012 includes the variable resistance assembly 7080. The variable resistance assembly 7080 can be secured to the shaft 7012 and/or retained within a central channel within the shaft 7012. The variable resistance assembly 7080 is configured to generate a variable spring rate or resistance forces ($F_{R1}$ and $F_{R2}$) utilizing electromagnetic induction. The resistance forces ($F_{R1}$ and $F_{R2}$) are applied to the opposing fingers 1022, such as by a pair of linkages 7023 extending between the opposing fingers 1022 and the variable resistance assembly 7080.

The variable resistance assembly 7080 can be an electromagnetic force generator. For example, the variable resistance assembly 7080 includes a magnetic piston 7084 and a coil 7082, which can be formed from a conductive wire or plurality of conductive wires that are coupled to a power source and energized by an electric current therethrough. The magnetic piston 7084 is movably supported relative to the coil 7082. For example, the piston 7084 can be supported by a linear actuator. The variable resistance forces ($F_{R1}$ and $F_{R2}$) can be controlled by the movement of the piston 7084 relative to the coil 7082. For example, the piston 7084 can be moved along and/or within a portion of the length of the coil 7082. By adjusting the current through the coil 7082, the magnetic force around the piston 7084 can change, which can apply a force to displace the piston 7084. Stated differently, the variable current affects the resistance of the piston 7084 to translation relative to the coil 7082. The spring rate and/or resistance forces ($F_{R1}$ and $F_{R2}$) are, thus, magnetically controlled by the electromagnetic force, which is affected by the current supplied to the coil 7082.

The input control device 7000 also includes a pair of connectors 7085 extending between the variable resistance assembly 7080 and each linkage 7023. For example, the linkages 7023 can connect the magnetic piston 7084 of the resistance assembly 7080 to the opposing fingers 1022. Movement of the fingers 1022, such as by a surgeon applying an actuation closure motion to the fingers 1022, for example, is configured to move the linkages 7023 coupled thereto and, thus, apply a force to the magnetic piston 7084 of the resistance assembly 7080. In alternative aspects, the linear actuator for the resistance assembly 7080 can include additional linkages, screws, such as friction screws with anti-backlash nuts and/or ball screws, belt and pulley systems, rack and pinion systems, a piezoelectric actuator, and/or alternative motors arrangements.

The variable resistance assembly 7080 is configured to provide resistance to both fingers 1022 of the input control device 7000. Conversely, existing handheld surgical instruments, such as a powered, handheld surgical stapler, for example, may only include a single trigger for actuating the end effector jaws and, thus, only generate a resistance force on the single trigger even though multiple end effector jaws are actuated and/or utilized to clamp the tissue. In the arrangement depicted in FIG. 55, the resistance forces ($F_{R1}$ and $F_{R2}$) are equal. In other instances, the resistance forces ($F_{R1}$ and $F_{R2}$) can be independent, as further described herein.

The resistance forces ($F_{R1}$ and $F_{R2}$) can correspond to the force from tissue engaged by the opposing end effector jaws. Referring now to FIG. 56, a graphical representation 7086 of voltage (V) in the coil 7082 of the variable resistance assembly 7080 relative to the tissue force ($F_{tissue}$) is shown. The voltage (V) is proportional to the tissue force ($F_{tissue}$). As the magnetic piston 7084 moves relative to the coil 7082, a voltage can be induced in the coil 7082. The magnitude of the induced voltage is proportional to the velocity of the relative movement between the magnetic piston 7084 and the coil 7082. A graphical representation 7088 of the resistance force ($F_R$) applied to the opposing fingers 1022 relative to the tissue force ($F_{tissue}$) is shown in FIG. 57. The resistance force ($F_R$) is proportional to the tissue force ($F_{tissue}$). In other instances, a stepped or non-linear resistance force ($F_R$) can be generated in response to the changing tissue force ($F_{tissue}$).

Referring now to FIG. 58, control logic 7090 for an input control device, such as the input control device 7000 (FIG. 55), for example, is configured to adjust the resistance forces ($F_{R1}$ and $F_{R2}$) applied to the end effector actuators, such as the opposing fingers 1022, for example. The control logic 7090 can be utilized in the control circuit 832 (FIG. 25), the control circuit 1400 (FIG. 11C), the combinational logical circuit 1410 (FIG. 11D), and/or the sequential logic circuit 1420 (FIG. 11E), for example. At a block 7092, the tissue force ($F_{tissue}$) at the end effector is determined. The tissue force ($F_{tissue}$) can be detected by measuring the current drawn by a motor during the closing or tissue clamping motion of the end effector. A greater amount of current can correspond to a greater tissue force ($F_{tissue}$), for example. At a block 7094, the tissue force ($F_{tissue}$) can be communicated to a control circuit for the input control device. In response to the detected and communicated tissue force ($F_{tissue}$), the control circuit can adjust the resistance force ($F_R$) applied to the fingers 1022 at a block 7096. The blocks 7092, 7094, 7096 can be repeated to update the resistance force ($F_R$) in response to a changing tissue force ($F_{tissue}$).

In certain instances, the control logic 7090 can be configured to communicate additional and/or alternative information to the surgeon via the input control device 7000 (FIG. 55). For example, the control logic 7090 can communicate contact of a robotic surgical tool controlled by the input control device 7000 with an anatomical structure or tissue at the surgical site. In such instances, a sensor (e.g. a capacitive sensor) on the robotic surgical tool can be configured to detect contact with tissue. Upon detecting such contact, the input control device 7000 can adjust a resistance force applied to the fingers 1022 of the input control device 7000, utilizing the variable resistance assembly 7080, for example.

In certain instances, a variable resistance assembly for an input control device can include at least one motor configured to apply adjustable resistance forces to the end effector actuators thereof. For example, an input control device can include a pair of variable resistance assemblies that are movable independently. The variable resistance assemblies can constitute electric motors and/or linear actuators. For example, the control system can use a motor to physically adjust (increase or decrease) the force required to actuate the fingers 1022 in order to apply closure motions to the end effector jaws. The force adjustment can depend on the force profile at the end effector of the robotic surgical tool.

In certain instances, the resistance forces ($F_{R1}$ and $F_{R2}$) applied to the fingers 1022 can be independent. Depending upon the orientation and position of the surgical end effector at the surgical site, the forces exerted on the end effectors jaws could be different and, in such instances, the independent resistance assemblies could apply different resistance forces to the respective fingers of the input control device.

Additionally or alternatively, the variable force profile generated by the variable resistance assembly can be tool-specific. For example, for a first surgical tool the variable force profile can include at least one peak and dip before the end of the stroke, and for a second surgical tool the variable force profile can include a single peak at the end of the stroke. The first surgical tool can be an ultrasonic device, for example, having at least two bistability states during a closure stroke. Upon advancing the closure stroke over-center between bistable states, the force profile generated by the variable resistance assembly can peak. The force profile can subsequently drop in the second bistable state before the end of the closure stroke. The second surgical tool can be a grasper, for example, defining a linear force profile during a closure stroke. In such instances, the variable force profile generated and delivered by the variable resistance assembly can be selected based on the surgical tool that is operably coupled to and controlled by the input control device. Alternative force profiles (e.g. stepped, curved, wavy, sinusoidal, and/or exponential) are also contemplated. The force profile can be selected based on the geometry and/or design of the surgical tool and/or the expectations of the surgeon, for example. In various instances, the variable resistance force can be selected to match or coordinate with the variable resistance force delivered to the surgeon using the corresponding non-robotic, handheld surgical tool.

Various input control devices described herein do not rely on EM tracking and, thus, the input control devices can incorporate motors and other feedback generators utilizing magnetic elements to provide feedback without interfering with the control signals for the input control device.

Often, multiple surgical tools are utilized during a robotic surgical procedure. Surgical tools can flow in and out of use and/or can be releasably attached to an arm of the surgical robot. In one instance, a first robotic tool can be utilized during an initial portion of the surgical procedure and can be subsequently replaced, or exchanged, for a second robotic tool during a later portion of the surgical procedure. Tool swapping is common during complex surgical procedures. In one instance, a bipolar tool can be replaced with a monopolar tool, an ultrasonic tool, a grasper, a stapler, a suction tool and/or an irrigation tool, for example. In certain instances, a clinician located within the sterile field is positioned to swap or exchange the surgical tools attached to a robotic arm.

Additionally or alternatively, a single input control device can be selectively paired to different surgical tools. In one aspect, the workspace for the surgeon may include fewer active input control devices than robotic arms. For example, the workspace may have two input control devices, one for each of the surgeon's hands; however, the surgical robot may include more than two robotic arms. In such instances, a input control device can be selectively paired to surgical tools coupled to different robotic arms.

When an input control device is paired with different surgical tools—e.g., when surgical tools are either exchanged or control by an input control device switches between different robotic arms/surgical tools—the orientation of the input control device may not correspond to, or match, the orientation of the second surgical tool. As an example, the jaws of a first surgical tool can be driven to a closed orientation by an input control device. When a second surgical tool is paired to that same input control device, the jaws of the second surgical tool may be in an open orientation and, thus, may not match the closed orientation of the jaw actuator on the input control device. In such instances, though the second surgical tool paired with the input control device is configured to receive closure motions, the jaw actuator of the input control device may be unable to receive further closure motions and, thus, cannot receive input control motions to close the jaws of the second surgical tool. Additionally or alternatively, when the orientation of the input control device does not correspond to the orientation of the paired surgical tool, the actuation of other input control motions, such as articulation control motions, for example, may be inhibited or limited and/or positioned in a less intuitive configuration or arrangement for the surgeon.

In various instances, an input control device can be configured to receive control motions based on the position of the surgical tool paired with the input control device. For example, when the position of a portion of a surgical tool does not match the position of the corresponding actuator on the input control device, the actuator can be driven to a suitable position that corresponds with the orientation of the portion of the surgical tool. The input control device can include a linear actuator, for example, which is configured to move one or more of the jaws of the input control device to match the angular orientation of the one or more jaws of the surgical tool paired with the input control device. In one aspect, a control system for a robotic surgical system can include a control circuit configured to receive first input control signals indicative of user input control motions received by a movable actuator on an input control device, provide first output control signals to a robotic tool based on the first input control signals, receive second input control signals from the robotic tool indicative of the position of a movable element of the robotic tool, and provide second output control signals to a linear actuator of the input control device based on the second input control signals.

By matching the position of the drivable actuator on the input control device to the driven element on the robotic surgical tool, the flow of surgical tools during a surgical procedure can be improved. For example, an input control device can switch between controlling a first surgical tool and a second surgical tool with minimal interruptions and/or without requiring the direct involvement of the surgeon and/or other clinicians in the surgical theater. For example, the control circuit can automatically adjust the position of one or more drivable actuators on an input control device upon pairing of a surgical tool with the input control device. In such instances, the transition can be seamless and efficient, for example. Moreover, in various instances, the control circuit can continuously and/or periodically check that the position of the drivable actuator in the input control device corresponds to the position of the driven element on the robotic surgical tool and implement a closed-loop adjustment to match the positions. Additionally or alternatively, the control circuit can provide an alert and/or error message to the surgeon via the various feedback systems described herein when the positions do not match and/or do not fall within a range of acceptable positions.

Referring now to FIG. 59, an input control device 8000 is shown. The input control device 8000 can be similar to the input control device 1000 (FIGS. 6-11) in many respects. In certain instances, the input control device 8000 can be identical to the input control device 1000 except that the input control device 8000 also includes a jaw actuation assembly 8080 and the associated control circuits. For example, the input control device 8000 includes the base 1004, the space joint 1006, the joystick 1008, and the end effector actuator or handpiece 1020. The input control device 8000 also includes the wrist 1010, which is offset from the space joint 1006 by a shaft 8012 extending along a shaft axis S that is parallel to the axis X in the configuration shown in FIG. 59. For example, the joystick 1008 can extend upright vertically from the central portion 1002 and the base 1004, and the joystick 1008 can support the shaft 8012.

The shaft 8012 includes the jaw actuation assembly 8080. The jaw actuation assembly 8080 can be secured to the shaft 8012 and/or retained within a central channel in the shaft 8012. The jaw actuation assembly 8080 is configured to drive the fingers 1022 on the handpiece 1020 in response to input control signals indicative of a position or orientation of the jaw(s) on the robotic surgical tool paired with the input control device 8000.

The jaw actuation assembly 8080 includes a linear actuator 8081, which is configured to apply opening and closing motions to the fingers 1022. For example, the linear actuator 8081 includes a reciprocating element 8082 that is pivotably connected to connecting rods 8084. Each connecting rod 8084 is pivotably connected to one of the fingers 1022. With such an arrangement, longitudinal displacement of the reciprocating element 8082 by the linear actuator 8081 is configured to pivot the fingers 1022 about the wrist 1010. For example, as the reciprocating element 8082 is drawn proximally (in the proximal direction PD) toward the wrist 1010, the fingers 1022 are configured to pivot outwardly to define an increased angle $\theta_C$ therebetween. Similarly, as the reciprocating element 8082 is pushed distally (in the distal direction DD) away from the wrist 1010, the fingers 1022 are configured to pivot inwardly to define a decreased angle $\theta_C$ therebetween.

The angular orientation of the fingers 1022 and, thus the angle $\theta_C$ defined between the fingers 1022, is adjusted by the linear actuator 8081. In various instances, the linear actuator 8081 can include a rack and pinion system, which can be operably connected to a servomechanism. For example, referring now to FIG. 60, the linear actuator 8081 for the jaw actuation assembly 8080 can include a rack 8182 operably connected to a servomechanism through a gear 8184 and/or gear train. Alternative linear actuators for the jaw actuation assembly 8080 are contemplated. For example, the linear actuator can include one or more linear motors, hydraulic and/or pneumatic actuators, screws, such as friction screws with anti-backlash nuts and/or ball screws, belt and pulley systems, rack and pinion systems, and/or piezoelectric actuators.

In various instances, the linear actuator 8081 is configured to drive both fingers 1022 of the handpiece 1020. In the symmetrical arrangement of FIG. 59, the fingers 1022 can be pivoted equally in response to an actuation of the linear actuator 8081. In other instances, the fingers 1022 can be asymmetrically actuated in response to an actuation of a linear actuator. In still other instances, the jaw actuation assembly 8080 can include more than one linear actuator. Referring now to FIG. 61, a jaw actuation assembly 8280 including a pair of linear actuators 8281 is shown. The jaw actuation assembly 8280 can be utilized with an input control device, such as the input control device 8000, for example. Each linear actuator 8281 can be coupled to one of the fingers of the input control device (e.g. the fingers 1022 in FIG. 59) by a connecting rod 8284 such that the rotational displacement of each finger 1022 is independently controlled by the independent linear displacement of respective reciprocating elements 8282 of the linear actuators 8281.

The jaw actuation assembly 8080 is configured to drive the fingers 1022 of the input control device 8000 to a desired angular orientation. For example, the linear actuator 8081 can be actuated to automatically match the position or orientation of the fingers 1022 to the position or orientation of the jaws on a robotic surgical tool. Referring now to FIG. 62, a table 8090 provides corresponding positions for the end effector actuators on an input control device, such as the fingers 1022 on the input control device 8000 (FIG. 59), for example, and the jaws of a robotic surgical tools, such as the opposing jaws 1064 of the end effector 1062 (FIGS. 13A, 14A, and 15A), for example, throughout a surgical procedure involving the swapping or surgical tools.

For example, with Tool #1 paired with the input control device, the fingers on the input control device can transition from an angle $\theta_{C1}$, an open controller configuration, to an angle $\theta_{C2}$, a partially-closed controller configuration, to drive the jaws of Tool #1 from an angle $\theta_{T1}$, an open tool configuration, to an angle $\theta_{T2}$, a partially-closed tool configuration. The angle $\theta_{C1}$ corresponds to the angle $\theta_{T1}$, and the angle $\theta_{C2}$ corresponds to the angle $\theta_{T2}$. In various instances, corresponding angles can match or be equal.

Continued actuations of the fingers of the input control device can continue to adjust the angular orientation of the jaws of Tool #1.

At a later time, the input control device may be paired with a different surgical tool, such as Tool #2 or Tool #3. Upon pairing the input control device with Tool #2, which has its jaws oriented at an angle $\theta_{T3}$, a closed tool configuration in which the jaws are not angularly offset from one another, the fingers on the input control device can be driven inwardly to an angle $\theta_{C3}$, a closed controller configuration, which corresponds to the angle $\theta_{T3}$. Subsequently or alternatively, the input control device can be paired with Tool #3, which has its jaws oriented at the angle $\theta_{T1}$, the open tool configuration. Upon pairing with Tool #3, the fingers on the input control device can be driven outwardly to the angle $\theta_{C1}$, the open controller configuration. The reader will appreciate that alternative surgical tools and angular positions are contemplated. In certain instances, the jaw actuation assembly 8080 and the linear actuator 8081 of FIG. 59 can be configured to affect the drive motions to the input control device shown in FIG. 62. In other instances, alternative linear actuators can be employed.

Referring now to FIG. 63, control logic 8100 for an input control device, such as the input control device 8000 (FIG. 59), for example, is configured to selectively drive robotic surgical tools in response to control signals from the input control device and to selectively drive the input control device in response to control signals from the robotic surgical tool. The angles referenced in the control logic 8100 can correspond to the angles shown in the table 8090 (FIG. 62). The control logic 8100 can selectively drive the end effector actuators, such as the opposing fingers 1022, for example, to correspond to the detected position of the jaws of the robotic surgical tool. The control logic 8100 can be utilized in the control circuit 832 (FIG. 25), the control circuit 1400 (FIG. 11C), the combinational logical circuit 1410 (FIG. 11D), and/or the sequential logic circuit 1420 (FIG. 11E), for example.

At a block 8102, the input control device defines the angle $\theta_{C1}$ between the end effector actuators. At a block 8104, the control logic 8100 is configured to check the robotic surgical tool paired with the input control device and match the angle between the end effector actuators to the angle defined between the opposing jaws of the paired robotic surgical tool. For example, if the robotic surgical tool paired with the input control device defines the angle $\theta_{T1}$ between the jaws, the fingers of the input control device can remain in the same position. At the outset of the surgical procedure and/or when a new surgical tool is detected by or paired with the input control device, the control logic can automatically coordinate the angles such that the angle between the end effector actuators corresponds to the angle defined between the opposing jaws of the paired robotic surgical tool.

At a block 8106, the input control device—upon receiving an input control motion from a surgeon that, for example, moves the end effector actuators of the input control device—is configured to drive the jaws of the robotic surgical tool from angle $\theta_{T1}$ to the angle $\theta_{T2}$ as the end effector actuators move through a corresponding range of motion, or corresponding degrees, from the angle $\theta_{C1}$ to the angle $\theta_{C2}$ at the block 8108. In certain instances, a surgeon may activate a single end effector actuator and/or can pivot the end effector actuators asymmetrically and the jaw(s) of the robotic surgical tool can be driven accordingly. For example, certain surgical tools may only utilize a single moving jaw, which can pivot relative to a fixed jaw, for example. In such instances, one of the end effector actuators can remain stationary while the other end effector actuator moves. In certain instances, the end effector actuator representing a fixed jaw can be selectively locked out when the input control device is paired with such a surgical tool. In still other instances, different surgical tools can define different ranges of motions. For example, depending on the geometry of an articulation assembly and/or pivot joint, the jaw(s) of one surgical tool can have a larger range of motion than the jaw(s) of another surgical tool. Upon pairing of the input control device with a surgical tool, the range of motion of the end effector actuators can be selectively restrained to correspond to the range of motion of the surgical tool. For example, a portion of the range of motion of an end effector actuator on an input control device can be locked out when the robotic surgical tool paired with the input control device has a more limited range of motion.

At a block 8110, the robotic surgical tool paired with the input control device can be swapped for a different surgical tool. Swapping of surgical tools can constitute the physical removal of one surgical tool from a robotic arm and the attachment of another surgical tool to the robotic arm. Additionally or alternatively, swapping surgical tools can constitute pairing or establishing communication paths with a different surgical tool, which may be attached to a different robotic arm, for example. Swapping of the surgical tools can be initiated by a clinician within the sterile field or by a control input to the surgical robot, such as a command provided by the surgeon to the input control device and/or at the surgeon's console, for example.

At a block 8112, the previous surgical tool has been exchanged for Tool #2. Tool #2 can be an entirely different type of surgical tool, a similar tool having different features/capabilities, or the same type of surgical tool in a different configuration, for example. At the block 8112, Tool #2 defines the angle $\theta_{T3}$ between the jaws. Referring again to FIG. 62, the angle $\theta_{T3}$ corresponds to a closed jaw position in which the angle between the jaws is zero. At a block 8114, the end effector actuators of the input control device are driven inwardly to a new angular orientation, the angle $\theta_{C3}$, a closed controller configuration in which the angle between the opposing fingers is zero, which corresponds to the angle $\theta_{T3}$. Upon matching the angle between the end effector actuators to the angle defined between the opposing jaws of Tool #2, the input control device is ready to receive input control motions and the control circuit can supply output control signals to Tool #2 based on the input control motions applied to the input control device by the surgeon. For example, at a block 8116, the input control device drives Tool #2 from the angle $\theta_{T3}$ to the angle $\theta_{T2}$. As a result, the input control device can again define the angle $\theta_{C2}$ and can continue controlling the robotic surgical tool at a block 8108 through the surgical procedure or until another "tool swap" occurs at the block 8110.

At a block 8118, Tool #3 has replaced the previous surgical tool. Tool #3 can be an entirely different type of surgical tool, a similar tool having different features/capabilities, or the same surgical tool in a different configuration, for example. At the block 8118, Tool #3 defines the angle $\theta_{T1}$ between the jaws. Referring again to FIG. 62, the angle $\theta_{T1}$ corresponds to an open jaw position. At the block 8120, the end effector actuators of the input control device are driven outwardly to the angle $\theta_{C1}$, an open controller configuration that corresponds to the angle $\theta_{T1}$. Upon matching the angle between the end effector actuators to the angle defined between the opposing jaws of Tool #3, the input control device is ready to receive input control motions and the control circuit can supply output control signals to Tool #3 based on the input control motions applied to the input control device by the clinician. For example, at the block 8106, the input control device drives Tool #3 from the angle $\theta_{T1}$ to the angle $\theta_{T2}$. As a result, the input control device can again define the angle $\theta_{C2}$ and can continue controlling Tool #3 at the block 8108 through the surgical procedure or until another "tool swap" occurs at the block 8110.

In various instances, the various jaw actuator systems and linear actuators described herein can be utilized to effect a training mode, in which input control motions applied to the input control device can be limited. For example, the jaw actuation system 8080 and the linear actuator 8081 (FIG. 59) can draw the opposing fingers 1022 inwardly toward the shaft 8012 to form a secondary control portion, column, or virtual shaft, which can define a non-jaw actuation control portion, for example. Training modes and secondary control portions are further described in U.S. patent application Ser. No. 16/354,470, titled SEGMENTED CONTROL INPUTS FOR SURGICAL ROBOTIC SYSTEMS, now U.S. Patent Application Publication No. 2020/0289223, which has been incorporated by reference herein in its entirety.

EXAMPLES

Various aspects of the subject matter described herein are set out in the following numbered examples.

A list of Examples follows:

Example 1—A control system for a robotic surgical system, the control system comprising a surgical tool movable with respect to a tissue of a patient, an input control device configured to receive an input control motion. The input control device comprises a feedback generator. The control system further comprises a control circuit configured to receive an input control signal indicative of the input control motion received by the input control device, provide a first output control signal to the surgical tool based on the input control signal, determine a distance between the surgical tool and the tissue, and provide a second output control signal to the feedback generator based on the distance reaching a threshold distance.

Example 2—The control system of Example 1, wherein the input control device further comprises a handpiece. The feedback generator is embedded in the handpiece.

Example 3—The control system of Example 1, wherein the input control device further comprises a forearm support. The feedback generator is embedded in the forearm support.

Example 4—The control system of any one of Examples 1-3, wherein the feedback generator is configured to deliver haptic feedback to a surgeon upon receiving the second output control signal.

Example 5—The control system of any one of Examples 1-4, wherein the feedback generator comprises an eccentric rotating mass actuator.

Example 6—The control system of any one of Examples 1-4, wherein the feedback generator comprises a resistance generator configured to deliver a variable resistance based on the distance approaching the threshold distance.

Example 7—The control system of any one of Examples 1-6, wherein the feedback generator is configured to generate visual feedback upon receiving the second output control signal.

Example 8—The control system of any one of Examples 1-7, wherein the feedback generator is configured to produce an auditory signal upon receiving the second output control signal.

Example 9—A control system for a robotic surgical system, the control system comprising a surgical tool movable with respect to a tissue of a patient, an input control device comprising a base and a forearm support, and a control circuit. The forearm support is movable relative to the base within a first zone upon receipt of a precision input control motion to the forearm support. The forearm support is moveable relative to the base within a second zone upon receipt of a gross input control motion to the forearm support. The input control device further comprises a feedback generator. The control circuit is configured to receive an input control signal indicative of the precision input control motion and the gross input control motion, provide an output control signal to the surgical tool based on the input control signal, and provide a feedback signal to the feedback generator in response to the forearm support transitioning between the first zone and the second zone.

Example 10—The control system of Example 9, further comprising a proximity detection system configured to detect a distance between the surgical tool and the tissue. The gross input control motion is ignored by the control circuit when the distance between the surgical tool and the tissue is less than a threshold distance.

Example 11—The control system of Examples 9 or 10, wherein the first zone and the second zone comprise concentric zones. The first zone is surrounded by the second zone.

Example 12—The control system of any one of Examples 9-11, wherein the first zone comprises a first inner boundary, a first outer boundary, and a first radial width spanning from the first inner boundary to the first outer boundary. The second zone comprises a second inner boundary collinear with the first outer boundary, a second outer boundary, and a second radial width spanning from the second inner boundary to the second outer boundary. The second radial width is less than the first radial width Example 13—The control system of any one of Examples 9-12, wherein the input control device further comprises a detent arrangement positioned to provide tactile feedback to a user of the input control device when the user applies the gross input control motion to move the forearm support from the first zone to the second zone.

Example 14—The control system of any one of Examples 9-13, wherein the feedback generator is embedded in the forearm support.

Example 15—The control system of any one of Examples 9-13, wherein the input control device further comprises a shaft extending distally from the forearm support. The feedback generator is embedded in the shaft.

Example 16—A control system for a robotic surgical system, the control system comprising an input control device configured to receive input control motions. The input control device is configured to operate in a first operational mode and a second operational mode. The input control device comprises a feedback generator. The control system further comprises a control circuit configured to receive input control signals indicative of the input control motions received by the input control device, switch the input control device between the first operational mode and the second operational mode, provide first output control signals based on the input control signals in the first operational mode and provide second output control signals based on the input control signals in the second operational mode, and provide a feedback signal to the feedback generator in response to the input control device switching between the first operational mode and the second operational mode. The second output control signals are different than the first output control signals.

Example 17—The control system of Example 16, wherein the first operational mode comprises a precision motion mode and the second operational mode comprises a gross motion mode.

Example 18—The control system of Examples 16 or 17, further comprising a proximity detection system configured to detect a distance between a component of the robotic surgical system and a tissue. The control circuit is configured to switch the input control device between the first operational mode and the second operational mode when the proximity detection system detects the distance is less than a threshold distance.

Example 19—The control system of Example 18, wherein the proximity detection system comprises a structured light emitter and an optical receiver.

Example 20—The control system of any one of Examples 16-19, wherein the input control device further comprises a first component, a second component, and a joint intermediate the first component and the second component. The second component is configured to receive the input control motions. The second component is configured to move at the joint within a range of motion relative to the first component. The control circuit is further configured to provide a second feedback signal to the feedback generator in response to the second component approaching a limit of the range of motion at the joint.

Another list of Examples follows:

Example 1—A control system for a robotic surgical system, the control system comprising a robotic tool configured to detect a property of a tissue at a surgical site and an input control device comprising a base, a joystick coupled to the base, and a handpiece coupled to the joystick. The handpiece comprises a variable resistance assembly comprising a piston, a first jaw coupled to the piston, and a second jaw coupled to the piston. The first jaw and the second jaw are configured to receive user input control motions. The control system further comprises a control circuit configured to receive a jaw control signal indicative of the user input control motions received by the first jaw and the second jaw, provide a first output control signal to the robotic tool based on the jaw control signal, receive a tissue property signal indicative of the property of the tissue, and provide a second output control signal to the variable resistance assembly based on the tissue property signal.

Example 2—The control system of Example 1, wherein the variable resistance assembly further comprises an energized coil. The piston comprises a magnet configured to translate relative to the energized coil.

Example 3—The control system of Example 2, wherein the second output control signal to the variable resistance assembly is configured to adjust a current supplied to the energized coil.

Example 4—The control system of any one of Examples 1-3, wherein the handpiece further comprises a shaft. The first jaw and the second jaw are pivotably coupled to the shaft and the piston is configured to move along the shaft.

Example 5—The control system of Example 4, wherein the shaft comprises a linear actuator configured to effect a linear displacement of the piston in response to a pivotal displacement of the first jaw and the second jaw.

Example 6—The control system of any one of Examples 1-5, wherein the robotic tool further comprises a pair of end effector jaws. The property of the tissue comprises a pressure exerted on the pair of end effector jaws engaged with the tissue.

Example 7—The control system of Example 6, wherein the robotic tool further comprises a current sensor configured to detect a current drawn by a motor configured to actuate the pair of end effector jaws engaged with the tissue.

Example 8—A control system for a robotic surgical system, the control system comprising a robotic tool configured to detect a property of a tissue at a surgical site and an input control device comprising a base, a joystick coupled to the base, and a handpiece coupled to the joystick. The handpiece comprises a variable resistance assembly comprising a piston and a jaw coupled to the piston. The jaw is configured to receive a user input control motion. The control system further comprises a control circuit configured to receive a jaw control signal indicative of the user input control motion received by the jaw, provide a first output control signal to the robotic tool based on the jaw control signal, receive a tissue property signal indicative of the property of the tissue, and provide a second output control signal to the variable resistance assembly based on the property of the tissue.

Example 9—The control system of Example 8, wherein the variable resistance assembly further comprises an energized coil. The piston comprises a magnet configured to translate relative to the energized coil.

Example 10—The control system of Example 9, wherein the second output control signal to the variable resistance assembly is configured to adjust a current supplied to the energized coil.

Example 11—The control system of any one of Examples 8-10, wherein the variable resistance assembly comprises an electric motor.

Example 12—The control system of any one of Examples 8-11, wherein the handpiece further comprises a second variable resistance assembly comprising a second piston and a second jaw coupled to the second piston. The second jaw is configured to receive a second user input control motion.

Example 13—The control system of any one of Examples 8-12, wherein the robotic tool further comprises a pair of end effector jaws. The property of the tissue comprises a force exerted on the pair of end effector jaws clamping the tissue.

Example 14—The control system of Example 13, wherein the robotic tool further comprises a current sensor configured to detect a current drawn by a motor configured to actuate the pair of end effector jaws engaged with the tissue.

Example 15—A control system for a robotic surgical system, the control system comprising an input control device comprising a base, a joystick coupled to the base, and a handpiece coupled to the joystick. The handpiece comprises a variable resistance assembly comprising a piston, a first jaw coupled to the piston, and a second jaw coupled to the piston. The first jaw and the second jaw are configured to receive user input control motions. The control system further comprises a control circuit configured to receive jaw control signals indicative of the user input control motions received by the first jaw and the second jaw, provide first output control signals to a robotic tool of the robotic surgical system based on the jaw control signals, receive tissue property signals indicative of a tissue property, and provide second output control signals to the variable resistance assembly based on the tissue property.

Example 16—The control system of Example 15, wherein the variable resistance assembly further comprises an energized coil. The piston comprises a magnet configured to translate relative to the energized coil.

Example 17—The control system of Example 16, wherein the second output control signals to the variable resistance assembly are configured to adjust a current supplied to the energized coil.

Example 18—The control system of any one of Examples 15-17, wherein the handpiece further comprises a shaft. The first jaw and the second jaw are pivotably coupled to the shaft and the piston is configured to move along the shaft.

Example 19—The control system of Example 18, wherein the shaft comprises a linear actuator configured to effect a linear displacement of the piston in response to a pivotal displacement of the first jaw and the second jaw.

Example 20—The control system of any one of Examples 15-19, wherein the variable resistance assembly comprises an electric motor.

Another list of Examples follows:

Example 1—A control system for a robotic surgical system, the control system comprising a robotic tool comprising a tool jaw movable through a range of positions and an input control device. The input control device comprises a linear actuator and a pivotable jaw coupled to the linear actuator. The pivotable jaw is configured to pivot in response to a user input control motion and the linear actuator is configured to selectively pivot the pivotable jaw. The control system further comprises a control circuit configured to receive a first input control signal indicative of the user input control motion received by the pivotable jaw, provide a first output control signal to the robotic tool based on the first input control signal, receive a second input control signal from the robotic tool indicative of the position of the tool jaw within the range of positions, and provide a second output control signal to the linear actuator based on the second input control signal.

Example 2—The control system of Example 1, wherein the second output control signal is configured to match the angular orientation of the pivotable jaw to the angular orientation of the tool jaw.

Example 3—The control system of Examples 1 or 2, wherein the linear actuator comprises a rack and a servomechanism operably coupled to the rack.

Example 4—The control system of Examples 1 or 2, wherein the linear actuator comprises a reciprocating element and a first connector pivotably coupled to the pivotable jaw and the reciprocating element.

Example 5—The control system of any one of Examples 1-4, wherein the robotic tool further comprises a second tool jaw moveable through a second range of positions. The input control device further comprises a second pivotable jaw coupled to the linear actuator. The second pivotable jaw is configured to pivot in response to the user input control motion and the linear actuator is configured to selectively pivot the second pivotable jaw.

Example 6—The control system of any one of Examples 1-4, wherein the robotic tool further comprises a second tool jaw moveable through a second range of positions. The input control device further comprises a second linear actuator and a second pivotable jaw coupled to the second linear actuator.

Example 7—The control system of Example 6, wherein the linear actuator is independent of the second linear actuator.

Example 8—The control system of Examples 6 or 7, wherein the control circuit is further configured to receive a third input control signal indicative of the user input control motion received by the second pivotable jaw, provide a third output control signal to the robotic tool based on the third input control signal, receive a fourth input control signal from the robotic tool indicative of the position of the second pivotable jaw within the second range of positions, and provide a fourth output control signal to the second linear actuator based on the fourth input control signal.

Example 9—A control system for controlling a robotic surgical tool, the control system comprising an input control device comprising a base, a joystick extending from the base, and a handpiece extending from the joystick. The handpiece comprises a linear actuator, a first controller jaw coupled to the linear actuator, and a second controller jaw coupled to the linear actuator. The first controller jaw and the second controller jaw are configured to receive user input control motions and the linear actuator is configured to selectively drive the first controller jaw and the second controller jaw. The control system further comprises a control circuit configured to receive first input control signals indicative of user input control motions received by the first controller jaw and the second controller jaw, provide first output control signals to the robotic surgical tool based on the first input control signals, receive second input control signals from the robotic surgical tool indicative of a position of a first tool jaw and a second tool jaw of the robotic surgical tool, and provide second output control signals to the linear actuator based on the second input control signals Example 10—The control system of Example 9, wherein the second output control signals are configured to match the position of the first controller jaw to the position of the first tool jaw and the position of the second controller jaw to the position of the second tool jaw.

Example 11—The control system of Example 9, wherein the second output control signals are configured to match a controller angle between the first controller jaw and the second controller jaw to a tool angle between the first tool jaw and the second tool jaw.

Example 12—The control system of any one of Examples 9-11, wherein the linear actuator comprises a rack and a servomotor operably coupled to the rack.

Example 13—The control system of any one of Examples 9-11, wherein the linear actuator comprises a reciprocating element, a first connector pivotably coupled to the first controller jaw and the reciprocating element, and a second connector pivotably coupled to the second controller jaw and the reciprocating element.

Example 14—A control system for a robotic surgical system, the control system comprising a robotic tool comprising a tool jaw movable through a range of positions and a sensor configured to detect the position of the tool jaw within the range of positions. The control system further comprises a control circuit configured to receive a first input control signal indicative of a user input control motion received by an input jaw of an input control device, drive the tool jaw to an actuated position within the range of positions based on the first input control signal, receive a second input control signal from the robotic tool indicative of the position of the tool jaw within the range of positions, and provide an output control signal to drive the input jaw of the input control device based on the second input control signal.

Example 15—The control system of Example 14, wherein the sensor comprises a rotary encoder.

Example 16—The control system of Examples 14 or 15, wherein the robotic tool further comprises a second tool jaw moveable through a second range of positions and a second sensor configured to detect the position of the second tool jaw within the second range of positions.

Example 17—The control system of Example 16, wherein the control circuit is further configured to receive a third input control signal indicative of user input control motion received by a second input jaw of the input control device, drive the second tool jaw to an actuated position within the second range of positions based on the third input control signal, receive a fourth input control signal from the robotic tool indicative of the position of the second tool jaw within the second range of positions, and provide a second output control signal to drive the second input jaw of the input control device based on the fourth input control signal.

Example 18—A method comprising receiving a first input control signal indicative of a user input control motion applied to a controller jaw of an input control device, driving a jaw of a first robotic tool in response to the first input control signal, switching operable control by the input control device from the first robotic tool to a second robotic tool, receiving a second input control signal from the second robotic tool indicative of an angular orientation of a jaw of the second robotic tool, and driving the controller jaw of the input control device to correspond to the angular orientation of the jaw of the second robotic tool in response to the second input control signal.

Example 19—The method of Example 18, further comprising receiving a third input control signal from the second robotic tool indicative of the angular orientation of a second jaw of the second robotic tool and driving a second controller jaw of the input control device to correspond to the angular orientation of the second jaw of the second robotic tool in response to the second input control signal.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

What is claimed is:

1. A control system for a robotic surgical system, the control system comprising:
   a robotic tool configured to detect a property of a tissue at a surgical site;
   an input control device comprising a base, a joystick coupled to the base, and a handpiece coupled to the joystick, wherein the handpiece comprises:
   a variable resistance assembly comprising a piston;
   a first jaw coupled to the piston; and
   a second jaw coupled to the piston, wherein the first jaw and the second jaw are configured to receive user input control motions; and
   a control circuit configured to:
   receive a jaw control signal indicative of the user input control motions received by the first jaw and the second jaw;
   provide a first output control signal to the robotic tool based on the jaw control signal;
   receive a tissue property signal indicative of the property of the tissue; and
   provide a second output control signal to the variable resistance assembly based on the tissue property signal.

2. The control system of claim 1, wherein the variable resistance assembly further comprises an energized coil, and wherein the piston comprises a magnet configured to translate relative to the energized coil.

3. The control system of claim 2, wherein the second output control signal to the variable resistance assembly is configured to adjust a current supplied to the energized coil.

4. The control system of claim 1, wherein the handpiece further comprises a shaft, wherein the first jaw and the second jaw are pivotably coupled to the shaft, and wherein the piston is configured to move along the shaft.

5. The control system of claim 4, wherein the shaft comprises a linear actuator configured to effect a linear displacement of the piston in response to a pivotal displacement of the first jaw and the second jaw.

6. The control system of claim 1, wherein the robotic tool further comprises a pair of end effector jaws, and wherein the property of the tissue comprises a pressure exerted on the pair of end effector jaws engaged with the tissue.

7. The control system of claim 6, wherein the robotic tool further comprises a current sensor configured to detect a current drawn by a motor configured to actuate the pair of end effector jaws engaged with the tissue.

8. A control system for a robotic surgical system, the control system comprising:
- a robotic tool configured to detect a property of a tissue at a surgical site;
- an input control device comprising a base, a joystick coupled to the base, and a handpiece coupled to the joystick, wherein the handpiece comprises:
  - a variable resistance assembly comprising a piston; and
  - a jaw coupled to the piston, wherein the jaw is configured to receive a user input control motion; and
- a control circuit configured to:
  - receive a jaw control signal indicative of the user input control motion received by the jaw;
  - provide a first output control signal to the robotic tool based on the jaw control signal;
  - receive a tissue property signal indicative of the property of the tissue; and
  - provide a second output control signal to the variable resistance assembly based on the property of the tissue.

9. The control system of claim 8, wherein the variable resistance assembly further comprises an energized coil, and wherein the piston comprises a magnet configured to translate relative to the energized coil.

10. The control system of claim 9, wherein the second output control signal to the variable resistance assembly is configured to adjust a current supplied to the energized coil.

11. The control system of claim 8, wherein the variable resistance assembly comprises an electric motor.

12. The control system of claim 8, wherein the handpiece further comprises:
- a second variable resistance assembly comprising a second piston; and
- a second jaw coupled to the second piston, wherein the second jaw is configured to receive a second user input control motion.

13. The control system of claim 8, wherein the robotic tool further comprises a pair of end effector jaws, and wherein the property of the tissue comprises a force exerted on the pair of end effector jaws clamping the tissue.

14. The control system of claim 13, wherein the robotic tool further comprises a current sensor configured to detect a current drawn by a motor configured to actuate the pair of end effector jaws engaged with the tissue.

15. A control system for a robotic surgical system, the control system comprising:
- an input control device comprising a base, a joystick coupled to the base, and a handpiece coupled to the joystick, wherein the handpiece comprises:
  - a variable resistance assembly comprising a piston;
  - a first jaw coupled to the piston; and
  - a second jaw coupled to the piston, wherein the first jaw and the second jaw are configured to receive user input control motions; and
- a control circuit configured to:
  - receive jaw control signals indicative of the user input control motions received by the first jaw and the second jaw;
  - provide first output control signals to a robotic tool of the robotic surgical system based on the jaw control signals;
  - receive tissue property signals indicative of a tissue property; and
  - provide second output control signals to the variable resistance assembly based on the tissue property.

16. The control system of claim 15, wherein the variable resistance assembly further comprises an energized coil, and wherein the piston comprises a magnet configured to translate relative to the energized coil.

17. The control system of claim 16, wherein the second output control signals to the variable resistance assembly are configured to adjust a current supplied to the energized coil.

18. The control system of claim 15, wherein the handpiece further comprises a shaft, wherein the first jaw and the second jaw are pivotably coupled to the shaft, and wherein the piston is configured to move along the shaft.

19. The control system of claim 18, wherein the shaft comprises a linear actuator configured to effect a linear displacement of the piston in response to a pivotal displacement of the first jaw and the second jaw.

20. The control system of claim 19, wherein the variable resistance assembly comprises an electric motor.

* * * * *